US012582626B2

(12) United States Patent  
Ertl et al.

(10) Patent No.: US 12,582,626 B2  
(45) Date of Patent: *Mar. 24, 2026

(54) METHODS AND COMPOSITIONS FOR TREATING CANCER

(71) Applicant: The Wistar Institute of Anatomy and Biology, Philadelphia, PA (US)

(72) Inventors: Hildegund C.J. Ertl, Villanova, PA (US); Ying Zhang, Boston, MA (US)

(73) Assignee: The Wister Institute of Anatomy and Biology, Philadelphia, PA (US)

( * ) Notice: Subject to any disclaimer, the term of this patent is extended or adjusted under 35 U.S.C. 154(b) by 417 days.

This patent is subject to a terminal disclaimer.

(21) Appl. No.: 17/834,340

(22) Filed: Jun. 7, 2022

(65) Prior Publication Data

US 2022/0313643 A1 Oct. 6, 2022

Related U.S. Application Data

(63) Continuation of application No. 16/068,861, filed as application No. PCT/US2017/013387 on Jan. 13, 2017, now Pat. No. 11,382,886.

(60) Provisional application No. 62/420,271, filed on Nov. 10, 2016, provisional application No. 62/419,775, filed on Nov. 9, 2016, provisional application No. 62/279,252, filed on Jan. 15, 2016.

(51) Int. Cl.

| | |
|---|---|
| *A61K 31/216* | (2006.01) |
| *A61K 9/00* | (2006.01) |
| *A61K 31/192* | (2006.01) |
| *A61K 31/195* | (2006.01) |
| *A61K 31/7056* | (2006.01) |
| *A61K 35/26* | (2015.01) |
| *A61K 40/11* | (2025.01) |
| *A61K 40/31* | (2025.01) |
| *A61K 40/42* | (2025.01) |
| *A61P 35/00* | (2006.01) |
| *C07K 16/28* | (2006.01) |
| *C12N 5/0781* | (2010.01) |
| *C12N 5/0783* | (2010.01) |
| *G01N 33/574* | (2006.01) |
| *A61K 39/00* | (2006.01) |

(52) U.S. Cl.

CPC .......... *A61K 31/216* (2013.01); *A61K 9/0053* (2013.01); *A61K 31/192* (2013.01); *A61K 31/195* (2013.01); *A61K 31/7056* (2013.01); *A61K 35/26* (2013.01); *A61K 40/11* (2025.01); *A61K 40/31* (2025.01); *A61K 40/42* (2025.01); *A61K 40/4245* (2025.01); *A61P 35/00* (2018.01); *C07K 16/2818* (2013.01); *C12N 5/0635* (2013.01); *C12N 5/0636* (2013.01); *G01N 33/574* (2013.01); *A61K 2039/53* (2013.01); *A61K 2039/545* (2013.01); *A61K 2039/55516* (2013.01); *A61K 2239/31*

(2023.05); *A61K 2239/38* (2023.05); *A61K 2239/57* (2023.05); *C12N 2510/00* (2013.01); *C12N 2710/10043* (2013.01)

(58) Field of Classification Search  
None  
See application file for complete search history.

(56) References Cited

U.S. PATENT DOCUMENTS

| | | | |
|---|---|---|---|
| 9,114,117 | B2 | 8/2015 | Schmidt-Wolf |
| 2005/0233987 | A1 | 10/2005 | Blanco et al. |
| 2006/0009506 | A1 | 1/2006 | Westwick et al. |
| 2012/0028993 | A1 | 2/2012 | Schmidt-Wolf |
| 2015/0125463 | A1 | 5/2015 | Cogswell et al. |

FOREIGN PATENT DOCUMENTS

WO WO2012/079000 A1 6/2012

OTHER PUBLICATIONS

Byersdorfer, CA et al. The role of fatty acid oxidation in the metabolic reprograming of activated T-cells. Frontiers in Immunology. Dec. 18, 2014, vol. 5, No. 5, Article 641; pp. 1-7.

Jiang, Y. et al. T-cell exhaustion in the tumor microenvironment. Cell Death and Disease. Jun. 18, 2015, vol. 6, e1792.

Koltai, T. Fenofibrate in cancer: mechanisms involved in anticancer activity. [Version 2; referees:1 approved, 1approved with reservations] F1000Research 2015, 4:55 (Feb. 26, 2015) doi: 10.12688/f1000research.6153.1.

Mockler, MB et al, Targeting T cell immunometabolism for cancer immunotherapy; understanding the impact of the tumor microenvironment. Frontiers in Oncology, May 2014, vol. 4, Art. 107, pp. 1-11.

Patsoukis, N et al. PD-1 alters T-cell metabolic reprogramming by inhibiting glycolysis and promoting lipolysis and fatty acid oxidation. Nature Communications. Mar. 26, 2015, vol. 6, No. 6692; pp. 1-13.

Pauken, KE and EJ Wherry, Snapshot: T Cell Exhaustion. Cell, Nov. 5, 2015 vol. 163(4):1038-1038.e1.

(Continued)

*Primary Examiner* — Benjamin P Blumel  
(74) *Attorney, Agent, or Firm* — Howson & Howson, LLP; Colleen M. Schaller; Richard F. Kane

(57) ABSTRACT

Methods for treating cancer are disclosed which comprise administering to a subject T cells which have been pretreated ex vivo or in vitro with a fatty acid catabolism promoter to condition the T cell to use fatty acids rather than glucose for energy production. Still other methods comprise co-administering to a subject having a cancer characterized by a solid tumor (a) an immunotherapeutic composition targeting an antigen or ligand on the tumor cell; and (b) a compound or reagent that promotes the use of fatty acid catabolism by tumor antigen-specific T cells in the tumor microenvironment and/or T cells pretreated ex vivo with the fatty acid catabolism promoter to condition the T cell to use fatty acids rather than glucose for energy production for adoptive cell transfer. Both methods may also employ co-administration of a checkpoint inhibitor.

12 Claims, 35 Drawing Sheets  
Specification includes a Sequence Listing.

(56)                    References Cited

OTHER PUBLICATIONS

Waickman, AT et al. mTOR, metabolism, and the regulation of T-cell differentiation and function. Immunology Reviews. Sep. 1, 2012, vol. 249, No. 1; pp. 43-58.

Wilk, A et al. Molecular Mechanisms of Fenofibrate-Induced Metabolic Catastrophe and Glioblastoma Cell Death. Mol. Cell. Biol., Jan. 2015 vol. 35(1):182-198.

Zhang, Y et al, Enhancing CD8+ T Cell Fatty Acid Catabolism within a Metabolically Challenging Tumor Microenvironment Increases the Efficacy of Melanoma Immunotherapy. Cancer Cell, Sep. 2017 vol. 32:377-391.

Zhang, Y et al, Starved and Asphyxiated: How Can CD8+ T Cells within a Tumor Microenvironment Prevent Tumor Progression. Frontiers in Immunol., Feb. 10, 2016 vol. 7, Art 32: 1-7.

Ahmadzadeh, M., et al. (May 2009). Tumor antigen-specific CD8 T cells infiltrating the tumor express high levels of PD-1 and are functionally impaired. Blood 114(8): 1537-1544.

Azuma, T., et al., (Jan. 2008) B7-H1 is a ubiquitous antiapoptotic receptor on cancer cells. Blood 111: 3635-3643.

Bailey, K.M., et al. (2012). Targeting the metabolic microenvironment of tumors. Adv. Pharmacol. 65, 63-107.

Baitsch, L. (Jun. 2011). Exhaustion of tumor-specific CD8+ T cells in metastases from melanoma patients. J. Clin. Invest. 121:2350-60.

Brahmer, J.R., et al. (Jun. 2012). Safety and Activity of Anti-PD-L1 Antibody in Patients with Advanced Cancer. N. Engl. J. Med. 366, 2455-2465.

Bucks, C.M., et al. (Jun. 2009). Chronic antigen stimulation alone is sufficient to drive CD8+ T cell exhaustion. J. Immunol. 182, 6697-6708.

Chang, C.H., et al. (Sep. 2015) Metabolic Competition in the Tumor Microenvironment Is a Driver of Cancer Progression. Cell. 162, 1229-41.

Chapman, P.B., et al. (Apr. 2015). Rapid eradication of a bulky melanoma with one dose of immunotherapy. N. Engl. J. Med. 372, 2073-2074. Online Publ. Nov. 2014.

Crompton, J.G., et al. (Jan. 2015). Akt inhibition enhances expansion of potent tumor-specific lymphocytes with memory cell characteristics. Cancer. Res. 75, 296-305.

Doedens, A.L., et al. (Nov. 2013). Hypoxia-inducible factors enhance the effector responses of CD8(+) T cells to persistent antigen. Nat Immunol. 14, 1173-82.

Finlay, D., et al. (Nov. 2012). PDK1 regulation of mTOR and hypoxia-inducible factor 1 integrate metabolism and migration of CD8+ T cells. J. Exp. Med. 209, 2441-2453.

Grosso, J.F., et al. (Nov. 2007). LAG-3 regulates CD8+ T cell accumulation and effector function in murine self-and tuor-tolerance systems. J. Clin. Invest. 117, 3383-3392.

Hamanaka, R.B. and Chandel, N.S. (Feb. 2012). Targeting glucose metabolism for cancer therapy. J. Exp. Med. 209, 211-215.

Ho, P.C., et al. (Sep. 2015). Phosphoenolpyruvate is a metabolic checkpoint of anti-tumor T cell response. Cell.162; 1217-28.

Kalos, M. et al (Aug. 2011) T cells with chimeric antigen receptors have potent antitumor effects and can establish Memory in Patients with Advanced Leukemia. Sci Transl Med., 3(95): 73.

Kleffel, S., et al., (Sep. 2015) Melanoma Cell-Intrinsic PD-1 Receptor Functions Promote Tumor Growth. Cell 162, 1242-1256.

Larkin, J., et al., (May 2015) Combined Nivolumab and Ipilimumab or Monotherapy in Untreated Melanoma. N Engl J Med 373, 23-34.

Lasaro, M.O. et al. (Feb. 2008). Targeting of antigen to the herpes-virus entry mediator augments primary adaptive immune responses. Nat. Med. 14, 205-212.

Lu, W., et al. (Apr. 2010). Metabolomic analysis via reversed-phase ion-pairing liquid chromatography coupled to a stand alone orbitrap mass spectrometer. Anal. Chem. 82, 3212-21.

Martinez-Outschoorn, U.E., et al (Nov. 2012). Ketone body utilization drives tumor growth and metastasis. Cell Cycle. 11(21): 3964-71.

Marvel, D., Gabrilovich, D.I., (Sep. 2015) Myeloid-derived suppressor cells in the tumor microenvironment: expect the unexpected. J. Clin. Invest. 125, 3356-3364.

McNamee, E.N. et al. (Mar. 2013). Hypoxia and hypoxia-inducible factors as regulators of T cell development, differentiation, and function. Immunol. Res. 55, 58-70.

Menendez, J.A. and Lupu, R. (Nov. 2007). Fatty acid synthase and lipogenic phenotype in cancer pathogenesis. Nat. Rev. Cancer. 7, 763-777.

Mrass, P., et al., (Nov. 2006) Random migration precedes stable target cell interactions of tumor-infiltrating T cells. Journal of Experimental Medicine 203, 2749-2761.

Mueller, S.N. and Ahmed, R. (May 2009). High antigen levels are the cause of T cell exhaustion during chronic viral infection. Proc. Natl. Acad. Sci. 106(21): 8623-8628.

Ohta, A., et al., (Jul. 2011) In vivo T cell activation in lymphoid tissues is inhibited in the oxygen-poor microenvironment. Front Immunol 2, 27.

Palmer, C.S., et al. (Jan. 2015). Glucose metabolism regulates T cell activation, differentiation, and functions. Frontiers Immunol. 6, 1-6.

Parry, R.V., et al. (Nov. 2005). CTLA-4 and PD-1 receptors inhibit T-cell activation by distinct mechanisms. Mol. Cell. Biol. 25(21): 9543-53.

Patsoukis, N., et al., (Aug. 2013) PD-1 increases PTEN phosphatase activity while decreasing PTEN protein stability by inhibiting casein kinase 2. Mol. Cell. Biol. 33, 3091-3098; Publ online Jun. 2013.

Pearce, E.L. (Oct. 2013). Fueling immunity: insights into metabolism and lymphocyte function. Science. 342; 1242454.

Pescador, N., et al. (Apr. 2005). Identification of a functional hypoxia-responsive element that regulates the expression of the egl nine homologue 3 (egln3/phd3) gene. Biochem. J. 390, 189-197.

Schlie, K., et al. (Aug. 2011). When Cells Suffocate: Autophagy in Cancer and Immune Cells under Low Oxygen. Int J Cell Biol 2011, 470597-13.

Sharma, P. and Allison, J.P. (Apr. 2015). Immune checkpoint targeting in cancer therapy: toward combination strategies with curative potential. Cell. 161, 205-214.

Siska, P.J. and Rathmell, J.C. (Apr. 2015) T cell metabolic fitness in antitumor immunity. Trends Immunol. 36, 257-64.

Sukumar, M., et al. (Oct. 2013). Inhibiting glycolytic metabolism enhances CD8+T cell memory and antitumor function. J.Clin. Invest. 123, 4479-88.

Takahashi, S., et al. (Jul. 2014). Roles and regulation of ketogenesis in cultured astroglia and neurons under hypoxia and hypoglycemia. ASN. Neuro. 6, 5.

Tatsis, N., et al., (Sep. 2007) Adenoviral vectors persist in vivo and maintain activated CD8+ T cells: implications for their use as vaccines. Blood 110, 1916-1923. Online publ May 2007.

Veech, R.L. (2004). The therapeutic implications of ketone bodies: the effects of ketone bodies in pathological conditions: ketosis, ketogenic diet, redox states, insulin resistance, and mitochondrial metabolism. Prostaglandins. Leukot. Essent. Fatty. Acids. 70, 309-19.

Wang, R.W. and Green, D.R. (Sep. 2012). Metabolic checkpoints in activated T cells. Nat. Immunol. 13, 907-915.

Wiig, H., et al. (2003). Isolation of interstitial fluid from rat mammary tumors by a centrifugation method. Am. J. Physiol. Heart. Circ. Physiol. 284, H416-24. Publ online Sep. 2002.

Zhang, F., (Aug. 2012) Dysregulated lipid metabolism in cancer. World Journal of Biological Chemistry 3, 167-174.

Zhang, Y. and Ertl, H.C. (Aug. 2014). The effect of adjuvanting cancer vaccines with herpes simplex virus glycoprotein D on melanoma-driven CD8+ T cell exhaustion. J. Immunol. 193: 1836-1846.

Zhang, Y., et al. (2012). Stromal progenitor cells from endogenous adipose tissue contribute to pericytes and adipocytes that populate the tumor microenvironment. Cancer Res. 72, 5198-208.

Zou, W., et al., (Mar. 2016) PD-L1 (B7-H1) and PD-1 pathway blockade for cancer therapy: Mechanisms, response biomarkers, and combinations. Sci Transl Med 8, 328rv4-328rv4.

Casazza, A. et al., Tumor stroma: a complexity dictated by the hypoxic tumor microenvironment, Oncogene, Apr. 2013, 33(14):1743-1754.

(56) References Cited

OTHER PUBLICATIONS

Clarke, S. R. et al., Characterization of the ovalbumin-specific TCR transgenic line OT-I: MHC elements for positive and negative selection, Apr. 2000, Immunology and Cell Biology, 78(2):110-117.

Dalgleish, A. G., Therapeutic cancer vaccines: Why so few randomized phase III studies reflect the initial optimism of phase II studies, Vaccine, Sep. 2011, 29:8501-8505.

Lochner, M. et. al., Fatty acid metabolism in the regulation of T cell function, Trends in Immunology, Feb. 2015, 36(2):472-478.

Wein House, S. et al., On respiratory impairment in cancer cells, Science, Aug. 1956, 124(3215):267-272.

Wherry, E. J., T cell exhaustion, Nature Immunology, May 2011, 12(6):492-499.

Yang, J. C., The adoptive transfer of cultured T cells for patients with metastatic melanoma, Clinics in Dermatology, Mar. 2013, 31(2):209-219.

Pacella, I. et al., "Fatty acid metabolism complements glycolysis in the selective regulatory T cell expansion during tumor growth" Proc Natl Acad Sci U S A. Jul. 10, 2018;115(28):E6546-E6555. doi: 10.1073/pnas.1720113115. Epub Jun. 25, 2018.

Hossain, F. et al., "Inhibition of Fatty Acid Oxidation Modulates Immunosuppressive Functions of Myeloid-Derived Suppressor Cells and Enhances Cancer Therapies" Cancer Immunol Res. Nov. 2015;3(11):1236-47. doi: 10.1158/2326-6066.CIR-15-0036. Epub May 29, 2015.

Samuel, S. et al., "B052: Peroxisome proliferator-activated receptor delta agonist GW501516 enhances the efficacy of adoptive cell therapy" In: Proceedings of the Second CRI-CIMT-EATI-AACR International Cancer Immunotherapy Conference: Translating Science into Survival; Sep. 25-28, 2016; New York, NY. Philadelphia (PA): AACR; Cancer Immunol Res 2016;4(11 Suppl):Abstract nr B052.

International Search Report and Written Opinion dated Apr. 6, 2017 in corresponding International Patent Application PCT/US2017/013387, filed Jan. 13, 2017.

European Search Report dated Aug. 1, 2019 in corresponding European Patent Application EP17739022.6, European Regional Phase Entry of PCT/US2017/013387, filed Jan. 13, 2017.

Restriction Requirement dated Aug. 13, 2019 in related U.S. Appl. No. 16/068,861, filed Jul. 9, 2018.

Response to Restriction Requirement dated Oct. 11, 2019 in related U.S. Appl. No. 16/068,861, filed Jul. 9, 2018.

Non-Final Office Action dated Feb. 24, 2020 in related U.S. Appl. No. 16/068,861, filed Jul. 9, 2018.

Response to Non-Final Office Action dated Jul. 23, 2020 in related U.S. Appl. No. 16/068,861, filed Jul. 9, 2018.

Final Office Action dated Oct. 29, 2020 in related U.S. Appl. No. 16/068,861, filed Jul. 9, 2018.

Response to Final Office Action dated Jan. 29, 2021 in related U.S. Appl. No. 16/068,861, filed Jul. 9, 2018.

Non-Final Office Action dated Sep. 14, 2021 in related U.S. Appl. No. 16/068,861, filed Jul. 9, 2018.

Response to Non-Final Office Action dated May 14, 2022 in related U.S. Appl. No. 16/068,861, filed Jul. 9, 2018.

Human melanoma samples

Hypoxia Effect

Transcripts

| Comparisons | Glu uptake | | Glycolysis | TCA cycle | | Regulation FA metab. | FA uptake | | TG synthesis | | Lipolysis | | Peroxisomal FAO | | | | Mitochondrial FAO | | Ketone Body metab. | ROS metabolism | | | ETC |
|---|---|---|---|---|---|---|---|---|---|---|---|---|---|---|---|---|---|---|---|---|---|---|---|
| Pathways / Enzyme/Factors | GLUT1 | HK-2 | PGK1 | IDH3a | MDH2 | PPAR-α | Slc27a4 | Slc27a2 | DGAT1 | DGAT2 | PNPLA2 | LIPA | ACAA1a | EHHADH | ACOX1 | HSD17b4 | ACADVl | ACADM | BDH1 | NOX1 | SOD1 | CAT | COX5b |
| Gal. H/Glu. H | 0 | 0 | 0 | 0 | 0 | | | | | | | | | | | | | | | | 0 | 0 | 0 |
| Glu+ 2-DG, H/Glu, H | 0 | 0 | 0 | 0 | 0 | | | | | | | | | | | 0 | | | | | 0 | | 0 |
| Trp-1 TILs, mo1/wk2 | 0 | 0 | 0 | 0 | 0 | | | | | | | | | 0 | | 0 | | | | | 0 | 0 | 0 |
| E7 TILs, mo1/wk2 | 0 | 0 | 0 | 0 | 0 | | | | | | | | | | | | | | | | 0 | 0 | 0 |
| Trp-1 spl, mo3/wk2 | | 0 | 0 | 0 | 0 | 0 | 0 | 0 | 0 | | | 0 | | 0 | 0 | | | | | | 0 | 0 | |
| E7 spl, mo3/wk2 | 0 | 0 | 0 | 0 | 0 | 0 | 0 | 0 | 0 | | | 0 | | 0 | 0 | | | | | | 0 | 0 | |

Legend:
- Similar to in vitro changes
- ○ Different from in vitro changes
- △ Dependent on culture condition

FIG. 4B

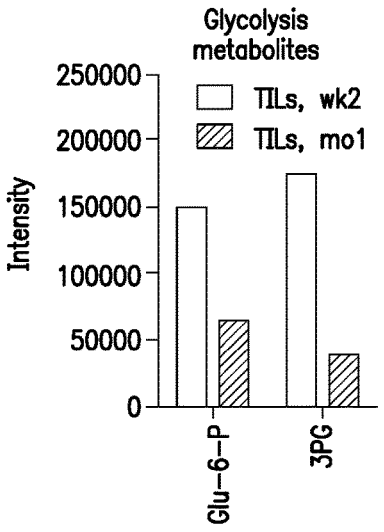

Glycolysis metabolites
- TILs, wk2
- TILs, mo1

Intensity (Glu-6-P, 3PG)

FIG. 4C

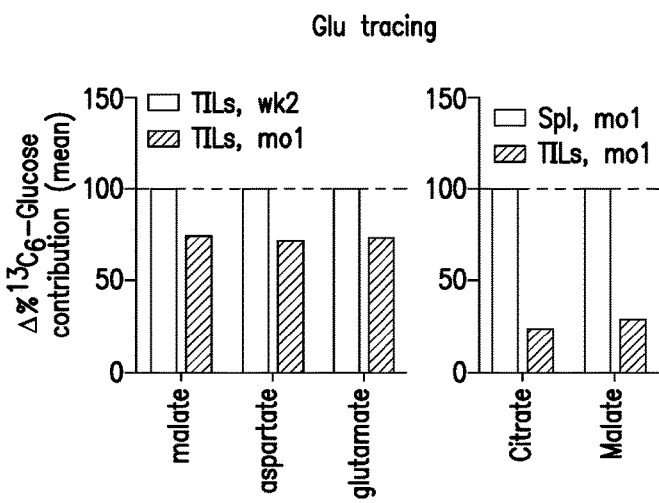

Glu tracing
- TILs, wk2
- TILs, mo1
- Spl, mo1
- TILs, mo1

Δ% $^{13}C_6$-Glucose contribution (mean)

(malate, aspartate, glutamate) / (Citrate, Malate)

FIG. 4D

FA metabolites

FA tracing

Prior to transfer: Phenotypes, donor cells

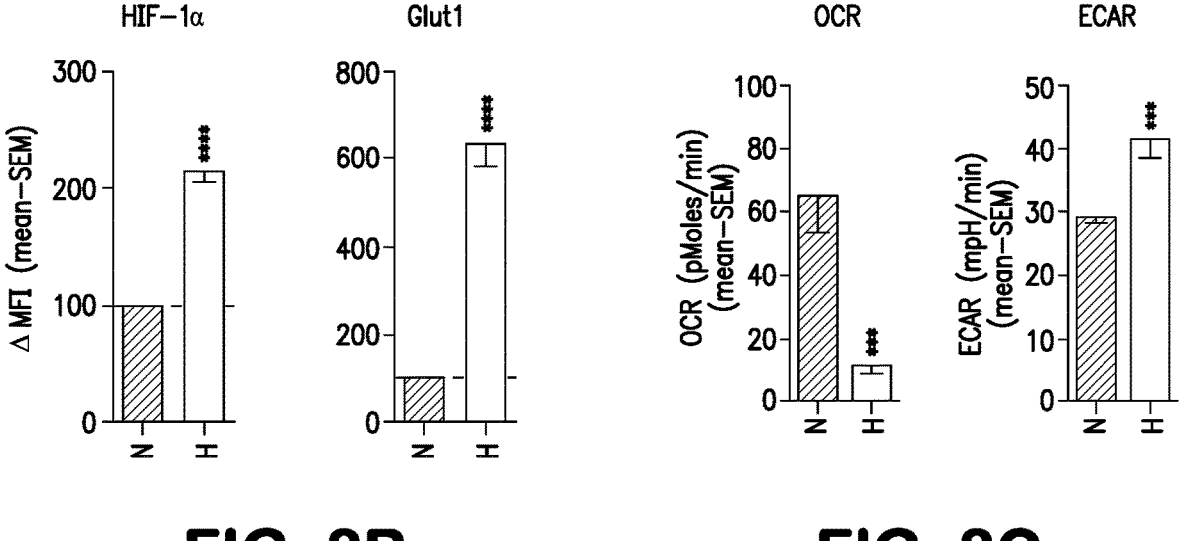
FIG. 8B          FIG. 8C

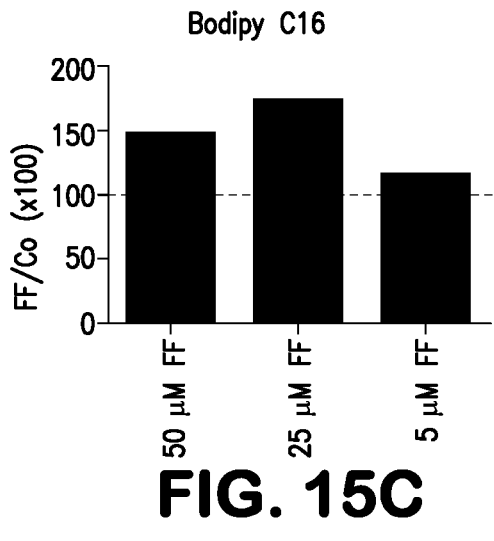
FIG. 15C
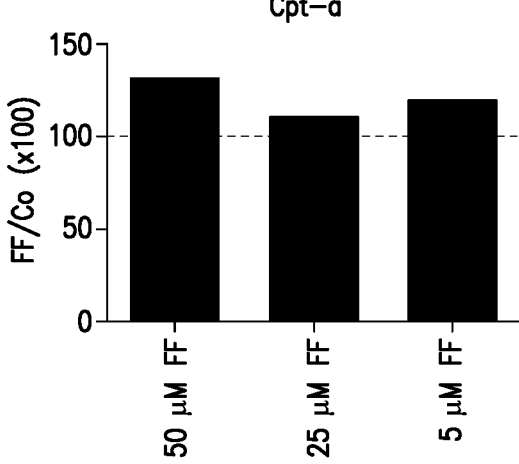
FIG. 15D
FIG. 15E

| Function | Transcript | Fenofibrate (mM) | | |
|---|---|---|---|---|
| | | 5 | 25 | 50 |
| Glu uptake | Glut1 | 0 | | |
| TCA cycle | IDH3a | | | 0 |
| | MDH2 | 0 | | |
| FAO regulation | PPARalpha | 0 | | |
| FA transport | Slc27a4 | | | 0 |
| | Slca2 | 0 | | |
| Peroxisomal FAO | ACAA1a | 0 | 0 | |
| | EHHADH | | | 0 |
| | Acox1 | | | |
| | Hsd17b4 | | | 0 |
| Mitochondrial FAO | ACADVL | 0 | | |
| | ACADM | | | 0 |
| | Cpt1a | | | 0 |
| Ketone body met. | BDH1 | | | | low  [0]  high

SEQUENCE LISTING

<160> NUMBER OF SEQ ID NOS: 46

<210> SEQ ID NO 1
<211> LENGTH: 8
<212> TYPE: PRT
<213> ORGANISM: Mus musculus

<400> SEQUENCE: 1

Ser Ile Ile Asn Phe Glu Lys Leu
1               5

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
tgtgggagga gcagtgctcg                                              20

<210> SEQ ID NO 3
<211> LENGTH: 19
<212> TYPE: DNA
<213> ORGANISM: Artificial Sequence
<220> FEATURE:
<223> OTHER INFORMATION: Reverse primer

<400> SEQUENCE: 3
tgggctctcc gtagcggtg                                               19

<210> SEQ ID NO 4
<211> LENGTH: 21
<212> TYPE: DNA
<213> ORGANISM: Artificial Sequence
<220> FEATURE:
<223> OTHER INFORMATION: Forward primer

<400> SEQUENCE: 4
tgatcgcctg cttattcacg g                                            21

<210> SEQ ID NO 5
<211> LENGTH: 23
<212> TYPE: DNA
<213> ORGANISM: Artificial Sequence
<220> FEATURE:
<223> OTHER INFORMATION: Reverse primer

<400> SEQUENCE: 5
accgcctaga aatctccaga agg                                          23

<210> SEQ ID NO 6
<211> LENGTH: 21
<212> TYPE: DNA
<213> ORGANISM: Artificial Sequence
<220> FEATURE:
<223> OTHER INFORMATION: Forward primer

<400> SEQUENCE: 6
atgtcgcttt ccaacaagct g                                            21

<210> SEQ ID NO 7
<211> LENGTH: 20
<212> TYPE: DNA
<213> ORGANISM: Artificial Sequence
<220> FEATURE:

-continued

<223> OTHER INFORMATION: Reverse primer

<400> SEQUENCE: 7
tggctccatt gtccaagcag                                                    20

<210> SEQ ID NO 8
<211> LENGTH: 20
<212> TYPE: DNA
<213> ORGANISM: Artificial Sequence
<220> FEATURE:
<223> OTHER INFORMATION: Forward primer

<400> SEQUENCE: 8
tgggtgtcca aggtctctcg                                                    20

<210> SEQ ID NO 9
<211> LENGTH: 20
<212> TYPE: DNA
<213> ORGANISM: Artificial Sequence
<220> FEATURE:
<223> OTHER INFORMATION: Reverse primer

<400> SEQUENCE: 9
tctgggccaa ttccatctcc                                                    20

<210> SEQ ID NO 10
<211> LENGTH: 20
<212> TYPE: DNA
<213> ORGANISM: Artificial Sequence
<220> FEATURE:
<223> OTHER INFORMATION: Forward primer

<400> SEQUENCE: 10
ttgggcaacc cctttcactc                                                    20

<210> SEQ ID NO 11
<211> LENGTH: 22
<212> TYPE: DNA
<213> ORGANISM: Artificial Sequence
<220> FEATURE:
<223> OTHER INFORMATION: Reverse primer

<400> SEQUENCE: 11
tgtgactcag atctgctgcc ac                                                 22

<210> SEQ ID NO 12
<211> LENGTH: 21
<212> TYPE: DNA
<213> ORGANISM: Artificial Sequence
<220> FEATURE:
<223> OTHER INFORMATION: Forward primer

<400> SEQUENCE: 12
agccccatct gtcctctctc c                                                  21

<210> SEQ ID NO 13
<211> LENGTH: 22
<212> TYPE: DNA
<213> ORGANISM: Artificial Sequence
<220> FEATURE:
<223> OTHER INFORMATION: Reverse primer

<400> SEQUENCE: 13
tccagagctc tcctcaccga tg                                                 22

-continued

```
<210> SEQ ID NO 14
<211> LENGTH: 24
<212> TYPE: DNA
<213> ORGANISM: Artificial Sequence
<220> FEATURE:
<223> OTHER INFORMATION: Forward primer

<400> SEQUENCE: 14
tgagtttgtg ggtctgtggc tagg                                        24

<210> SEQ ID NO 15
<211> LENGTH: 21
<212> TYPE: DNA
<213> ORGANISM: Artificial Sequence
<220> FEATURE:
<223> OTHER INFORMATION: Reverse primer

<400> SEQUENCE: 15
aagacagtgg cgcagggcat c                                           21

<210> SEQ ID NO 16
<211> LENGTH: 20
<212> TYPE: DNA
<213> ORGANISM: Artificial Sequence
<220> FEATURE:
<223> OTHER INFORMATION: Forward Primer

<400> SEQUENCE: 16
tgctgctgct gcctctgctg                                             20

<210> SEQ ID NO 17
<211> LENGTH: 20
<212> TYPE: DNA
<213> ORGANISM: Artificial Sequence
<220> FEATURE:
<223> OTHER INFORMATION: Reverse primer

<400> SEQUENCE: 17
aggatggtac gcacgggtcg                                             20

<210> SEQ ID NO 18
<211> LENGTH: 23
<212> TYPE: DNA
<213> ORGANISM: Artificial Sequence
<220> FEATURE:
<223> OTHER INFORMATION: Forward primer

<400> SEQUENCE: 18
acctggccac aatcatctgc ttc                                         23

<210> SEQ ID NO 19
<211> LENGTH: 20
<212> TYPE: DNA
<213> ORGANISM: Artificial Sequence
<220> FEATURE:
<223> OTHER INFORMATION: Reverse primer

<400> SEQUENCE: 19
ttggccttga cccttcgctg                                             20

<210> SEQ ID NO 20
<211> LENGTH: 22
<212> TYPE: DNA
<213> ORGANISM: Artificial Sequence
<220> FEATURE:
<223> OTHER INFORMATION: Forward primer
```

-continued

<400> SEQUENCE: 20
agcatcctct cagccctcca ag                                                    22

<210> SEQ ID NO 21
<211> LENGTH: 22
<212> TYPE: DNA
<213> ORGANISM: Artificial Sequence
<220> FEATURE:
<223> OTHER INFORMATION: Reverse primer

<400> SEQUENCE: 21
tagcaccagg aaggatagga cc                                                    22

<210> SEQ ID NO 22
<211> LENGTH: 20
<212> TYPE: DNA
<213> ORGANISM: Artificial Sequence
<220> FEATURE:
<223> OTHER INFORMATION: Forward primer

<400> SEQUENCE: 22
ttcccgaggg agaccaagtg                                                       20

<210> SEQ ID NO 23
<211> LENGTH: 19
<212> TYPE: DNA
<213> ORGANISM: Artificial Sequence
<220> FEATURE:
<223> OTHER INFORMATION: Reverse primer

<400> SEQUENCE: 23
tgccgaggct ccgtagatg                                                        19

<210> SEQ ID NO 24
<211> LENGTH: 19
<212> TYPE: DNA
<213> ORGANISM: Artificial Sequence
<220> FEATURE:
<223> OTHER INFORMATION: Forward primer

<400> SEQUENCE: 24
tgctttctcg ggtgcccac                                                        19

<210> SEQ ID NO 25
<211> LENGTH: 21
<212> TYPE: DNA
<213> ORGANISM: Artificial Sequence
<220> FEATURE:
<223> OTHER INFORMATION: Reverse primer

<400> SEQUENCE: 25
tcctcaccag gatatcccca g                                                     21

<210> SEQ ID NO 26
<211> LENGTH: 19
<212> TYPE: DNA
<213> ORGANISM: Artificial Sequence
<220> FEATURE:
<223> OTHER INFORMATION: Forward primer

<400> SEQUENCE: 26
tccgctaggt tcccgcagg                                                        19

<210> SEQ ID NO 27
<211> LENGTH: 19

-continued

```
<212> TYPE: DNA
<213> ORGANISM: Artificial Sequence
<220> FEATURE:
<223> OTHER INFORMATION: Forward primer

<400> SEQUENCE: 27
aaagttcgaa agggcaagg                                                    19

<210> SEQ ID NO 28
<211> LENGTH: 19
<212> TYPE: DNA
<213> ORGANISM: Artificial Sequence
<220> FEATURE:
<223> OTHER INFORMATION: Reverse primer

<400> SEQUENCE: 28
tcgcccagct tcacagagc                                                    19

<210> SEQ ID NO 29
<211> LENGTH: 19
<212> TYPE: DNA
<213> ORGANISM: Artificial Sequence
<220> FEATURE:
<223> OTHER INFORMATION: Forward primer

<400> SEQUENCE: 29
tcccgatctg cgcaaggag                                                    19

<210> SEQ ID NO 30
<211> LENGTH: 23
<212> TYPE: DNA
<213> ORGANISM: Artificial Sequence
<220> FEATURE:
<223> OTHER INFORMATION: Reversion primver

<400> SEQUENCE: 30
tgttctccgg actaccatcc aag                                               23

<210> SEQ ID NO 31
<211> LENGTH: 23
<212> TYPE: DNA
<213> ORGANISM: Artificial Sequence
<220> FEATURE:
<223> OTHER INFORMATION: Forward primer

<400> SEQUENCE: 31
ttgtgaacga cttaggaggg gac                                               23

<210> SEQ ID NO 32
<211> LENGTH: 22
<212> TYPE: DNA
<213> ORGANISM: Artificial Sequence
<220> FEATURE:
<223> OTHER INFORMATION: Reverse primer

<400> SEQUENCE: 32
aaatgtgtcc agtgccgtcg gc                                                22

<210> SEQ ID NO 33
<211> LENGTH: 23
<212> TYPE: DNA
<213> ORGANISM: Artificial Sequence
<220> FEATURE:
<223> OTHER INFORMATION: Forward primer

<400> SEQUENCE: 33
```

-continued accctctcct ctgatgcttc cac                                            23

<210> SEQ ID NO 34
<211> LENGTH: 23
<212> TYPE: DNA
<213> ORGANISM: Artificial Sequence
<220> FEATURE:
<223> OTHER INFORMATION: Reverse primer

<400> SEQUENCE: 34
tgagcacaga tgggtatggg aac                                            23

<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35
aagcaggagc ccggattagg                                                20

<210> SEQ ID NO 36
<211> LENGTH: 21
<212> TYPE: DNA
<213> ORGANISM: Artificial Sequence
<220> FEATURE:
<223> OTHER INFORMATION: Reverse primer

<400> SEQUENCE: 36
tccccgcttt tgtcatattc c                                              21

<210> SEQ ID NO 37
<211> LENGTH: 21
<212> TYPE: DNA
<213> ORGANISM: Artificial Sequence
<220> FEATURE:
<223> OTHER INFORMATION: Forward primer

<400> SEQUENCE: 37
tcgccatact gcatcaccaa g                                              21

<210> SEQ ID NO 38
<211> LENGTH: 20
<212> TYPE: DNA
<213> ORGANISM: Artificial Sequence
<220> FEATURE:
<223> OTHER INFORMATION: Reverse primer

<400> SEQUENCE: 38
tgccaggttc caccacactg                                                20

<210> SEQ ID NO 39
<211> LENGTH: 23
<212> TYPE: DNA
<213> ORGANISM: Artificial Sequence
<220> FEATURE:
<223> OTHER INFORMATION: Forward primer

<400> SEQUENCE: 39
agaaattctt gggactgcct tgg                                            23

<210> SEQ ID NO 40
<211> LENGTH: 20
<212> TYPE: DNA
<213> ORGANISM: Artificial Sequence -continued

```
<220> FEATURE:
<223> OTHER INFORMATION: Reverse primer

<400> SEQUENCE: 40
tgcccctcaa gaaggacagc                                             20

<210> SEQ ID NO 41
<211> LENGTH: 22
<212> TYPE: DNA
<213> ORGANISM: Artificial Sequence
<220> FEATURE:
<223> OTHER INFORMATION: Forward primer

<400> SEQUENCE: 41
acaggattaa ctgaaggcca gc                                          22

<210> SEQ ID NO 42
<211> LENGTH: 20
<212> TYPE: DNA
<213> ORGANISM: Artificial Sequence
<220> FEATURE:
<223> OTHER INFORMATION: Reverse primer

<400> SEQUENCE: 42
ttgcccaggt ctccaacatg                                             20

<210> SEQ ID NO 43
<211> LENGTH: 22
<212> TYPE: DNA
<213> ORGANISM: Artificial Sequence
<220> FEATURE:
<223> OTHER INFORMATION: Forward primer

<400> SEQUENCE: 43
tgacatggtc tgggacttct gg                                          22

<210> SEQ ID NO 44
<211> LENGTH: 19
<212> TYPE: DNA
<213> ORGANISM: Artificial Sequence
<220> FEATURE:
<223> OTHER INFORMATION: Forward primer

<400> SEQUENCE: 44
agccattcat gtgccggtg                                              19

<210> SEQ ID NO 45
<211> LENGTH: 19
<212> TYPE: DNA
<213> ORGANISM: Artificial Sequence
<220> FEATURE:
<223> OTHER INFORMATION: Forward primer

<400> SEQUENCE: 45
acccgctcca tggcttctg                                              19

<210> SEQ ID NO 46
<211> LENGTH: 24
<212> TYPE: DNA
<213> ORGANISM: Artificial Sequence
<220> FEATURE:
<223> OTHER INFORMATION: Reverse primer

<400> SEQUENCE: 46
agtcccttct gtgctgctat catg                                        24
```

METHODS AND COMPOSITIONS FOR TREATING CANCER

CROSS-REFERENCE TO RELATED APPLICATIONS

This application is a continuation of U.S. patent application Ser. No. 16/068,861, filed Jul. 9, 2018, which is a national stage of International Patent Application No. PCT/US2017/013387, filed Jan. 13, 2017, which claims the benefit of the priorities of U.S. Provisional Patent Application No. 62/420,271, filed Nov. 10, 2016; U.S. Provisional Patent Application No. 62/419,775, filed Nov. 9, 2016; and U.S. Provisional Patent Application No. 62/279,252, filed Jan. 15, 2016, which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "WST161PCT_ST25.txt" and dated Jan. 9, 2017.

BACKGROUND OF THE INVENTION

Despite recent progress in cancer immunotherapy,[7,29] cures remain rare even for highly immunogenic tumors such as melanomas. The tumor microenvironment (TME) poses significant metabolic challenges to TILs due to disorganized vascularization, presence of toxic products derived from tumor and stromal cells and lack of nutrients and oxygen $(O_2)$.[2] Two recent papers show that lack of glucose impairs effect functions of tumor infiltrating T lymphocytes (TILs).[6,14] Tumors not only lack glucose but also oxygen. Functional declines of tumor-infiltrating T lymphocytes (TILs) dampen the efficacy of immunotherapy for solid tumors. This is thought to reflect in part their exhaustion driven by continuous antigenic stimulation. Adoptive transfer of ex vivo expanded TILs may affect regression of large melanomas[38]. Nevertheless, traditional vaccines that aim to induce such T cells have largely been ineffective.[9] Exhaustion of tumor antigen (TA)-specific CD8+ T cells[1,3] is characterized by their enhanced expression of co-inhibitors, decreased levels of the transcription factor T-bet and loss of effector functions[36] following chronic tumor-derived antigen stimulation.[22] T cell exhaustion has been implicated to cause failures of active immunotherapy for solid tumors.

TILs require energy to eliminate tumor cells. Upon activation T cells enhance energy production through glycolysis,[34]. Glycolysis is less efficient than oxidative phosphorylation (OXPHOS), but provides building blocks for biomass formation and cell proliferation. Tumor cells also use glycolysis,[13] which may lead to glucose (Glu) depletion within the TME.[6,14] T cells with limited access to Glu have to rely on OXPHOS to produce energy. Although many substances including fatty acids (FAs) can fuel OXPHOS, it requires $O_2$, which can become limiting within tumors due to insufficient blood supply.[19] TILs therefore face dual metabolic jeopardy, which drives their functional exhaustion and thereby impairs the efficacy of cancer immunotherapy.

Thus, metabolism plays an important role in modulating T cell effector functions. How TILs adapt to the metabolic constraints within the TME, including glucose and oxygen deprivation, and how these constraints affect TIL ability to combat tumor progression remains poorly understood.

There remains a need in the art for new and effective tools and methods to facilitate treatment and prophylactic therapies for cancer.

SUMMARY OF THE INVENTION

In one aspect, a method for treating cancer comprises administering to a subject having a cancer characterized by a solid tumor a compound or reagent that promotes the use of fatty acid catabolism by tumor antigen-specific T cells in the tumor microenvironment (referred to variously as "a fatty acid catabolism promoter" or "fatty acid catabolism-promoting compound"). In another embodiment, this method involves co-administering a checkpoint inhibitor in the form of an antibody or a small molecule.

In another aspect, a method for treating cancer comprises administering to a subject having a cancer a T cell that is pretreated or conditioned ex vivo or in vitro with a compound or reagent that promotes the use of fatty acid catabolism rather than glucose for energy production by the pre-treated T cells.

In another aspect, a method for treating cancer comprises co-administering to a subject having a cancer characterized by a solid tumor an immunotherapeutic composition targeting an antigen or ligand on the tumor cell; and a compound or reagent that promotes the use of fatty acid catabolism by tumor antigen-specific T cells in the tumor microenvironment. In another embodiment, this method involves co-administering a checkpoint inhibitor in the form of an antibody or a small molecule.

In another aspect, a method for treating cancer comprises co-administering to a subject having a cancer characterized by a solid tumor an immunotherapeutic composition targeting an antigen or ligand on the tumor cell; and selected T cells pretreated ex vivo or treated upon transfer with a compound or reagent that promotes the use of fatty acid catabolism by tumor antigen-specific T cells to condition the T cell to use fatty acids rather than glucose for energy production prior to or upon adoptive cell transfer. In another embodiment, this method involves co-administering a checkpoint inhibitor in the form of an antibody or a small molecule.

In another aspect, a method for treating cancer comprises co-administering the immunotherapeutic composition, the fatty acid catabolism promoter and the selected T cells identified herein. In another embodiment, this method involves co-administering a checkpoint inhibitor in the form of an antibody or a small molecule.

In another aspect, a method for treating cancer comprises administering to a subject having a cancer a T cell that is pretreated ex vivo or in vitro with a compound or reagent that promotes the use of fatty acid catabolism by the T cells. The fatty acid catabolism promoting compound or reagent conditions the T cell to use fatty acids rather than glucose for energy production. This pretreatment and conditioning enhances the immune function of the T cell(s) once the T cell(s) are readministered, i.e., by adoptive therapy, to the subject. In another embodiment, this method involves co-administering a checkpoint inhibitor in the form of an antibody or a small molecule in combination with, or sequentially with, administration of the pre-treated, conditioned T cell. In another aspect, a method of modifying a T cell comprises pretreating the T cell ex vivo or in vitro with a compound or reagent that conditions the cell to use fatty acid catabolism for energy production by the T cells.

In another aspect, a method of enhancing the survival of a T cell, e.g., an autologous T cell, a chimeric antigen receptor-T cell, a chimeric endocrine receptor-T cell or ex vivo expanded tumor antigen-specific T cells comprising treating the T cell(s) ex vivo with a compound or reagent that promotes the use of fatty acid catabolism for energy production by tumor antigen-specific T cells in the tumor microenvironment before or upon adoptive cell transfer to a subject having a solid tumor.

In yet another aspect, a therapeutic regimen is provided for the treatment of cancer comprising administering to a subject having a cancer characterized by a solid tumor a single dose of an immunotherapeutic composition targeting an antigen or ligand on the tumor cell on a day 1 of treatment. In this regimen, the subject is thereafter administered a compound or reagent that promotes the use of fatty acid catabolism by tumor antigen-specific T cells in the tumor microenvironment. The first dose of the fatty acid catabolism-promoting compound of reagent begins on any of day 0, 1, 2, 3, 4 or 5 of treatment. Also involved in this regimen is the step of administering the fatty acid catabolism promoting compound or reagent daily from the beginning day of treatment of immunotherapeutic composition until a day occurring between day 7 to day 30 of treatment.

In still a further aspect, a composition is provided for adoptive transfer to a mammalian subject comprising a T cell that has been pretreated ex vivo or in vitro with a compound or reagent that conditions the cell to use fatty acid catabolism for energy production by the T cells.

Other aspects and advantages of these compositions and methods are described further in the following detailed description of the preferred embodiments thereof.

BRIEF DESCRIPTION OF THE DRAWINGS

FIG. 2A illustrates MFI values (mean-SEM) of mitochondrial membrane potential (MMP) and mitochondrial reactive oxygen species (MROS) stains in Trp-1- and E7-specific CD8+ T cells from spleens and tumors harvested 2 weeks or 1 month after challenge (n=5 mice/group, representative of 3 experiments). MMP allows for formation of proton gradients used for ATP synthesis by OXPHOS. MROS is a superoxide highly toxic byproduct of OXPHOS mainly generated by complex I and III of the mitochondrial electron transport chain.

FIG. 2B shows a bar graph reporting results of quadrant gating of frequencies of Trp-1- and E7-specific CD8+ T cells with high or low levels of MMP and MROS from mice bearing 1-mo tumors or CD44– T cells. (–) not significant or (*) significant shown above the bars in the graph are arranged so that the $1^{st}$ to $4^{th}$ bars show differences between MMP$^{hi}$MROS$^{lo}$ cells, MMP$^{hi}$MROS$^{hi}$ cells, MMP$^{lo}$MROS$^{hi}$ cells and MMP$^{lo}$MROS$^{lo}$ cells, respectively.

FIG. 2C illustrates MFI (mean-SEM) of HIF-1α and Glut1 expression in/on specific Trp-1- and E7-specific CD8+ T cells from spleens and tumors of mice bearing 1-mo tumors (n=5/group, representative of 2 assays). All bar graphs show mean-SEM. Representative histograms for samples from spleen and tumor were compared (data not shown).

FIG. 3A shows in the left bar graph the MFI (mean-SEM) values of HIF-1α expression in/on Trp-1-specific CD8$^+$TILs transduced with control (co RNA) or HIF-1α shRNA (shRNA) vector. The right two bar graphs show the MFI (mean-SEM) values of co-inhibitors PD-1 (left) and LAG-3 (right) expression by Trp-1-specific CD8$^+$TILs transduced with control (co RNA) or HIF-1α shRNA (shRNA) vector. Representative histograms for samples transduced with control or HIF-1α shRNA vector were compared (data not shown). HIF-1α correlates with co-inhibitor LAG-3 expression in vitro and in vivo.

FIG. 3B illustrates % of MAA-specific CD8+TILs transduced with control (co RNA) or HIF-1α shRNA (shRNA) expressing vectors producing individual factors, GzmB, IFN-γ or Perforin (from left to right). All bar graphs show mean-SEM.

FIG. 3C is a bar graph illustrating % of lentivector transduced cells producing 3, 2 or 1 (from top to bottom of each bar) of the factors (n=5-7 mice/group). * within ( ) indicates significant difference in sum of responses, * out of ( ) left to right: significant difference in 3, 2, 1 functions. All bar graphs show mean-SEM. HIF-1α knock-down increases CD8+TIL functions.

FIGS. 4A-4I show that limited access to Glu and oxygen forces activated CD8+TILs to enhance FA catabolism. In late stage melanoma, glucose and oxygen become limiting.

FIG. 4A is a bar graph showing Glu concentrations in plasma and interstitial fluid of tumors (n=3/group). Data are shown as mean-SEM.

FIG. 4B shows relative transcript levels in CD8+ T cells stimulated in Gal or Glu+2-DG medium in comparison to those of CD8$^+$ T cells cultured in Glu medium under hypoxia in the upper two rows (n=3-4 samples/group). In the middle 2 rows, relative transcript levels are shown for Trp-1- and E7-specific CD8+TILs from 1-mo-old tumors compared to CD8$^+$TILs of the corresponding antigen specificity from 2 week-old tumors (n=4-5 samples/group). Lower 2 rows show relative transcript levels for Trp-1- and E7-specific CD8+ T splenocytes harvested 3 mo vs. 2 wk after vaccination. Line code shown to the right of the map compares changes in transcript levels between in vitro and in vivo samples. Transcripts involved in lipid metabolism are enhanced in metabolically stressed T cells in vitro and in vivo.

FIG. 4C is a bar graph showing the intensity of glycolysis metabolites in CD44$^+$CD8$^+$TILs from 1 month-old tumors compared to those of CD44$^+$CD8$^+$TILs from 2-week old tumors. Experiments were conducted twice with 2-3 pooled samples collected from ~30 mice/sample/experiment. Data are shown as mean values.

FIG. 4D shows $^{13}C_6$-Glu contribution to TCA cycle metabolites in CD44$^+$CD8$^+$TILs from mice bearing 1-mo tumors normalized to those from 2-wk tumors (left) or spleens of the same mice harvested at 1 mo after challenge (right). Experiments were conducted twice with 2-3 pooled samples collected from ~30 mice/sample/experiment. Data are shown as mean values.

FIG. 4E shows the intensity of FA metabolites in CD44$^+$ CD8$^+$TILs from 1 month-old tumors compared to those of CD44$^+$CD8$^+$TILs from 2-week tumors. Experiments were conducted twice with 2-3 pooled samples collected from ~30 mice/sample/experiment. Data are shown as mean values.

FIG. 4F are three bar graphs showing normalized $^{13}C_{16}$-palmitate contribution to TCA cycle metabolites in CD44$^+$ CD8$^+$ T cells from 1-mo vs. 2-wk tumors (left) or 1-mo tumors vs. 1-mo spleens (middle) or spleens at 1 mo vs. 2 wk after tumor challenge (right). Experiments were conducted twice with 2-3 pooled samples collected from ~30 mice/sample/experiment. Data are shown as mean values.

FIG. 4G is a bar graph showing relative intensity of free FA species in the tumor interstitial fluid shown as ratio of results obtained from 1-mo over 2-wk tumors (n=2-3 samples/group). Data are shown as mean-SEM.

FIG. 4H is a graph showing uptake of a boron-dipyrromethene fluorescent dye (Bodipy) $C_{16}$ by freshly isolated Trp-1- or E7-specific CD8$^+$ T cells from spleens or tumors harvested 2 weeks or 1 month after tumor challenge tested directly ex vivo n=5/group. Representative histograms for samples from spleen and tumor harvested 1 month after tumor challenge were compared (data not shown). Lines with * above bars indicate significant differences. Data are shown as mean-SEM.

FIG. 4I shows a bar graph represented MFI for Cpt1a in Trp-1- and E7-specific CD8$^+$ T cells from spleens or tumors harvested 2 weeks or 1 month after tumor challenge. Representative histogram are not shown. n=5/group. Lines with * above bars indicate significant differences. Data are shown as mean-SEM. FA catabolism is enhanced in CD8+TILs during tumor progression.

FIG. 5A shows the MFI of PD-1 and pAkt on/in specific CD8+TILs at 1 mo after tumor challenge. n=5-7 mice/group, Data is shown as mean-SEM.

FIG. 5B shows MFI of markers (CD62L, CD127 and Eomes, panels from left to right) on/in specific CD8$^+$TILs from 1-mo tumors. n=5-7 mice/group. Data is shown as mean-SEM.

FIG. 5C shows a $^{13}C_{16}$-palmitate contribution to TCA cycle metabolites in CD44$^+$CD8$^+$ T cells from $\alpha$-PD-1 treated (dark grey) normalized to iso-treated 1-mo tumors (light grey). n=2-3 samples/group. Each sample is pooled from 20-30 mice. Data is shown as mean values.

FIG. 5D shows the intensity of ketone bodies in CD44$^+$ CD8$^+$ T cells from $\alpha$-PD-1 treated (dark grey) compared to iso-treated 1-mo tumors (light grey). n=2-3 samples/group. Each sample is pooled from 20-30 mice. Data is shown as mean values.

FIG. 5E shows $^{13}C_6$-Glu contribution to TCA cycle metabolites in CD44$^+$CD8$^+$ T cells from $\alpha$-PD-1 treated (dark grey) normalized to iso-treated 1-mo tumors (light grey). n=2-3 samples/group. Each sample is pooled from 20-30. Data is shown as mean values. These results show that PD-1 blockade does not affect CD8+TILs' metabolism.

FIG. 5F shows frequencies of specific CD8$^+$TILs from 1-mo tumors of mice treated with iso or $\alpha$-PD-1 producing 3, 2 or 1 factors (from top to bottom of each bar). n=11-15 mice/group. Data is shown as mean-SEM.

FIG. 6A is a cartoon of an experimental setup of the in vivo study showing drugs that target different pathways of FA catabolism.

FIG. 6B are bar graphs showing MFI of markers (PD-1, T-bet, CD62L, Cd127, KLRG1 and total FoxO1, panels from left to right) on/in donor CD8+ T cells from mice treated with diluent (Dil.) or FF before transfer. n=8-10/group. Data is shown as mean-SEM.

FIG. 6C is a bar graph showing functions of CD8$^+$ T cells from spleens of donor mice treated with Dil. or FF before transfer as % of cells producing 3, 2 and 1 factors (from top to bottom of each bar). n=8-10/group. Data is shown as mean-SEM.

FIG. 6D is a bar graph showing basal OCR of CD8+ T cells from spleens of donor mice fed with Dil. or FF. Some samples were incubated with Etomoxir (Eto) (n=5-6 mice/group). Data is shown as mean-SEM.

FIG. 6E is a bar graph showing MFI of PD-1 on Dil.- or FF-treated donor CD8+TILs (n=6/group). Data is shown as mean-SEM.

FIG. 6F is a bar graph showing % specific CD8+TILs from Dil.- or FF treated donors producing 3, 2, or 1 factors (from top to bottom of each bar). (–) or (*) on top of each bar indicates significant differences in sum of the responses. * from bottom to top: differences in producing 1, 2 or 3 factors. Data is shown as mean-SEM.

FIG. 6G is a graph showing the tumor weight 2 weeks after cell transfer (n=5/group). Data is shown as mean±SEM.

FIG. 6H is a cartoon of an experimental design of PD-1 blockade combined with transfer of FF- or Dil.-treated T cells.

FIG. 6I is a graph showing tumor progression indicated as tumor volume in mice that received either FF- or Dil.-treated cells and either iso or $\alpha$-PD-1 treatment after cell transfer. n=6-7/group. Data is shown as mean±SEM.

FIG. 6J is a set of bar graphs showing PD-1 expression on donor-derived FF- or Dil.-treated CD8$^+$TILs recovered from recipients treated with iso or $\alpha$-PD-1. n=6-7/group. Data is shown as mean-SEM.

FIG. 7A is a cartoon showing experimental setup for the in vivo study.

FIG. 7B is MFI of PD-1 expression on wt and PPAR-$\alpha$ KO donor Trp-1- and E7-specific CD8$^+$TILs (n=6/group, representative of 2 assays). Data is shown as mean-SEM. Decreasing FA catabolism reduces PD-1 expression.

FIG. 7C shows the % of Trp-1- and E7-specific CD8$^+$TILs from the two groups of donor mice producing 3, 2, and 1 factors (from top to bottom of each bar). * outside of (indicates differences producing 1-3 functions (bottom to top). * within ( ) indicates differences in overall frequencies. Flow blots illustrating functions of donor-derived Trp-1- and E7-specific CD8+TILs from each group are not shown. n=6/group. Data is shown as mean-SEM. Decreasing FA catabolism dampens CD8+TIL functions.

FIGS. 8A-8H show that hypoxia affects CD8+ T cell metabolism, differentiation and functions.

Figure 8A:
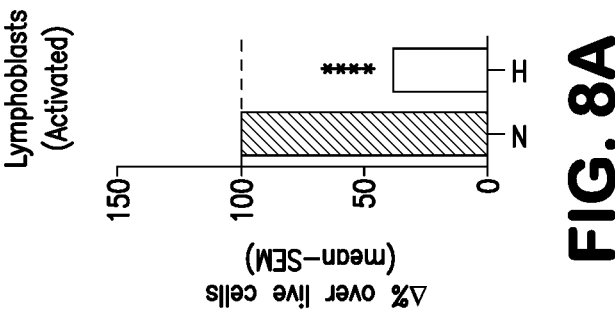

FIG. 8A illustrates lymphoblast formation; normalized change of % of activated live CD8+ T cells forming blasts by day 4 of culture under hypoxia (H, lightgrey) compared to those cultured under normoxia (N, dark grey). * on top of each bar indicates significant differences compared to values obtained from samples cultured in Glu medium under normoxia. (n=4-5 samples/group, representative of 3-5 experiments). Data is shown as mean-SEM.

FIG. 8B shows normalized change of MFI values for HIF-1α and Glut1 expression (stains) in/on activated CD8+ T cells cultured under normoxia, N or hypoxia, H (n=4-5 samples/group, representative of 3-5 experiments). * on top of each bar indicates significant differences compared to values obtained from samples cultured in Glu medium under normoxia. Data is shown as mean-SEM.

FIG. 8C are graphs showing basal OCR (left) and ECAR (right) rate of day 4 activated CD8+ T cells cultured under normoxia (N) or hypoxia (H). (n=4-5/condition, representative of 3-5 experiments). Data is shown as mean-SEM.

Figure 8E:
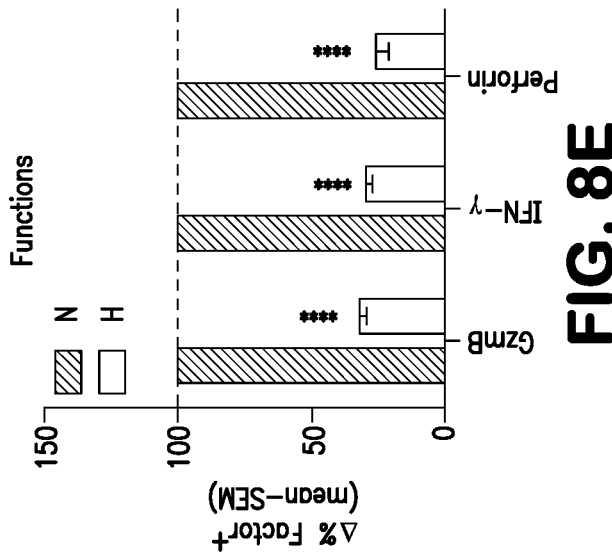
Figure 8D:
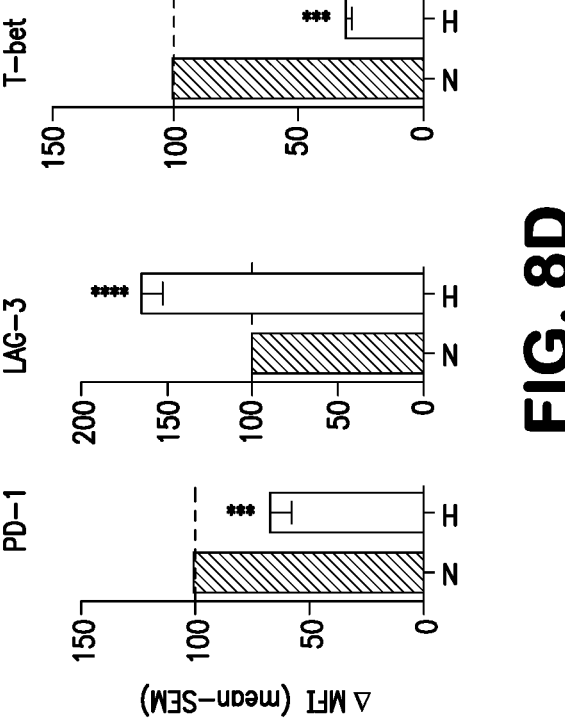

FIG. 8D shows normalized change of MFI of PD-1, LAG-3 and T-bet (from left to right) in/on activated cells (n=4-5/condition, representative of 3-5 experiments). Data is shown as mean-SEM.

FIG. 8E shows production of individual functions of activated cells cultured under hypoxia (H) with data normalized to normoxia (N). Functions of CD8+ T cells shown as change of % of CD8+CD44+ T cells producing IFN-γ, GzMB and perforin factors (their representative flow plots are not shown). (n=4-5/condition, representative of 3-5 experiments). Data is shown as mean-SEM.

Figure 8G:
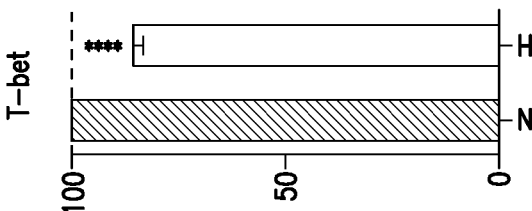
Figure 8G:
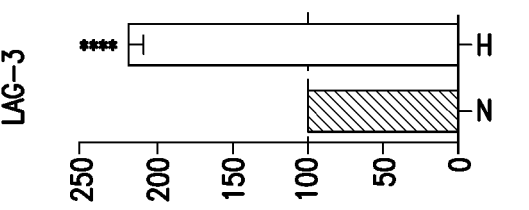
Figure 8G:
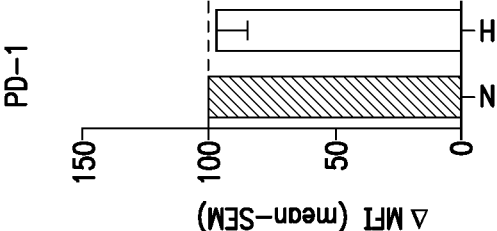
Figure 8F:
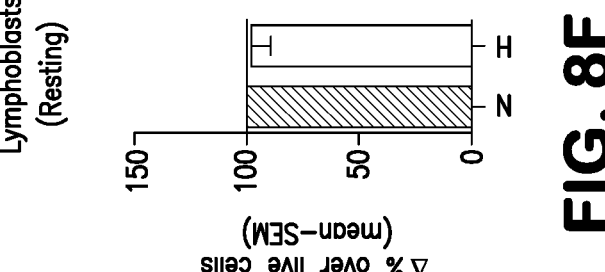

FIG. 8F shows blast formation; normalized % change of live IL-2 maintained resting CD8+ T cells forming blasts under hypoxia (H, white) compared to those cultured under normoxia (H, gray) (n=3-4 samples/group, representative of 2 experiments). Data is shown as mean-SEM.

FIG. 8G shows normalized expression change of PD-1, LAG-3 and T-bet on/in IL-2 maintained resting cells subjected to hypoxia (H, white) compared to those cultured under normoxia (N, grey). n=6/condition, representative of 2 experiments. * above bars indicate significant differences between samples kept under normoxia and those subjected to hypoxia. Data is shown as mean-SEM.

Figure 8H:
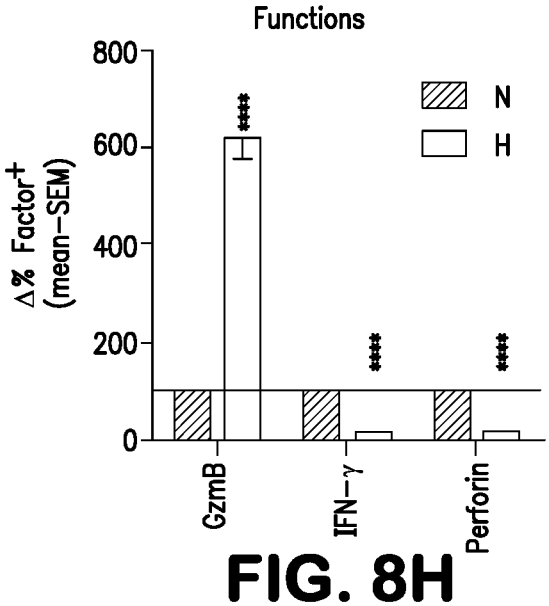

FIG. 8H shows production of individual factors by IL-2 maintained resting CD8+ T cells cultured under hypoxia (H, white) compared to those cultured under normoxia (N, grey). % change of IL-2 maintained resting CD8+ T cells producing IFN-γ, GzMB and perforin were quantified. Data is shown as mean-SEM.

FIG. 9A-9E show the effects of glucose limitation on metabolism, differentiation and effector functions of CD8+ T cells activated in vitro under normoxia (N) or short-term hypoxia (H). Indicated (in Y-axis title) values are normalized to those obtained with Glu cultures kept at normoxia, which are set at 100 (dotted black lines). The stippled light gray lines show results for cells cultured in Glu and subjected to hypoxia normalized to results for cells cultured in Glu and under normoxia. Galactose/2-Deoxy-D glucose (2-DG) mimics lack of glucose. All data are shown as mean-SEM.

Figure 9A:
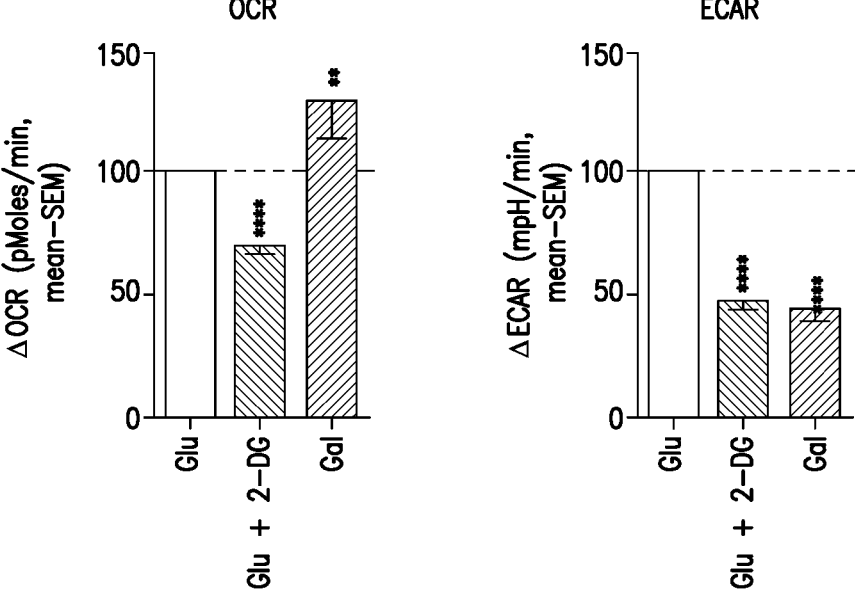

FIG. 9A shows normalized basal OCR change (right panel) and extracellular acidification rate (ECAR) change (left panel) for CD8+ T cells stimulated in regular Glu-rich medium, Glu with 2-DG, or medium supplemented with Gal instead of Glu for 4 days. (n=4 samples/group, pooled from 20-30 mice/experiment and representative of 3 experiments).

Figure 9D:
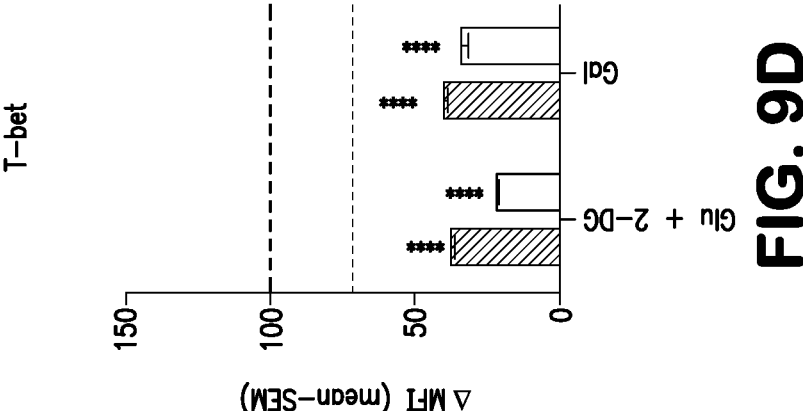
Figure 9C:
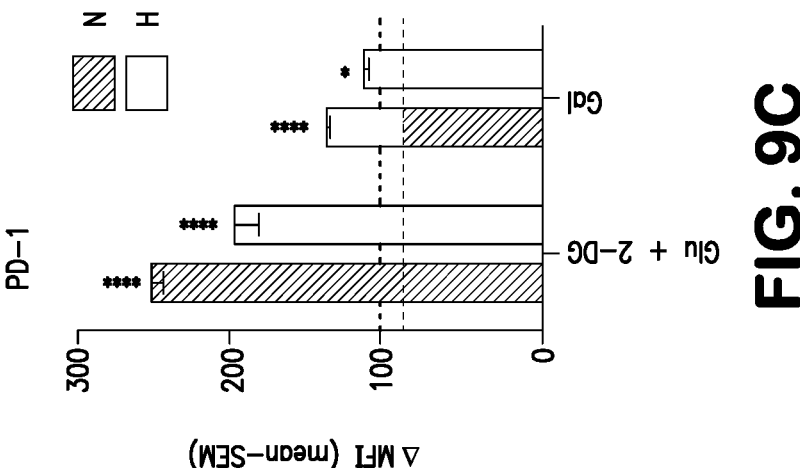
Figure 9B:
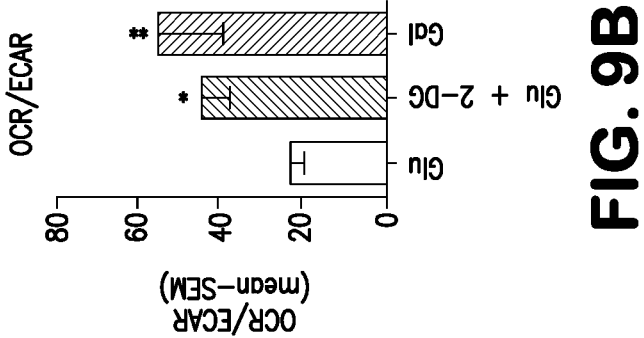

FIG. 9B shows the OCR to ECAR ratios at baseline for CD8+ T cells stimulated in regular Glu-rich medium, Glu with 2-DG, or medium supplemented with Gal instead of Glu for 4 days. (n=4 samples/group, pooled from 20-30 mice/experiment and representative of 3 experiments). Lack of glucose increases the OCR/ECAR ratio.

FIG. 9C show normalized changes of MFI values for PD-1 expression on CD8+ T cells activated under normoxia (N, dark grey) or hypoxia (H, light grey) (n=4-5/condition, representative of >5 assays). Lack of glucose increases PD-1 expression. Representative histograms are not shown.

FIG. 9D show normalized changes of MFI values of T-bet (n=4-5, representative of >3 assays).

Figure 9E:
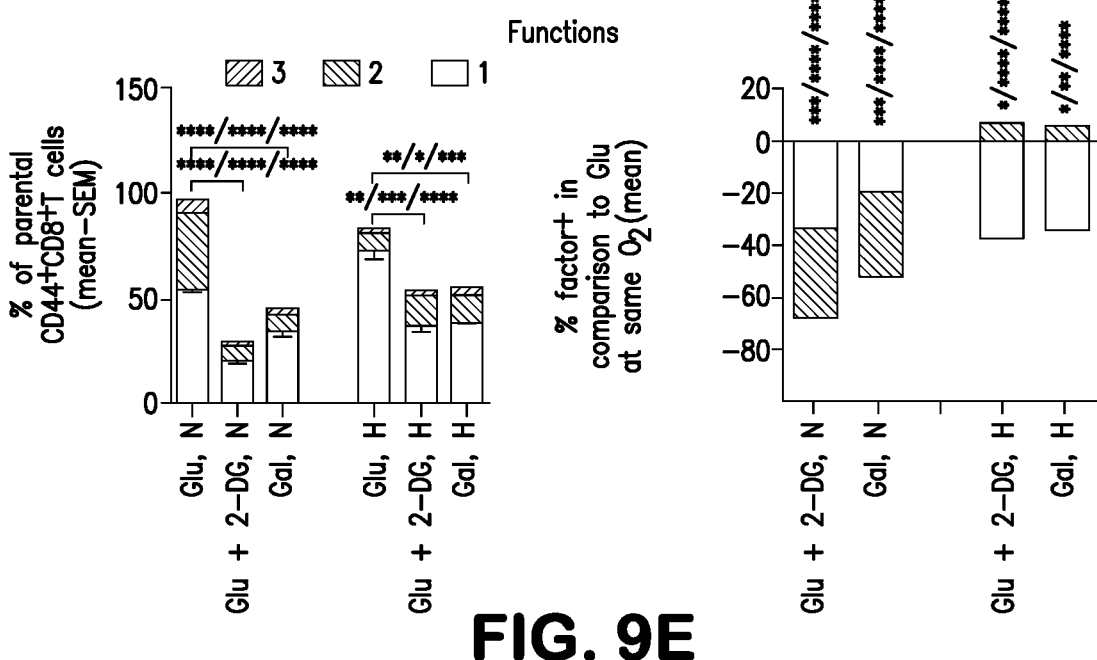

FIG. 9E shows Left: % of cells producing 3, 2 and 1 factors (from top to bottom of each bar) over all CD44+ CD8+ T cells cultured under different conditions (N, normoxia; H, hypoxia). Right: Same data as left illustrating differences in % of cells producing 3, 2 and 1 factors (from bottom to top for the left two bars and from top to bottom for the right two bars) in Glu+2-DG or Gal medium compared to those of cells in Glu medium with the corresponding O₂ supply. Statistics on each bar indicates difference in % of cells producing 3, 2 and 1 function (bottom to top). Representative flow plots for IFN-γ and GzmB production are not shown. Lack of glucose reduces CD8+ T cell functions under normoxia and less pronounced under hypoxia.

FIGS. 10A-10E show the effects of glucose and O₂ limitation on FA catabolism of CD8+ T cells activated in vitro. All data are shown as mean-SEM.

Figure 10A:
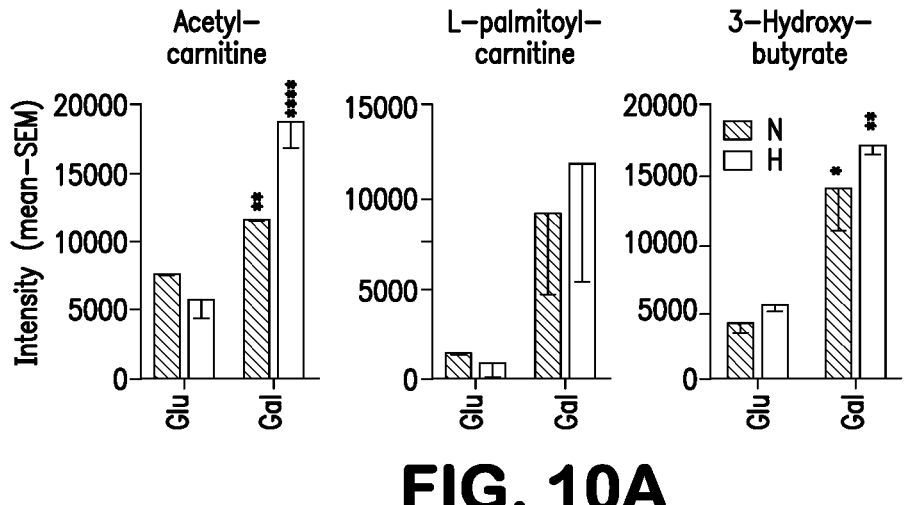

FIG. 10A shows the relative intensity of fatty acid catabolism-related metabolites in CD8+ T cells stimulated for 4 days in vitro under different conditions. Normoxia (N, dark gray); Hypoxia (H, light grey); compared to those of cells cultured under Glu, N (enriched CD8+ T cells were pooled from 20-30 mice for each experiment, representative of 2 assays).

Figure 10B:
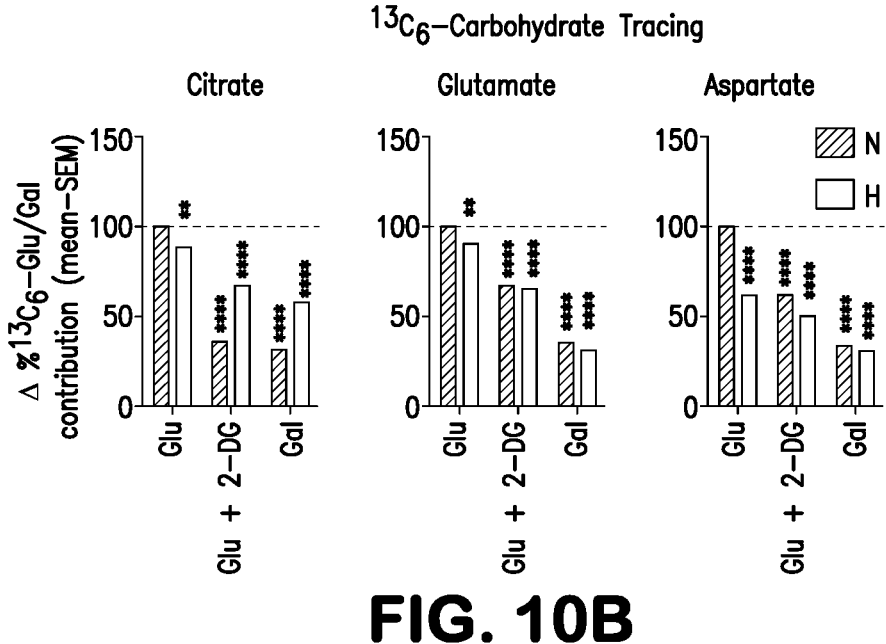

FIG. 10B shows normalized contribution change of $^{13}C_6$-Glu/Gal-derived $^{13}C$ carbon to metabolites of the TCA cycle in cells cultured in different media under different conditions (Normoxia, N, dark gray; Hypoxia, H, light grey) compared to those cultured in Glu medium under normoxia, N (set as 100, indicated by dotted line). Data are shown as relative mean % change of labeling (enriched CD8+ T cells were pooled from 20-30 mice for each experiment, representative of 2 assays). (*) on top of each bar indicates significant differences compared to cells cultured under Glu, N.

Figure 10C:
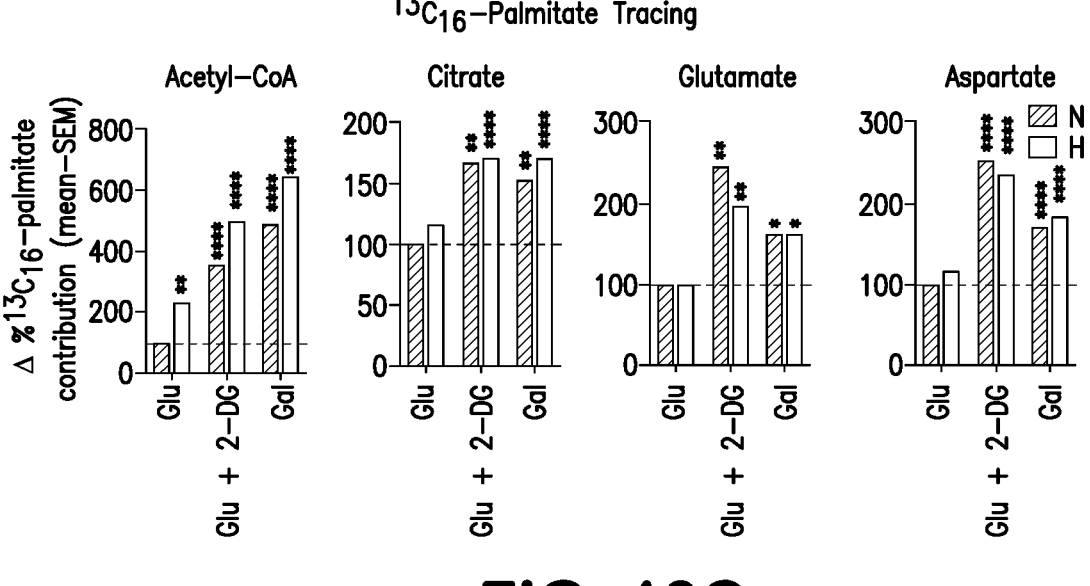

FIG. 10C shows normalized contribution change of $^{13}C_6$-palmitate-derived $^{13}C$-carbon to metabolites of the TCA cycle in cells cultured in different media under different conditions (Normoxia, N, dark gray; Hypoxia, H, light grey) comparing to those cultured under Glu, N (set as 100, indicated by dotted line). Data are shown as relative mean % change of labeling (enriched CD8+ T cells were pooled from 20-30 mice for each experiment, representative of 2 assays). (*) on top of each bar indicates significant differences compared to cells cultured under Glu, N. More FA-derived carbon contributes to TCA metabolites and amino acids indicating enhanced use of FA for ATP and biomass production under hypoglycemia and hypoxia.

Figure 10E:
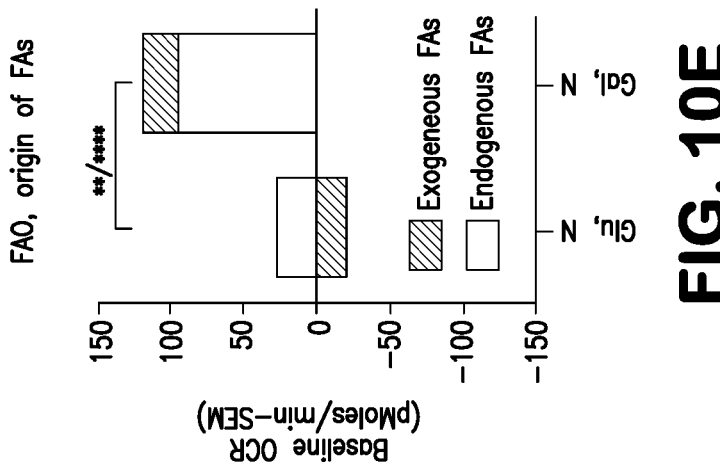
Figure 10D:
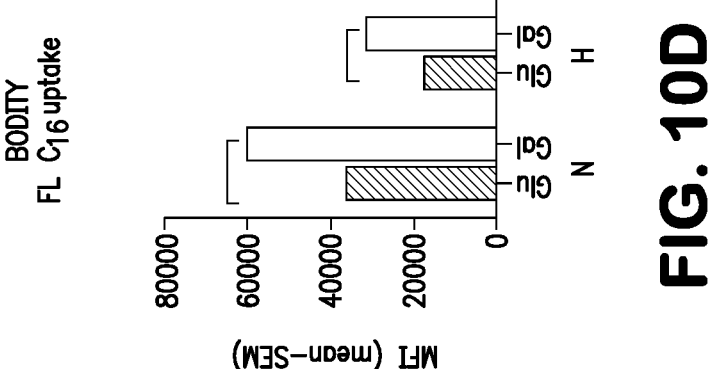

FIG. 10D illustrates the uptake of Bodipy FL $C_{16}$ (fluorescent free FA) by cells cultured in Glu (dark gray) or Gal (light gray) media under normoxia (N) or hypoxia (H). Histograms of representative samples subjected to hypoxia are not shown. (n=5/group, representative of two experiments).

FIG. 10E shows basal OCR of FAO due to consumption of exogenous (dark gray bars) and endogenous (light gray bars) FAs by CD8+ T cells stimulated in vitro in Glu or Gal media (n=3 samples, pooled from 15 mice/group). FA catabolism increases when glucose is limiting.

FIGS. 11A-11D show that anti-PD-1 treatment affects tumor cell metabolism, i.e., increasing Glu concentration in the tumor interstitial fluid and the tumor cells' Glu metabolism.

Figure 11A:
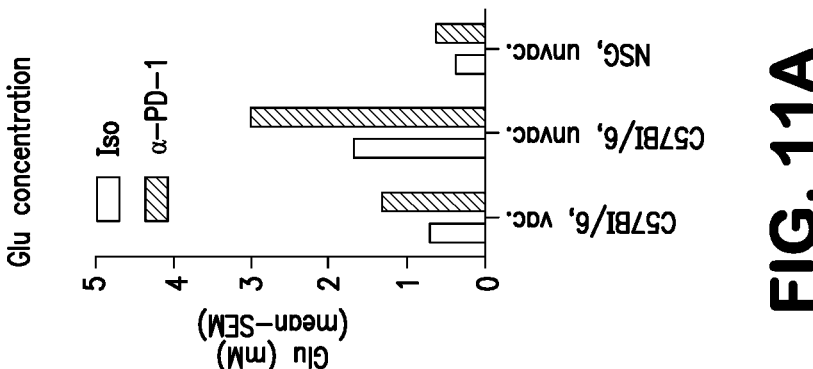

FIG. 11A is a bar graph showing that Glu concentration in the tumor interstitial fluid from the indicated mice that had received the isotype control (Iso, white) or the anti PD-1 antibody (α-PD-1, grey). Data is shown as mean-SEM.

Figure 11B:
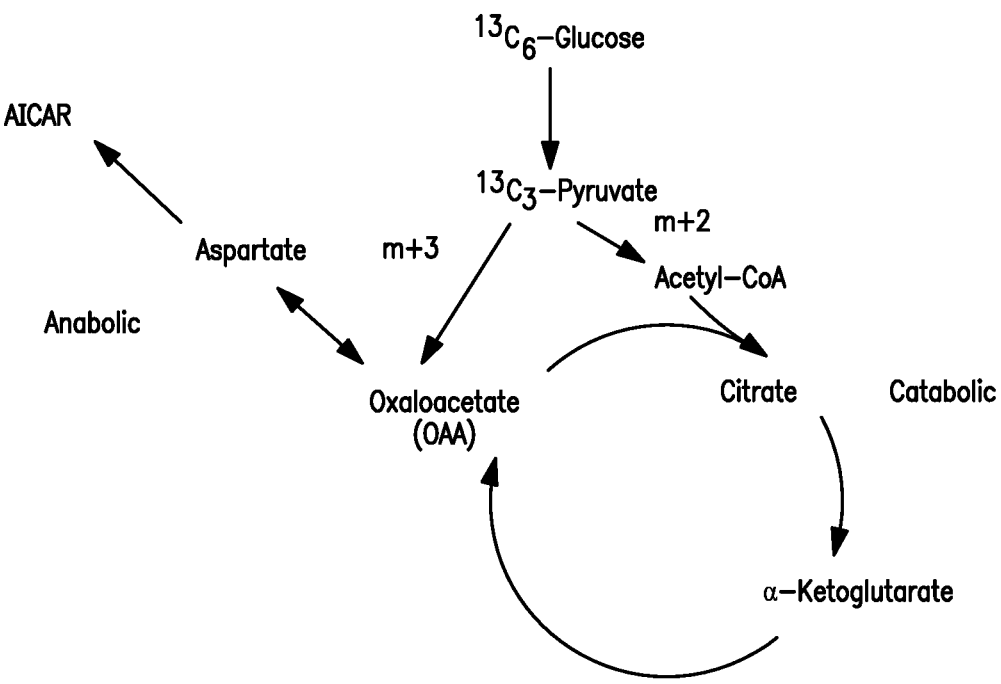

FIG. 11B is a schematic that illustrates the $^{13}C_6$-glucose metabolism of tumor cells using catabolic pathway by contributing two $^{13}C$ carbons to citrate and TCA cycle intermediate, α-ketoglutarate, or using anabolic pathway by contributing three $^{13}C$ carbons to oxaloacetate and citrate and the purine synthesis pathway intermediate AICAR.

Figure 11C:
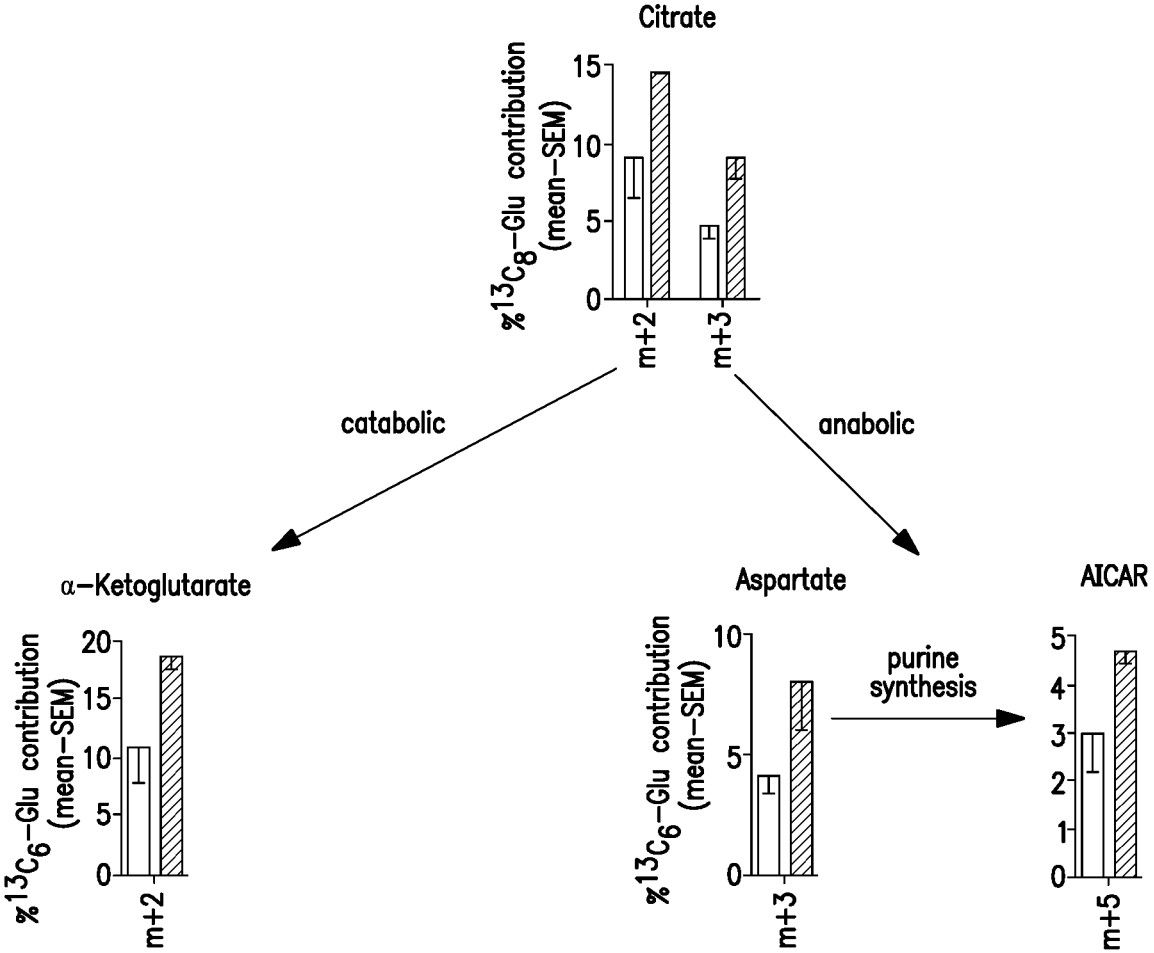

FIG. 11C illustrates three bar graphs showing the results for $^{13}C_6$-Glu tracing of cells isolated from day 20 tumors of NSG mice. Incorporation of 2 and 3 carbons are shown indicating the use of Glu for catabolic or anabolic downstream reactions. Data is shown as mean-SEM.

Figure 11D:
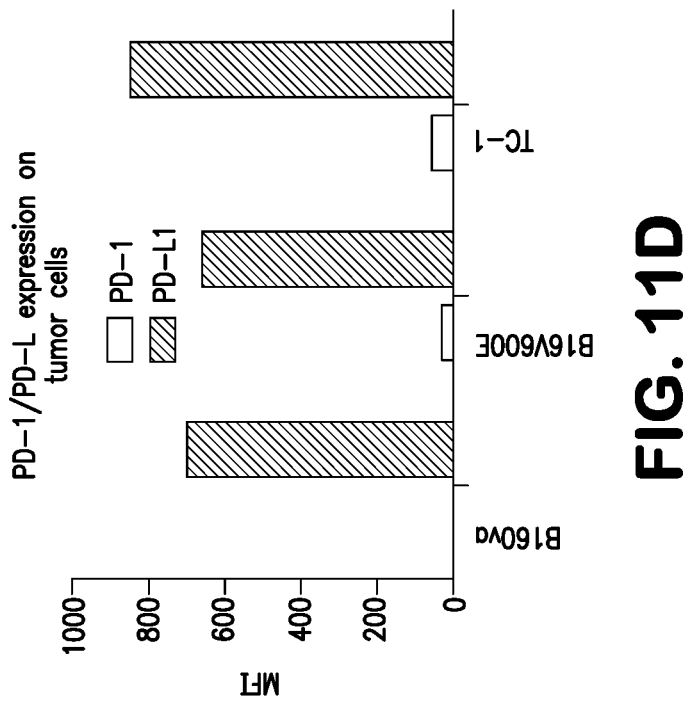

FIG. 11D is a bar graph reporting the MFI of PD-1 (grey) and PD-L1 (black) expression on the identified tumor cells. Ligation of PD-1 to PD-L1 on tumor cells increases their resistance to apoptosis or T cell mediated cytolysis.

FIGS. 12A-12D illustrate that manipulating FA metabolism of activated CD8$^+$ T cells in vitro affects their differentiation and functions.

Figure 12A:
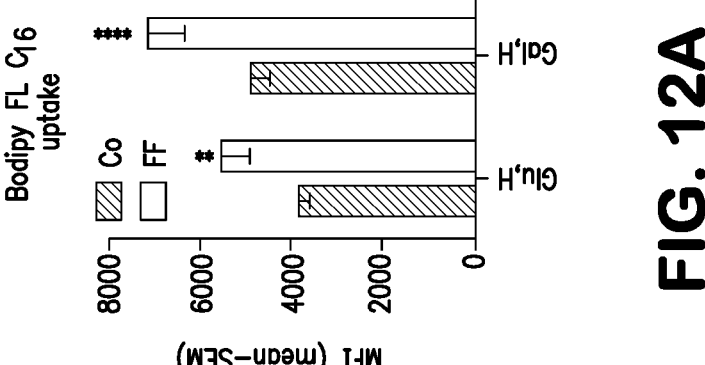

FIG. 12A shows Bodipy $C_{16}$ uptake by CD8+ T cells stimulated in vitro in Glu or Gal and subjected to short-term hypoxia (H) with the addition of FF (FF, light grey) compared to those of cells cultured under same condition with the addition of diluent (Co, dark grey). * above bars indicate significant differences between cells treated with FF and diluent; histograms of representative samples are not shown. (n=5 samples/condition, representative of 2 experiments). Data is shown as mean-SEM.

Figure 12D:
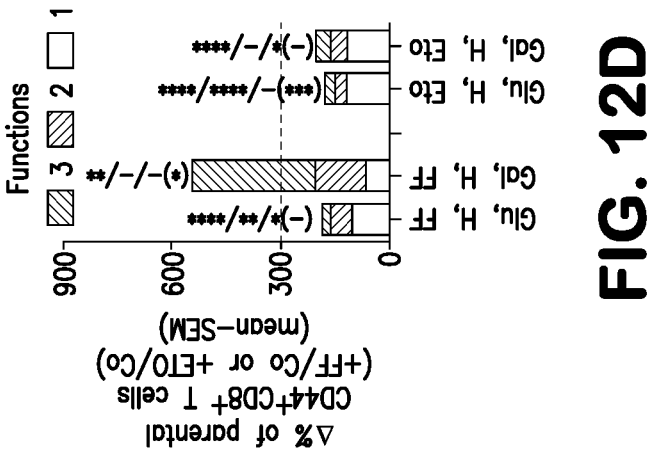
Figure 12C:
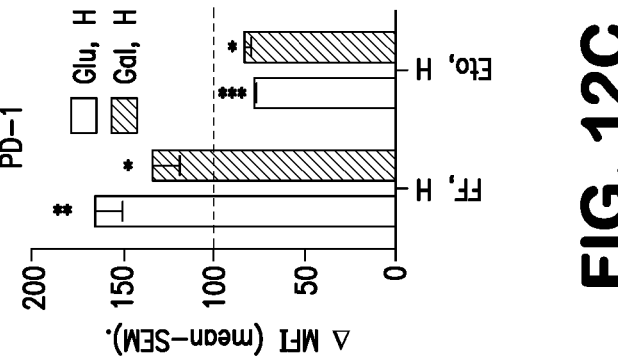
Figure 12B:
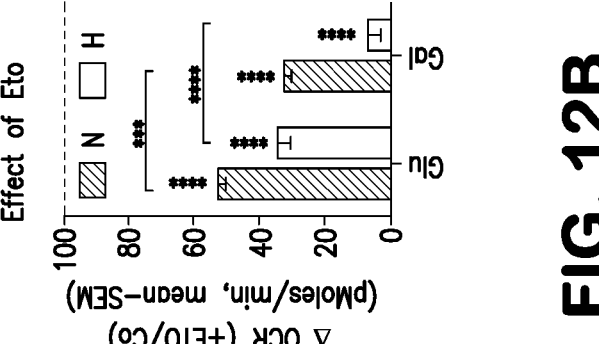

FIG. 12B shows the relative basal OCR change of CD8+ T cells cultured with Etomoxir (Eto) in Glu or Gal medium under normoxia (N) or hypoxia (H) normalized to cells cultured with diluent under same condition (set as 100, indicated by dotted line). * above each bar indicate significant differences between Eto- and diluent-treated cells. Lines with * above show differences between the connected samples. n=9 samples/condition, representative of 2 experiments. Eto inhibits lipid metabolism.

FIG. 12C shows a bar graph, the effects of FF or Eto on PD-1 expression change of CD8+ T cells stimulated in Glu (light grey bars) or Gal (dark grey bars) medium and subjected to hypoxia (H, n=4-6/group, representative of >3 experiments). Data are shown as relative MFI change for PD-1 stains on cells treated with FF or Eto normalized to the MFI change of PD-1 stains on cells treated with diluent under the same conditions (N set at 100, stippled black line). * on top of bars indicates significant differences between cells treated with FF or Eto and with diluent. Histograms of PD-1 expression on representative samples are not shown.

FIG. 12D shows a bar graph with normalized % change of CD44+CD8+ T cells producing 3, 2 or 1 factors (from top to bottom of each bar). Functions of cells treated with FF or Eto are normalized to those of cells treated with diluent (set at 300, stippled line; n=5/group, representative of 3 assays/group). (*): significant differences of total responses between cells treated with drug or diluent. * outside of ( ): significant differences in change of % of 1, 2 and 3 factors (bottom to top). Representative flow plots show levels of factors. All data are shown as mean-SEM.

Figure 13A:
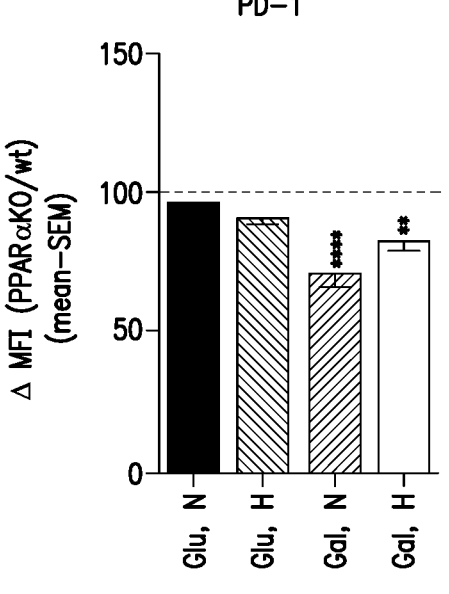
Figure 13B:
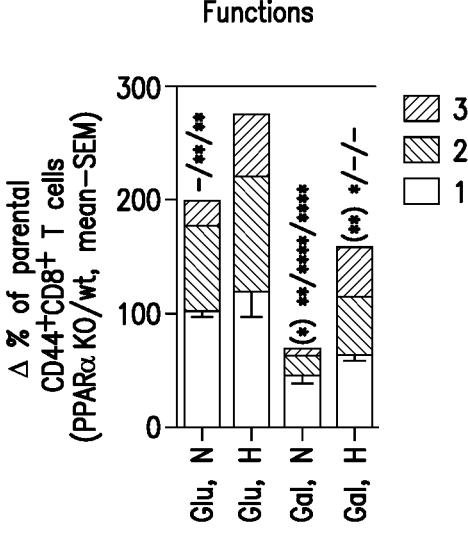

FIGS. 13A-13B show reducing FA metabolism of activated CD8+ T cells under metabolically challenging conditions in vitro reduces their PD-1 expression and effector functions.

FIG. 13A shows normalized change of MFI values for PD-1 stains on PPAR-α KO CD8+ T cells cultured under different conditions compared to those of wt CD8+ T cells (n=4-5/condition). * Indicates significant difference between wt and PPAR-α KO CD8+ T cells. Data are normalized to results with wt cells cultured under the same conditions and set at 100. Normoxia, N; Hypoxia, H. All data are shown as mean-SEM.

FIG. 13B shows normalized change of % of PPAR-α KO CD8+ T cells producing 3, 2 and 1 factors (from top to bottom of each bar) compared to those of wt CD8+ T cells (n=5/condition).

Figure 14A:
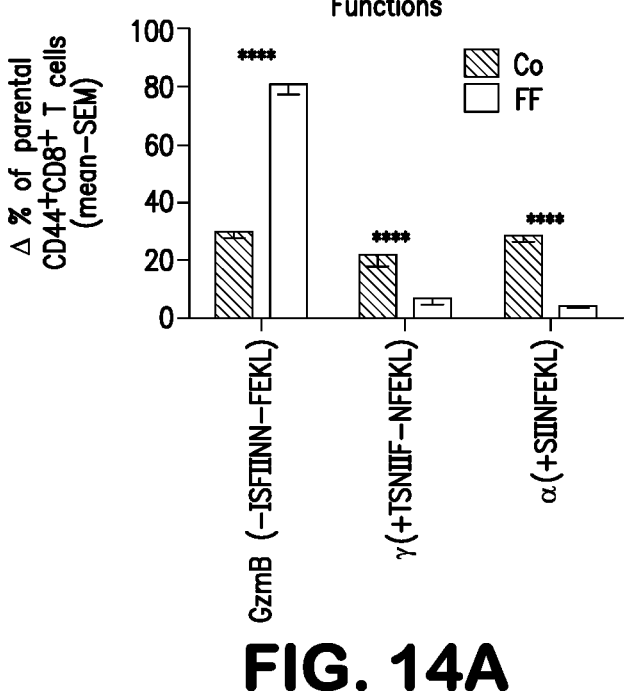
Figure 14B:
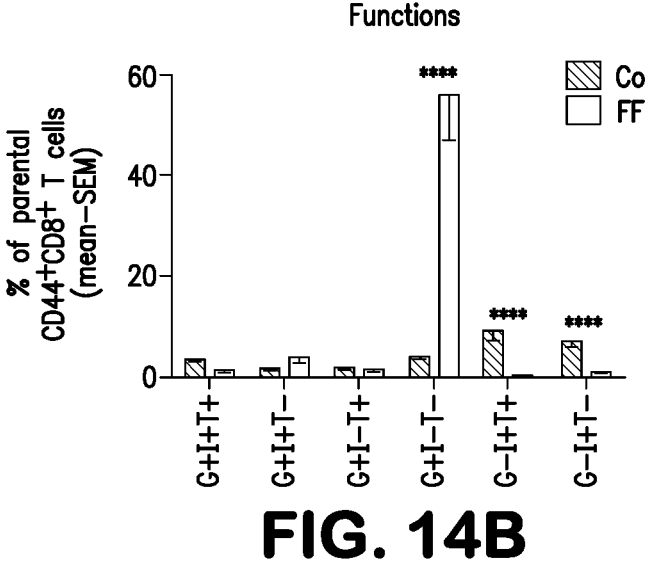
Figure 14C:
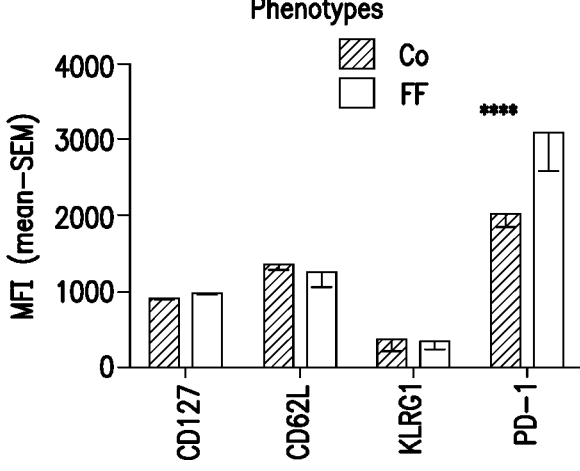

FIGS. 14A-14C show the effect of fenofibrate treatment during in vitro stimulation of OT-1 cells (a cancer model) and the effects on cell functions and phenotypes.

FIG. 14A shows the effects of cell function based on % of parental CD44+CD8+ T cells (Mean-SEM) in a mouse model B14-SIINFEKL using OT-1 cells transgenic for SIINFEKL-specific TCR. Measurements are taken individually for the GzmB, IFN-γ (γ) and TNF-α (α) in control (Co, first bars under each condition) and FF-treated cells (FF, second bar under each condition).

FIG. 14B is a graph showing the same measurement on the combination of the GzmB, IFN-γ and TNF-α. Control, Co, first bars under each condition; FF-treated cells, FF, second bar under each condition.

FIG. 14C is a graph showing effect on phenotypes, measured as MFI (mean-SEM) for the antigens CD127, CD62L, KLRG1 and PD-1. Control, Co, first bars under each condition; FF-treated cells, FF, second bar under each condition. These data show that FF treatment operates in cancers other than melanoma, and without administration of a specific vaccine used to induce T cell proliferation.

FIGS. 15A-15F show FF treatment during in vitro stimulation of OT-1 cells.

Figure 15A:
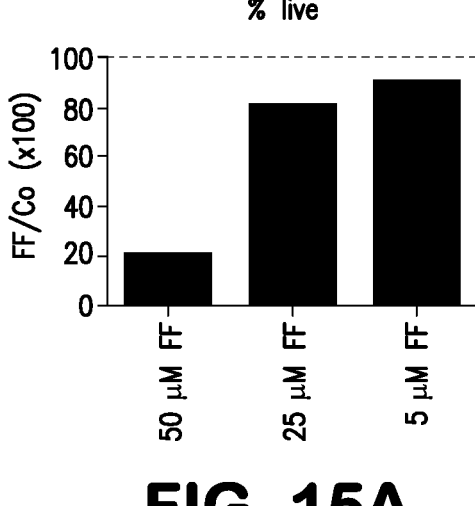

FIG. 15A is a bar graph showing the effect of various concentration of FF on proliferation.

Figure 15B:
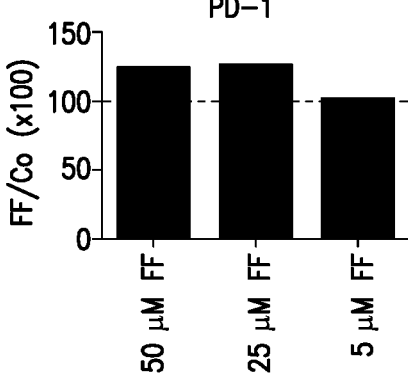

FIG. 15B is a bar graph showing the effect of various concentration of FF on PD1.

FIG. 15C is a bar graph showing the effect of various concentration of FF on Bodipy C16.

FIG. 15D is a bar graph showing the effect of various concentration of FF on Cpt-a.

FIG. 15E is a bar graph showing the effect of various concentration of FF on PPARα.

Figures 15F, 16:
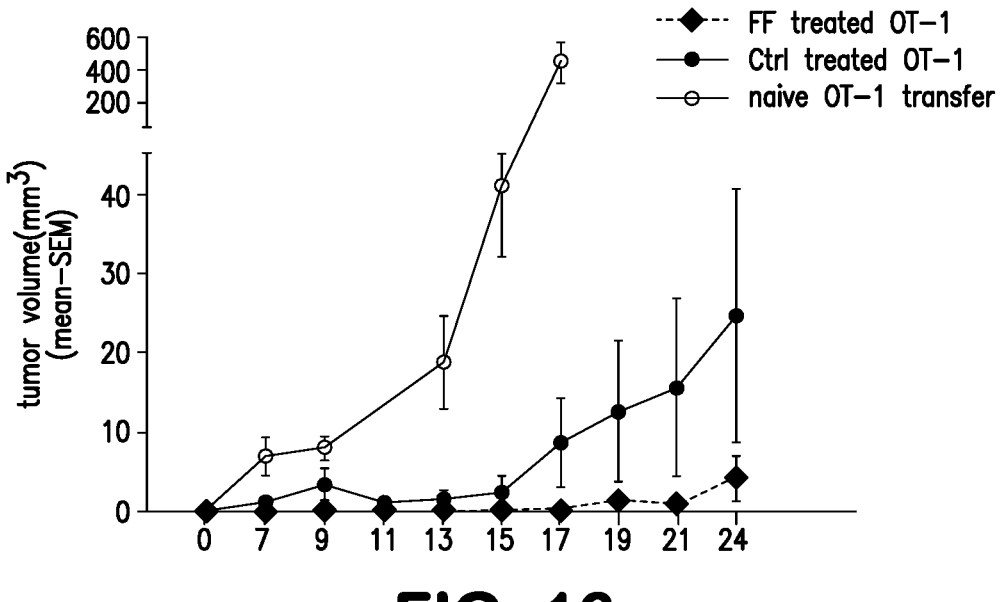

FIG. 15F shows a heat map indicating the various transcripts and functions affected by the treatment.

FIG. 16 is a graph showing the in vitro OT-1 CD8$^+$ T cells stimulated/activated with the SIINFEKL peptide and pre-treated with fenofibrate can inhibit the growth of melanoma tumor cells (transfected with the peptide) in a mouse model. See Example 8. The graph plots tumor volume (mm$^3$) vs. time (days). The effect of the FF-treated, peptide activated OT-1 cells (black closed circle) are contrasted with activated, control treated OT-1 cells (light gray closed circles) and naïve, unstimulated, untreated OT-1 cells (open circle).

DETAILED DESCRIPTION

The methods and compositions disclosed herein relate to the ability to "switch" the metabolism of T cells from the use of glucose and glycolysis to obtain energy to the use of fatty acid catabolism for direct or adjunctive treatment of cancer.

The inventors have determined and support via the data presented herein the use or supplemental use of metabolic interventions, i.e., drugs, compounds or reagents, that promote fatty acid catabolism by adoptively transferred or vaccine-induced CD8+ T cells to improve the efficacy of cancer immunotherapy. Specifically, this invention is based upon the determinations that: Metabolic stress within the TME decreases functions of tumor-infiltrating CD8+TILs. Lack of glucose within the TME forces CD8+TILs to switch to fatty acid catabolism. CD8+TILs subjected to low $O_2$ and glucose gain energy through ketone body catabolism; and CD8+TILs conditioned to increase FA catabolism show improved antitumor activity.

Specifically, as described below in the examples, using a mouse melanoma model, it was shown that metabolic challenges due to lack of glucose (Glu) combined with hypoxia within the TME impairs vaccine-induced CD8+TILs functions. When simultaneously subjected to hypoglycemia and hypoxia, CD8+TILs enhance catabolism of fatty acids (FAs) including ketone bodies, which partially preserves their effector functions. Preconditioning CD8+TILs to increase FA catabolism further improves their ability to slow tumor progression, although PD-1 expression concomitantly increases. Blockade of PD-1 signaling also reduces or delays tumor progression although it fails to affect vaccine-induced CD8+TIL functions or metabolism. PD-1 blockade (i.e., anti-PD-1 treatment) acts synergistically with metabolic reprogramming of T cells, particularly TILs, to achieve superior antitumor efficacy. Thus the methods and compositions provided herein use metabolic interventions to improve the efficacy of cancer immunotherapy.

The methods and compositions provided herein offer potential therapeutic interventions to delay loss of TIL functions caused by metabolic stress. First of all, the supporting data shown herein indicates that continued T cell receptor signaling in vaccine-induced CD8+TILs is not the sole factor that drives their functional exhaustion, as this fate is also encountered by CD8+TILs directed to an antigen that is not expressed within the TME. Additional data show that TILs experience metabolic stress within a glucose- and oxygen-lacking TME, which becomes increasingly severe during tumor progression. Hypoxia within solid tumors causes CD8+TILs to increase the hypoxia-induced factor (HIF)-1α signaling, which drives CD8+ T cell exhaustion by enhancing co-inhibitor lymphocytes activation gene (LAG)-3 expression and reducing the T cells' effector functions.

The data in the examples further show that lack of glucose within the TME enhances expression of PD-1 and impairs the CD8+TILs' functions. It forces CD8+TILs to switch to fatty acid (FA) catabolism demonstrated by stable isotope tracing directly in vivo and liquid chromatography-mass spectrophotometry. Promoting FA catabolism of CD8+TILs through the PPARα agonist fenofibrate slightly enhances their PD-1 expression, but nevertheless augments their effector functions and thereby achieves clinical benefits by delaying tumor progression. The data show that hypoglyce-mia and hypoxia play a critical role in driving metabolic reprograming and functional impairment of CD8+TILs. They further indicate that metabolic interventions that increase FA catabolism by CD8+TILs in a Glu-deprived TME improve the efficacy of cancer immunotherapy.

Thus various methods for treating cancer comprise administering to a mammalian subject having a cancer a T cell that is pretreated or conditioned ex vivo or in vitro with a compound or reagent that promotes the use of fatty acid catabolism rather than glucose for energy production by the pre-treated T cells and/or administering a compound or reagent that promotes the use of fatty acid catabolism by tumor antigen-specific T cells in the tumor microenvironment (referred to variously as "a fatty acid catabolism promoter" or "fatty acid catabolism-promoting compound"). Further methods involve administering a tumor-specific vaccine composition with the pretreated T cells or with the fatty acid catabolism-promoting compound. All of these possible methods that take advantage of switching the energy production metabolism of the T cells can optionally be coupled with checkpoint inhibition, such as PD-1 blockade.

Certain components and definitions used in the description of these methods and compositions are defined below.

"Patient" or "subject" as used herein means a mammalian animal, including a human, a veterinary or farm animal, a domestic animal or pet, and animals normally used for clinical research. More specifically, the subject of these methods and compositions is a human.

As used herein, the term "T cell(s)" or "T cell population" mean any human or mammalian T cell(s). In one embodiment, the T cell or populated is activated. In one embodiment, the T cell is an autologous or heterologous, naturally occurring T cell. In another embodiment, the T cell is a recombinantly or synthetically modified T cell construct. In some embodiments, the T cell to be pretreated is a primary T cell, a CD8 (cytotoxic) T cell, a CD8 (cytotoxic) T cell, a T infiltrating lymphocyte (TIL), an NK T cell or another T cell. In one embodiment, the T cell is obtained from the peripheral blood, TME or other fluid of the same mammalian subject into whom the T cell which is pre-treated or conditioned by the methods described herein is to be administered. In another embodiment, the T cell to be pretreated is primary T cell, a CD8 (cytotoxic) T cell, or an NK T cell or other T cell obtained from a bone marrow transplant match for the subject. Other suitable T cells include T cells obtained from resected tumors, a polyclonal or monoclonal tumor-reactive T cell. In one embodiment, the T cell is obtained by apheresis. In still other embodiments, the T cell is modified recombinantly or synthetically to express a heterologous antigen receptor. In one embodiment, the T cell is expresses a chimeric antigen receptor (CAR) or a chimeric endocrine receptor (CER). Such CARs or CERs are described in e.g., Sadelain, M et al, "The basic principles of chimeric antigen receptor (CAR) design" 2013 April, Cancer Discov. 3(4): 388-398; International Patent Application Publications WO2013/044255 and WO2016/054153, US patent application publication No. US 2013/0287748, and other publications directed to the use of such chimeric constructs. These publications are incorporated by reference to provide information concerning various components useful in the design of some of the constructs described herein. Such CAR or CER T cells are genetically modified lymphocytes expressing a ligand that allows them to recognize an antigen of choice. Upon antigen recognition, these modified T cells are activated via signaling domains converting these T cells into potent cell killers. An advantage over endogenous T cells is that they are not MHC restricted, which allows these T cells to overcome an immune surveillance evasion tactic used in many tumor cells by reducing MHC expression. In still other embodiment, the T cell for pretreatment is an endogenous or heterologous human T cell or human T cell line. Any T cell may be subjected to pretreatment ex vivo with a selected fatty acid catabolism promoter to "switch" its metabolic function from glycolysis to FA catabolism for the purposes of the methods and compositions provided herein.

As used herein the term "cancer" refers to or describes the physiological condition in mammals that is typically characterized by unregulated cell growth. More specifically, as used herein, the term "cancer" means any cancer characterized by the presence of a solid tumor. Suitable cancers for treatment by the methods described herein, include, without limitation, melanoma, breast cancer, brain cancer, colon/rectal cancer, lung cancer, ovarian cancer, adrenal cancer, anal cancer, bile duct cancer, bladder cancer, bone cancer, endometrial cancer, esophagus cancer, eye cancer, kidney cancer, laryngeal cancer, liver cancer, head and neck cancer, nasopharyngeal cancer, osteosarcoma, oral cancer, ovarian cancer, pancreatic cancer, prostate cancer, rhabdomosarcoma, salivary gland cancer, stomach cancer, testicular cancer, thyroid cancer, vaginal cancer, lung cancer, and neuroendocrine cancer.

The term "tumor," as used herein, refers to all neoplastic cell growth and proliferation, whether malignant or benign, and all pre-cancerous and cancerous cells and tissues. In one embodiment, the tumor targeted by the methods is characterized by hypoxia, significant infiltration with T lymphocytes, and low glucose in the tumor microenvironment.

As used herein, a compound or reagent that promotes the use of fatty acid catabolism by tumor antigen-specific T cells in the tumor microenvironment (referred to variously as "a fatty acid catabolism promoter" or "fatty acid catabolism-promoting compound") includes without limitation, compounds such as fenofibrate, clofibrate, gemfibrozil, ciprofibrate, bezafibrate or an AMPK activator, such as 5-aminoimidazole-4-carboxamide riboside. Other compounds, small molecule compounds or peptides, proteins or polypeptides, useful in these methods may be identified by one of skill in the art.

As used herein, the term "checkpoint inhibitor" refers to a composition or composition in the form of an antibody or a small molecule that binds or inhibits various checkpoint proteins. Such checkpoint proteins, including, without limitation, PD-1, PD-L1, CTLA-4, BTLA and CD160. As examples, known checkpoint inhibitors include the antibodies ipilimumab (Yervoy®), pembrolizumab (Keytruda®), and nivolumab (Opdivo®), among others. Other checkpoint inhibitors developed as small molecules or other checkpoint binding antibodies or antibody fragments are included in this definition.

As used herein, the term "antibody" refers to all types of immunoglobulins, including IgG, IgM, IgA, IgD, and IgE, including antibody fragments. The antibody can be monoclonal or polyclonal and can be of any species of origin, including (for example) mouse, rat, rabbit, horse, goat, sheep, camel, or human, or can be a chimeric antibody. See, e.g., Walker et al., Molec. Immunol. 26:403 (1989). The antibodies can be recombinant monoclonal antibodies produced according to known methods, see, e.g., U.S. Pat. No. 4,474,893 or 4,816,567, which are incorporated herein by reference. The antibodies can also be chemically constructed according to known methods, e.g., U.S. Pat. No. 4,676,980 which is incorporated herein by reference. See also, U.S.

Pat. No. 8,613,922, which is incorporated herein by reference. Antibody fragments are antigen binding fragments which include, for example, Fab, Fab', F(ab')2, and Fv fragments; domain antibodies, bifunctional, diabodies; vaccibodies, linear antibodies; single-chain antibody molecules (scFV); heavy chain or light chain complementarity determining regions, and multispecific antibodies formed from antibody fragments. Such antigen-binding fragments can be produced by known techniques.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "an immunotherapeutic composition targeting an antigen or ligand on the tumor cell" is meant any composition including cancer vaccines that target a cancer antigen in order to stimulate the subject's immune system. Such immunotherapeutic compositions are designed to elicit a humoral (e.g., antibody) or cellular (e.g., a cytotoxic T cell or T helper) response, or, in one embodiment, an innate immune response, is mounted to a target gene product delivered by the immunogenic composition following delivery to a mammal or animal subject. In one embodiment immunotherapeutic compositions useful in these methods involve presentation of the antigen to the subject's immune system via virus vectors, e.g., adenovirus, adeno-associated virus, lentivirus, retrovirus, poxvirus or others, or via virus-like particles (VLP). In another embodiment the immunotherapeutic composition used in the methods described herein is a DNA or RNA construct that expresses a cancer antigen. In another embodiment the immunotherapeutic composition used in the methods described herein is a composition comprising cancer antigens or fragments thereof as peptides or proteins. In another embodiment the immunotherapeutic composition used in the methods described herein is a monoclonal antibody or antigen-binding fragment(s) that specifically bind cancer antigens. The compositions are those that are created using known recombinant and synthetic techniques. See, e.g., reference in the examples to an exemplary melanoma immunotherapeutic composition, AdC68-gDMelapoly described in detail in U.S. Pat. No. 9,402,888 and in FIG. 7 thereof Many immunotherapeutic cancer "vaccine" are known and described in the art that can be used in the methods described herein.

By "antigen or ligand on the tumor cell" is meant a full-length, wild-type tumor-specific antigen or mutated tumor-specific antigens or tumor-associated antigens. Tumor-specific antigens are those epitopes and proteins found on a selected specific cancer or tumor cell, and not on all cancer cells. Cancer-associated antigens are antigens that may be associated with more than one cancer or tumor cell type. Exemplary cancer-specific antigens can include, without limitation, 707-AP, alpha (a)-fetoprotein, ART-4, BAGE; b-catenin/m, b-catenin/mutated Bcr-abl, CAMEL, CAP-1, mCASP-8, CDC27m, CDK4/m, CEA, CT, Cyp-B, MAGE-B2, MAGE-B1, ELF2M, ETV6-AML1, G250, GAGE, GnT-V, Gp100, HAGE, HER-2/neu, HPV-E7, HSP70-2M HST-2, hTERT, iCE, KIAA0205, LAGE, LDLR/FUT, MAGE, MART-1, MC1R, MUC1, MUM-1, -2, -3, P15, p190 minor bcr-abl. Still other suitable tumor or cancer genes encode VEGFR1, VEGFR2, MAGE-Ai, MUC-1, Thymosin β1, EGFR, Her-2/neu, MAGE-3, Survivin, Heparanase 1, Heparanase 2, and CEA, among others. Still other suitable antigens are those listed in the references, and incorporated by reference herein. See, also, texts identifying suitable antigens, such as Scott and Renner, in Encyclopedia of life Sciences 2001 Eds., John Wiley & Sons, Ltd.

By "vector" is meant an entity that delivers a heterologous molecule to cells, either for therapeutic or vaccine purposes. As used herein, a vector may include any genetic element including, without limitation, naked DNA, a phage, transposon, cosmid, episome, plasmid, or a virus or bacterium. Vectors are generated using the techniques and sequences provided herein, described in the examples, and in conjunction with techniques known to those of skill in the art. Such techniques include conventional cloning techniques of cDNA such as those described in texts such as Green and Sambrook, Molecular Cloning: A Laboratory Manual. $4^{th}$ Edit, Cold Spring Harbor Laboratory Press, 2012, use of overlapping oligonucleotide sequences of the *Salmonella* genomes, polymerase chain reaction, and any suitable method which provides the desired nucleotide sequence.

By "administering" or "route of administration" is meant delivery of the immunotherapeutic composition, or the fatty acid catabolism-promoter, or the checkpoint inhibitor or the pre-treated T cells used in the methods herein, to the subject. As discussed in detail below, these methods can be independent for each components of the method. Each administration method can occur with or without a pharmaceutical carrier or excipient, or with or without another chemotherapeutic agent into the TME of the subject. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. In one embodiment, the route of administration is oral. In another embodiment, the route of administration is intraperitoneal. In another embodiment, the route of administration is intravascular. Routes of administration may be combined, if desired. In some embodiments, the administration is repeated periodically, as discussed in detail below.

In the context of the compositions and methods described herein, reference to "one or more," "at least five," etc. of the compositions, compounds or reagents listed means any one or any and all combinations of the compositions, reagents or compounds listed.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

As used herein, the term "about" means a variability of 10% from the reference given, unless otherwise specified.

It is to be noted that the term "a" or "an", refers to one or more, for example, "an miRNA," is understood to represent one or more miRNAs. As such, the terms "a" (or "an"), "one or more," and "at least one" are used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

In one aspect of this invention, a composition for adoptive transfer to a mammalian subject comprises a T cell or T cell population that has been pretreated ex vivo or in vitro with a compound or reagent that conditions the cell to use fatty acid catabolism for energy production by the T cells. In one embodiment, the compound or reagent that promotes the use of fatty acid catabolism is fenofibrate. In another embodiment, the compound or reagent that promotes the use of fatty acid catabolism is clofibrate, gemfibrozil, ciprofibrate, bezafibrate, an AMPK activator, or 5-aminoimidazole-4-carboxamide riboside. Still other metabolic "switching" reagents are anticipated to be useful in the same manner.

These compositions may employ as the T cells for such pre-treatment an autologous or heterologous, naturally occurring T cell or a recombinantly or synthetically modified T cell construct. The T cell or population may be a human T cell or natural killer (NK) T cell or T infiltrating lymphocyte (TIL) obtained from the subject or from a bone marrow transplant match for the subject. In still other embodiments the T cell or population is obtained from human peripheral blood or from the tumor microenvironment of the subject. In still other embodiments, the T cell is modified to express a heterologous antigen receptor, or a chimeric antigen receptor (CAR-T) or a chimeric endocrine receptor (CER-T) prior to said pretreatment. In still other embodiments, the T cell or population slated for pretreatment is an endogenous or heterologous human T cell or human T cell line. In yet other embodiments, the T cell is a TIL or a CD8+ T cell. These compositions are prepared for adoptive transfer for the treatment of cancer, with or without an accompanying checkpoint inhibitor or tumor antigen specific immunological composition or vaccine.

In one embodiment of the methods described herein, a method for treating cancer comprises co-administering to a subject having a cancer characterized by a solid tumor an immunotherapeutic composition targeting an antigen or ligand on the tumor cell; and a compound or reagent that promotes the use of fatty acid catabolism by tumor antigen-specific T cells in the tumor microenvironment. In another embodiment, this method also involves co-administering a selected checkpoint inhibitor in the form of an antibody or a small molecule.

In another embodiment of the methods described herein, a method for treating cancer comprises administering to a subject having a cancer characterized by a solid tumor an immunotherapeutic composition targeting an antigen or ligand on the tumor cell; and a selected T cell, e.g., a tumor antigen-specific T cell or CAR, etc, pretreated ex vivo with a compound or reagent that promotes the use of fatty acid catabolism by the T cells so that the T cell uses fatty acids rather than glucose for energy production. These pretreated T cells can then be used for adoptive cell transfer.

In still another embodiment of the methods described herein, a method for treating cancer comprises administering to a subject having a cancer a composition comprising a T cell pretreated ex vivo or in vitro with a compound or reagent that promotes or switches the cell from using glucose for energy production to using fatty acids and FA catabolism for energy production. The T cells for such pre-treatment are selected from the list of T cells identified above.

By "pre-treatment with a selected fatty acid catabolism promoter" is meant that the selected T cell is cultured and expanded in the presence of the selected fatty acid catabolism promoter, e.g., fenofibrate at between about 1 to about 500 μM, for the entire or a fraction of the time of T cell expansion to condition the T cell to use fatty acids rather than glucose for energy production. In one embodiment a suitable concentration of the fenofibrate (or similar fatty acid catabolism promoter) is at least 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to at least about 500 μM.

Similarly intervening concentration between any two numbers listed is encompassed in the term "suitable concentration). The time of T cell expansion in one embodiment means the entire time of in vitro culture, which can span several hours to at least several days. In another embodiment, the time of T cell expansion is minimally 24 hours of in vitro culture. Other time periods for pre-treatment with the fatty acid catabolism promoter may be at least 1, 5, 10, 15, or 20 or more hours, or any intervening times between any specified number of hours stated herein. The pretreated T cells are then administered to the subject by well-known adaptive cell transfer techniques.

In one embodiment, the pretreated T cells are administered to treat cancer as a single therapy. In another embodiment, this method involves co-administering the immunotherapeutic compositions with the pretreated T cell. In still other embodiments, the method can also include administering a checkpoint inhibitor in the form of an antibody or a small molecule either simultaneously with or sequentially with the pretreated cells and/or the immunotherapeutic composition.

In still another variation of the method for treating cancer, the co-administration includes the immunotherapeutic composition, the fatty acid catabolism promoter (i.e., administered as a compound) and the selected pretreated T cells identified herein. In another embodiment, this method also involves co-administering a checkpoint inhibitor in the form of an antibody or a small molecule.

In any of the methods described herein, the immunotherapeutic composition and the fatty acid catabolism-promoting compound or reagent, or the immunotherapeutic composition and the pretreated T cell are administered substantially simultaneously. In another embodiment, the immunotherapeutic composition and the fatty acid catabolism-promoting compound or reagent, or the immunotherapeutic composition and the pretreated T cell are administered sequentially by the same or different routes of administration. The routes of administration selected depend upon the nature of the compositions. For example, if the fatty acid catabolism promoter is fenofibrate or another small chemical molecule, such molecules may be administered orally in doses known and accepted for other pharmaceutical uses of these drugs. In one embodiment, the immunotherapeutic composition and fatty acid catabolism promoter are independently administered systemically by intramuscular, intraperitoneal, intravenous, intratumoral or intranodal administration. In another embodiment, composition (b) is administered orally.

In other administration protocols, the fatty acid catabolism-promoting compound or reagent or the pretreated T cells are administered once or repeatedly from at least one to 14 days. In some protocols the administration occurs one to 14 days after administration of the immunotherapeutic composition. In certain embodiments, the immunotherapeutic composition is administered in a single dose. In other embodiments, the immunotherapeutic composition is administered as a booster dose.

In still further aspects of these methods, the subject may be treated with other anti-cancer therapies before, during or after treatment with the pre-treated T cells alone or with the immunotherapeutic composition and the fatty acid catabolism promoter or with the combination of the immunotherapeutic compositions and pre-treated cells. Such treatment may be concurrent or simultaneous with the fatty acid catabolism promoter or overlap treatment with the modified T cells adoptive transfer and/or the checkpoint inhibitors. In one embodiment, the methods involve treating the subject with chemotherapy before administering the immunotherapeutic composition and/or the fatty acid catabolism promoter. In still another embodiment, the method further comprises depleting the subject of lymphocytes and optionally surgically resecting the tumor prior to adoptive transfer of the selected T cells pretreated ex vivo with an fatty acid catabolism promoter to condition the T cell to use fatty acids rather than glucose for energy production.

In some embodiments, the pretreated cells are administered in a single dose, followed by optional administration of a checkpoint inhibitor. These doses may be repeated. In yet other embodiments of the methods, the immunotherapeutic composition is administered in a single dose without any booster, followed by administration of at least one of the fatty acid catabolism promoter, the selected pre-treated T cells, and/or the checkpoint inhibitors. In yet another embodiment, the immunotherapeutic composition is re-administered as a booster dose following administration of the fatty acid catabolism promoter, the selected pre-treated T cells, and/or the checkpoint inhibitors.

Any of these therapeutic compositions and components of the methods may be administered to a patient, preferably suspended in a biologically compatible solution or pharmaceutically acceptable delivery vehicle. The various components of the methods are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

Dosages of these therapeutic compositions will depend primarily on factors such as type of composition (i.e., selected pre-treated T cells, vectors, nucleic acid constructs or proteins) the condition being treated, the age, weight and health of the patient, and may thus vary among patients. The dosages for administration of the components of the methods are the conventional dosages known to be useful for administering that component. An attending physician may select appropriate dosages using the following as guidelines.

In one embodiment, a useful dosage of a pre-treated T cell is a single-infusion maximum tolerated dose (MTD), which may be determined by dose escalation studies in animal models. In one embodiment, a typical efficacious and non-toxic dose of T cells is between about $2\times10^4$ to $5\times10^9$ cells per kg/subject body weight. Other doses, such as $10^5$ or $10^6$ or $10^7$ or $10^8$ can be useful. See, the methods for dose determination as described in e.g., WO2016/054153 and in other CAR publications in the art.

In one embodiment, a typical dosage of an immunotherapeutic composition depends upon the nature of the composition. For example, if the composition is delivered in a viral vector, a therapeutically effective adult human or veterinary dosage of a viral vector is generally in the range of from about 100 µL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus.

If the composition (e.g., the immunotherapeutic composition, fatty acid catabolism-promoting compound or checkpoint inhibitor) is administered as an antibody or other protein, the dosages may range between a unit dosage of between 0.01 mg to 100 mg of protein (which is equivalent to about 12.5 µg/kg body weight). The dosage of the checkpoint inhibitor may be adjusted based on known toxicities of the particular antibody or small molecule used.

If any of the immunotherapeutic composition or the other components of the method is administered as naked DNA, the dosages may range from about 50 µg to about 1 mg of DNA per mL of a sterile solution.

Similarly, the doses of the fatty acid catabolism promoting compound may be similar to those administered for other uses, e.g., for cholesterol control or hyperlipidemia, of the similar compound. For example, FF may be administered at dosages of from 40 mg/day to 120 mg/day for adults. In yet another embodiment, a "standard" efficacious and non-toxic dose of pretreated T cells for adoptive transfer is about $10^7$ cells. As another example, the number of adoptively transferred T cells can be optimized by one of skill in the art. In one embodiment, such a dosage can range from about $10^5$ to about $10^{11}$ cells per kilogram of body weight of the subject. Other dosages are taught in the references recited herein and can be readily adjusted by one of skill in the art depending upon the treatment regimen, physical condition of the patient, type and stage and location of the tumor being treated, and taking into consideration other ancillary chemotherapies being used to treat the patient.

In yet another aspect, a therapeutic regimen is provided for the treatment of cancer comprising administering to a subject having a cancer characterized by a solid tumor a single dose of an immunotherapeutic composition targeting an antigen or ligand on the tumor cell on a day 1 of treatment. In this regimen, the subject is thereafter administered a compound or reagent that promotes the use of fatty acid catabolism by tumor antigen-specific T cells in the tumor microenvironment. The first dose of the fatty acid catabolism promoting compound of reagent begins on any of day 0, 1, 2, 3, 4 or 5 of treatment. Also involved in this regimen is the step of administering the fatty acid catabolism promoting compound or reagent daily from the beginning day of treatment of immunotherapeutic composition until a day occurring between day 7 to day 30 of treatment. The checkpoint inhibitors may be administered at the same time or following the administration of the fatty acid catabolism promoting compound.

In yet another aspect, a therapeutic regimen is provided for the treatment of cancer comprising administering to a subject having a cancer characterized by a solid tumor a single dose of an immunotherapeutic composition targeting an antigen or ligand on the tumor cell on a day 1 of treatment. In this regimen, the subject is thereafter administered by adoptive transfer the selected T cells pretreated ex vivo with a compound or reagent that promotes the use of fatty acid catabolism by tumor antigen-specific T cells to condition the T cell to use fatty acids rather than glucose for energy production. The adoptive transfer of the pre-treated T cells conditioned with the fatty acid catabolism promoting compound can occur on any of day 0-14 after administration of the immunotherapeutic composition. Thus in certain embodiments, the adoptive transfer occurs on day 0, 1, 2, 3, 4, 5, 6, 7, 8, 9, 10, 11, 12, 13 or day 14 or even later than day 14, after immunotherapeutic composition administration. Other dates may be selected depending upon how long the immunotherapeutic composition is expressed in vivo. This expression depends upon the type of vaccine and thus the timing of co-administration in the therapeutic regimen may be adjusted by one of skill in the art. The checkpoint inhibitors may be administered at the same time or following the administration of the pre-treated T cells.

In yet another embodiment, the discoveries of the inventors also permits a method of enhancing the survival of a chimeric antigen receptor-T cell or a chimeric endocrine receptor-T cell or ex vivo expanded tumor antigen-specific T cells, such as those described[41] and in e.g., International patent application publication No. WO2012/079000 and International patent application No. PCT/US2015/053128, each incorporated by reference. In one embodiment, the pretreated T cell is obtained from peripheral blood and modified to express a chimeric antigen receptor or a chimeric endocrine receptor and pretreated ex vivo with the fatty acid catabolism promoting compound or reagent. The pretreated T cell is an endogenous or heterologous human T cell or human T cell line. The pretreated T cell is a CD8+ T cell. In this method, the T cell(s) are pretreated ex vivo with a compound or reagent that promotes the use of fatty acid catabolism for energy production by tumor antigen-specific T cells in the tumor microenvironment as discussed above and then administered to the patient having a solid tumor by adoptive cell transfer, as described in the incorporated references.

The rationale for these methods is based in the inventors' observations in a mouse melanoma model that bystander CD8+TILs lose effector functions and increase expression of co-inhibitors. The data show that metabolic stress within the tumor microenvironment (TME) affects differentiation and effector functions of CD8+TILs in the mouse melanoma model. Hypoxia through HIF-1α and lack of glucose (Glu) enhance expression of co-inhibitors and impair CD8+ T cell functions. When simultaneously subjected to hypoxia and hypoglycemia, CD8+ T cells enhance catabolism of fatty acids (FAs) including ketone bodies. CD8+TILs conditioned to increase FA catabolism augment PD-1 expression and show improved production of effector molecules.

Hypoxia triggered by suboptimal neoangiogenesis or defects in perfusion within solid tumors causes CD8+ T cells to increase expression of the hypoxia-induced factor (HIF)-1α and lymphocytes activation gene (LAG)-3 and to lose functions. As shown with vaccine-induced CD8+TILs and in vitro activated polyclonal CD8+ T cells, hypoxia through hypoxia-induced factor (HIF)-1α increases co-inhibitor LAG-3 expression and impairs CD8+ T cell functions. Limited Glu supply enhances PD-1 expression, reduces effector functions and increases FA catabolism of CD8+ T cells, which is further enhanced under hypoxia. The inventors showed in the examples below that CD8+TILs in late stage tumors increasingly depend on FA catabolism fueled by FA uptake and triacylglycerol (TG) turnover to meet their energy demand, which increases PD-1 expression but preserves some effector functions. Promoting FA catabolism of CD8+TILs improves their antitumor efficacy. Further, LAG-3 overexpression and functional impairments can be reversed by genetic knock-down of HIF-1α.

Lack of glucose, which due to its consumption by tumor cells becomes scarce within a TME, impairs the CD8+TILs' functions, enhances expression of PD-1 and forces cells to switch to fatty acid metabolism as was shown by liquid chromatography-mass spectrophotometry and stable isotope tracing. This metabolic preference is further enhanced under hypoxia. Energy production through fatty acid oxidization rather than glucose requires more $O_2$ to generate equivalent amounts of ATP, which may not be sustainable under hypoxia. Ketone bodies, byproduct of fatty acid oxidization, are highly efficient fuels that require less $O_2$. Also, as supported by the data in the examples, and shown previously for cells of the nervous system subjected to hypoxia and hypoglycemia, CD8+TILs once they enter areas of hypoxia within a tumor switch to energy production through ketone body catabolism.

In recent years blockade of immunological checkpoints has evolved as one of the most promising therapies to enhance tumor antigen-specific immune responses and achieved durable clinical responses in cancer patients. Treatments with immune checkpoint inhibitors partially rescue TIL functions and have yielded promising results in cancer patients.[4] The assumption has been that antibodies, which inhibit signaling through immunoinhibitors, such as programmed cell death protein (PD)-1, preserve functions of T cells that due to chronic antigen stimulation differentiate towards exhaustion. The data provided herein show that continued T cell receptor signaling in vaccine-induced CD8+ tumor infiltrating T cells (TILs) is not the sole factor that drives their exhaustion and functional failure as this fate is also encountered by CD8+TILs directed to an antigen that is not expressed within the TME. Additional data gained with vaccine-induced TILs in comparison to CD8+ T cells stimulated under various culture conditions in vitro show that TILs experience metabolic stress within a glucose- and oxygen-lacking TME, which becomes increasingly severe during tumor progression.

Overall these data as presented in the Examples support that fatty acid metabolism is essential for CD8+TILs to preserve their tumoricidal functions within the TME. Additional data using drugs that promote fatty acid oxidization or mice with genetic alteration that affect lipid metabolism furthermore show that tumor antigen-specific CD8+ T cells conditioned during activation to use fatty acids rather than glucose for energy production show better preserved functions within the TME and achieve longer delays in tumor progression although they express higher levels of PD-1.

Embodiments of the Invention

Various embodiments of the invention include the following:

a) A method for treating cancer comprising administering to a subject having a cancer a T cell or T cell population that is pretreated or conditioned ex vivo or in vitro with a compound or reagent that promotes the use of fatty acid catabolism rather than glucose for energy production by the pre-treated T cells;

b) A method for treating cancer comprising co-administering to a subject having a cancer: an immunotherapeutic composition targeting an antigen or ligand on a tumor cell in the subject with one or more of (i) a compound or reagent that promotes the use of fatty acid catabolism by tumor antigen-specific T cells in the tumor microenvironment; and (ii) a T cell pretreated ex vivo with (i) to condition the T cell to use fatty acids rather than glucose for energy production for adoptive cell transfer;

c) Either of the methods above, further comprising administering a checkpoint inhibitor in the form of an antibody or a small molecule;

d) Any of the methods herein, wherein the checkpoint inhibitor is an anti-PD-1 antibody or small molecule ligand;

e) Any of the methods herein, wherein the cancer is characterized by the presence in the subject of a solid tumor;

f) Any of the methods herein, wherein the cancer is melanoma, breast cancer, brain cancer, colon/rectal cancer, lung cancer, ovarian cancer, adrenal cancer, anal cancer, bile duct cancer, bladder cancer, bone cancer, endometrial cancer, esophagus cancer, eye cancer, kidney cancer, laryngeal cancer, liver cancer, head and neck cancer, nasopharyngeal cancer, osteosarcoma, oral cancer, ovarian cancer, pancreatic cancer, prostate cancer, rhabdomosarcoma, salivary gland tumors, stomach cancer, testicular cancer, thyroid cancer, vaginal cancer, neuroendocrine cancer;

g) Any of the methods herein, wherein the compound or reagent that promotes the use of fatty acid catabolism by T cells is fenofibrate;

h) Any of the methods herein, wherein the compound or reagent that promotes the use of fatty acid catabolism by T cells is clofibrate, gemfibrozil, ciprofibrate, bezafibrate, an AMPK activator or 5-aminoimidazole-4-carboxamide riboside;

i) Any of the methods herein, wherein the T cell is an autologous or heterologous, naturally occurring T cell or a recombinantly or synthetically modified T cell construct;

j) Any of the methods herein, wherein the T cell is a human T cell or natural killer (NK) T cell or T infiltrating lymphocyte (TIL) obtained from the subject or from a bone marrow transplant match for the subject;

k) Any of the methods herein, wherein the T cell is obtained from human peripheral blood or from the tumor microenvironment of the subject;

l) Any of the methods herein, wherein the T cell is modified to express a heterologous antigen receptor, or a chimeric antigen receptor or a chimeric endocrine receptor prior to said pretreatment;

m) Any of the methods herein, wherein the T cell is an endogenous or heterologous human T cell or human T cell line;

n) Any of the methods herein, wherein the T cell is a CD8+ T cell;

o) Any of the methods herein, wherein said immunotherapeutic composition (a) is a recombinant virus or virus-like particle that expresses a cancer antigen, a DNA construct that expresses a cancer antigen, a composition comprising cancer antigens or fragments thereof as peptides or proteins, monoclonal antibodies or antigen-binding fragments that specifically bind cancer antigens;

p) Any of the methods herein, wherein the immunotherapeutic composition and the fatty acid catabolism-promoting compound or reagent, or the immunotherapeutic composition and the pretreated T cell are administered substantially simultaneously;

q) Any of the methods herein, wherein the fatty acid catabolism-promoting compound or reagent or the pretreated T cells are administered once or repeatedly from at least one to 14 days after administration of the immunotherapeutic composition;

r) Any of the methods herein, wherein the immunotherapeutic composition is administered in a single dose or as one or more booster doses;

s) Any of the methods herein, wherein each composition is independently administered systemically by intramuscular, intraperitoneal, intravenous, intratumoral or intranodal administration;

t) Any of the methods herein, wherein the compound or reagent that promotes the use of fatty acid catabolism by tumor antigen-specific T cells in the tumor microenvironment is administered orally;

u) Any of the methods herein, wherein the pretreated T cells are administered once or repeatedly;

v) Any of the methods herein, wherein the pretreated T cells are administered in a single dose or as one or more doses;

w) Any of the methods herein, wherein the pretreated T cells are administered systemically by intravenous injection or infusion;

x) Any of the methods herein, further comprising treating the subject with other anti-cancer therapies;

y) Any of the methods herein, further comprising treating the subject with chemotherapy before administering the pre-treated T cells, immunogenic composition or compound or reagent that promotes the use of fatty acid catabolism;

z) Any of the methods herein, further comprising depleting the subject of lymphocytes and optionally surgically resecting the tumor prior to administration of the pretreated T cells;

aa) Any of the methods herein, wherein the tumor targeted by the method is characterized by hypoxia, significant infiltration with T lymphocytes, and low glucose in the tumor microenvironment;

bb) A method of modifying a T cell comprising pretreating the T cell ex vivo or in vitro with a compound or reagent that conditions the cell to use fatty acid catabolism for energy production by the T cells;

cc) A method of enhancing the survival of a chimeric antigen receptor-T cell or a chimeric endocrine receptor-T cell or an ex vivo expanded tumor antigen-specific T cells comprising pretreating the T cell ex vivo with a compound or reagent that promotes the use of fatty acid catabolism for energy production by tumor antigen-specific T cells in the tumor microenvironment before adoptive cell transfer to a subject having a solid tumor;

dd) Any of the two preceding methods, wherein the compound or reagent that promotes the use of fatty acid catabolism is fenofibrate;

ee) Any of the three preceding methods herein, wherein the compound or reagent that promotes the use of fatty acid catabolism is clofibrate, gemfibrozil, ciprofibrate, bezafibrate, an AMPK activator, or 5-aminoimidazole-4-carboxamide riboside;

ff) Any of the four preceding methods herein, wherein the T cell is an autologous or heterologous, naturally occurring T cell or a recombinantly or synthetically modified T cell construct;

gg) Any of the five preceding methods herein, wherein the T cell is a human T cell or natural killer (NK) T cell or T infiltrating lymphocyte (TIL) obtained from the subject or from a bone marrow transplant match for the subject;

hh) Any of the six preceding methods herein, wherein the T cell is obtained from human peripheral blood or from the tumor microenvironment of the subject;

ii) Any of the preceding methods herein, wherein the T cell is modified to express a heterologous antigen receptor, or a chimeric antigen receptor or a chimeric endocrine receptor prior to said pretreatment;

jj) Any of the preceding methods herein, wherein the T cell is a CD8+ T cell;

kk) A therapeutic regimen for the treatment of cancer comprising:

1. administering to a subject having a cancer characterized by a solid tumor a single dose of an immunotherapeutic composition targeting an antigen or ligand on the tumor cell on a day 1 of treatment;

2. administering to said subject a compound or reagent that promotes the use of fatty acid catabolism by tumor antigen-specific T cells in the tumor microenvironment, said first dose of the fatty acid catabolism-promoting compound of reagent beginning on day 0-5 of treatment;

3. administering the fatty acid catabolism-promoting compound or reagent daily from the beginning day of treatment of (2) until a day occurring between day 7 to day 30 of treatment;

ll) A composition for adoptive transfer to a mammalian subject comprising a T cell that has been pretreated ex vivo or in vitro with a compound or reagent that conditions the cell to use fatty acid catabolism for energy production by the T cells;

mm) The preceding composition, wherein the compound or reagent that promotes the use of fatty acid catabolism is fenofibrate;

nn) The preceding compositions, wherein the compound or reagent that promotes the use of fatty acid catabolism is clofibrate, gemfibrozil, ciprofibrate, bezafibrate, an AMPK activator, or 5-aminoimidazole-4-carboxamide riboside;

oo) Any of the preceding compositions, wherein the T cell is an autologous or heterologous, naturally occurring T cell or a recombinantly or synthetically modified T cell construct;

pp) Any of the preceding compositions, wherein the T cell is a human T cell or natural killer (NK) T cell or T infiltrating lymphocyte (TIL) obtained from the subject or from a bone marrow transplant match for the subject;

qq) Any of the preceding compositions, wherein the T cell is obtained from human peripheral blood or from the tumor microenvironment of the subject;

rr) Any of the preceding compositions, wherein the T cell is modified to express a heterologous antigen receptor, or a chimeric antigen receptor or a chimeric endocrine receptor prior to said pretreatment;

ss) Any of the preceding compositions, wherein the T cell is an endogenous or heterologous human T cell or human T cell line; and tt) Any of the preceding compositions, wherein the T cell is a CD8+ T cell.

Within the tumor microenvironment vaccine-induced CD8+ T cells encounter metabolic stress due to lack of glucose and $O_2$, which results in increased expression of co-inhibitors and loss of functions. CD8+ tumor infiltrating T cells (TILs) react by enhancing catabolism of fatty acids including ketone bodies. Drug-induced increases in fatty acid oxidization further augment expression of the co-inhibitor PD-1 on CD8+TILs but significantly improve T cells' ability to slow tumor progression.

The inventors determined that lack of Glu and $O_2$ plays a critical role in driving the metabolic reprograming and functional exhaustion of CD8+TILs. They further indicate that metabolic interventions improve the efficacy of cancer immunotherapy.

The following examples are provided for the purpose of illustration only and the invention should in no way be construed as being limited to these examples but rather should be construed to encompass any and all variations that become evident as a result of the teaching provided herein. In summary, data presented herein elucidate underlying causes of failures of active cancer immunotherapy using a mouse melanoma model. Melanoma-bearing mice were immunized with a mixture of vaccines that induce CD8$^+$ T cells specific for melanoma-associated antigens (MAAs)

and an unrelated tumor antigen (TA), i.e., E7 of human papilloma virus (HPV)-16. Both MAA- and bystander E7-specific CD8+TILs increase co-inhibitor expression and lose functions, contesting the notion that high and sustained antigenic stimulation is solely liable for TIL exhaustion[5], although it may contribute by increasing the energy demand of CD8+ T cells that encounter their cognate antigen. Both CD8+ TIL subsets increasingly experience metabolic stress due to restricted $O_2$ and glucose supply during tumor progression.

Example 1: Materials and Methods

Cell Lines and Construction of Recombinant Adenovirus and Lentivectors.

The B16 cell line and the vaccines have been described previously.[40,15] The B16Braf$_{V600E}$ cell line (kindly provided by Dr. M Herlyn, Wistar Institute, Philadelphia, PA) was derived from B16.F10 cells by transduction with the lentivector pLU-EF1a-mCherry expressing mouse Braf$_{V600E}$. HEK 293 cells were used to propagate vaccine vectors. Cells were grown in Dulbecco's modified eagles medium (DMEM) supplemented with 10% fetal bovine serum (FBS).

Molecular construction, rescue, purification and titration of AdC68-gDMelapoly and AdC68-gDE7 vectors have been described[40]. The Melapoly transgene sequence (see FIG. 7 of U.S. Pat. No. 9,402,888) is composed of an ER signal sequence (ER ss) followed by a pan DR epitope (PADRE), three CD4+ T cell epitopes from human (h) Trp-2, and eight CD8+ T cell epitopes from human (h) or mouse (m)Trp-2, mTrp-1, hgp100 and mBrafV600E fused into herpes simplex virus (HSV) glycoprotein (g)D. The dominant CD8+ T response elicited by the AdC68-gDMelapoly vector is directed against the Trp-1455 epitope (~90% of MAA-specific CD8+ T cell response). Trp-1455-tetramer+CD8+ T cells were analyzed for phenotypical studies while MAA-specific CD8+ T cells were assessed for functional assays by intracellular cytokine staining throughout the figures.

Briefly, gDMelapoly or gDE7 construct was inserted into E1-deleted AdC68 viral molecular clone using I-CeuI and PI-SceI sites. The constructed plasmids were used to transfect HEK 293 T cells by calcium phosphate (Invitrogen, Carlsbad, CA). Cells containing adenoviral vectors were harvested 7-10 days later upon plague formation. Virus was further propagated on HEK 293 cells by serial infection and harvested by three cycles of freeze-thawing. Cell-free supernatant from the third cycle of thawing was used for virus purification by Cesium chloride density ultracentrifugation.

For production of lentivectors, five pLKO.1 lentivectors containing short hairpin RNAs (shRNAs) targeting different regions of HIF-1α or control RNA were obtained from The RNAi Consortium. The selection marker Thy1.1 was cloned from the pLKPO-Thy1.1 lentivector (Addgene) into each of the shRNA lentivectors. Lentivectors were generated using standard procedures. The 2$^{nd}$ generation lentivector package system (Addgene) was used and HEK 293T cells were transfected with the packaging plasmid PsPAX2, the envelope plasmid PMD2. G and each of the shRNA-Thy1.1-expressing insert plasmids at a ratio of 3:1:1. Supernatants were collected 48 and 72 hours post transfection. Lentivectors were concentrated by ultracentrifugation at 20,000 rpm, 4° C. for 2 hours. Vector pellets were incubated with PBS on ice for at least 2 hours before resuspension. The lentivector that showed the most pronounced reduction of HIF-1α transcripts in transfected cells was used for further studies.

Animal Experiments

Female C57Bl/6, B6. SJL-Ptprc$^a$Pepc$^b$/BoyJ (B6 CD45.1+), B6. PL-Thy1$^a$/CyJ (B6 CD90.1+) and B6; 129S4-Ppara$^{tm1Gonz}$/J (B6 PPAR-α KO) mice (6-8 weeks) were purchased from the National Cancer Institute (NCI) or the Jackson Laboratories and housed at the Wistar Institute Animal Facility. Procedures were conducted following approved protocols.

Groups of 5-80 C57BL/6 mice were vaccinated intramuscularly (i.m.) with AdC68 vectors ($10^{10}$ virus particles (vp) for AdC68-gDMelapoly; and $10^{11}$ vp for AdC68-gDE7) diluted in PBS. B16Braf$_{V600E}$ cells ($5 \times 10^4$ cells/mouse) diluted in phosphate buffered saline (PBS) were inoculated subcutaneously (s.c.) into the right flank. Tumor growth was monitored by measuring the perpendicular diameters of tumors every two days. Depending on size early stage tumors were harvested 10-14 days after challenge (referred to as 2 weeks) while late stage tumors were harvested 4-5 weeks after challenge (referred to as 1 month). Mice were euthanized once tumors exceeded a diameter of 1-1.5 cm.

For in vivo treatment, fenofibrate (FF; at 100 mg/kg/day, Sigma) was first diluted in dimethylsulfoxide (DMSO) and then further diluted in PBS and given by oral gavage daily for 3 weeks. Control mice received diluent at the same volume. For adoptive transfer experiments, $1 \times 10^7$ in vitro activated CD8+ T cells transduced with lentivectors or splenocytes from vaccinated mice treated with drugs and containing $5 \times 10^4$ Trp-1$_{455}$ tetramer+CD8+ T cells per dose were injected intravenously into recipient mice. For FF/control treated splenocytes or wild type/PPAR-α KO splenocytes co-transfer experiments, splenocytes containing $10^5$ Trp-1$_{455}$ tetramer+CD8+ T cells from each group were mixed and transferred into CD90.1+ recipient mice intravenously.

For PD-1 blockade experiments in NSG or unvaccinated C57BL/6 mice, anti-PD-1 antibody (clone 29F.1A12) or isotype control antibody (Clone: LTF-2, Bio X Cell) were given starting day 3 after tumor challenge. In vaccinated C57BL/6 mice, anti-PD-1 or isotype control antibody treatment was started 10 days after vaccination. The antibody was given by intraperitoneal injection every 3rd day at a dose of 200m g/mouse.

In Vitro Stimulation of CD8+ T Cells and Drug Treatments.

Enriched CD8+ T cells were activated for 4 days in 6-well plates pre-coated with antibodies to CD3 (5 µg/ml) and CD28 (5 µg/mL) (BD Bioscience). For some samples, cells were transferred for the last 16 hours to a hypoxia chamber. To study the impact of hypoxia on relatively resting CD8+ T cells, enriched CD8+ T cells were stimulated for 48 hours under normoxia. Cells were then removed from the plates, washed and replated in fresh medium with 100 U/ml human IL-2 for 96 hours, followed by culture in normoxia or hypoxia with IL-2 for another 36 hours before analysis. Cells were cultured in Roswell Park Memorial Institute (RPMI) medium without Glu (Life Technologies) supplemented with Glu (10 mM) or Gal (10 mM), 10% dialyzed FBS (Life Technologies), 20 mM HEPES, 2 mM Glutamax, 1 mM sodium pyruvate, 0.05 mM 2-mercaptoethanol and 1% penicillin-streptomycin. Hypoxia experiments were performed in a Thermo Napco series 8000WJ $CO_2$ incubator equipped with nitrogen tank for $O_2$ replacement. $O_2$ level was kept at 1% during CD8+ T cells hypoxia culture for time periods indicated in each assay. In all assays cell viability was assessed before staining. Activated CD8+ T Cells cultured in Glu medium under hypoxia showed stable percentage of live cells compared to those cultured under normoxia (~70-80% of blasts). Activated CD8+ T Cells cultured in Gal medium under normoxia showed reduced viability (~30-35% of blasts). The frequencies of live cells slightly increased if cells were subjected to both hypoxia and Gal medium (~46-50% of blasts). Drugs and corresponding vehicle controls were added as follows: 2-deoxy-D-glucose (2-DG, 2 mM, Sigma) or Fenofibrate (FF, 50 μM, Sigma) for the entire culture period; Etomoxir (Eto, 200 μM, Sigma) for the last 48 hours. DMSO concentrations were kept below 0.2% for all culture conditions.

CD8$^+$ T cells from spleens of naive C57Bl/6 mice were purified by negative selection using magnetic beads (MACS, STEMCELL Technologies). Enriched CD8$^+$ T cells were activated for 4 days in 6-well plates pre-coated with antibodies to CD3 (5 μg/ml) and CD28 (5 μg/mL) (BD Bioscience). For some samples, cells were transferred for the last 16 hours to a hypoxia chamber. To study the impact of hypoxia on resting CD8$^+$ T cells, purified enriched CD8$^+$ T cells were stimulated for 48 hours under normoxia. Cells were then washed off the plates and replated in fresh medium with 100 U/ml human IL-2 for 96 hours, followed by culture in normoxia or hypoxia with IL-2 for another 36 hours before analysis. Cells were cultured in Roswell Park Memorial Institute (RPMI) medium without Glu (Life Technologies) supplemented with Glu (10 mM) or Gal (10 mM), 10% dialyzed FBS (Life Technologies), 20 mM HEPES, 2 mM Glutamax, 1 mM sodium pyruvate, 0.05 mM 2-mercaptoethanol and 1% penicillin-streptomycin. Hypoxia experiments were performed in a Thermo Napco series 8000WJ CO$_2$ incubator equipped with nitrogen tank for O$_2$ replacement. O$_2$ level was kept at 1% during CD8$^+$ T cells hypoxia culture for time periods indicated in each assay. Drugs and corresponding vehicle controls were added as follows: 2-deoxy-D-glucose (2-DG, 2 mM, Sigma) or Fenofibrate (FF, 50 μM, Sigma) for the entire culture period; Etomoxir (Eto, 200 μM, Sigma), Amidepsine A (AmA, 20 μM, Santa Cruz), or Orlistat (OS, 100 μM, Sigma) for the last 48 hours. DMSO concentrations were kept below 0.2% for all culture conditions.

Metabolomics.

For glucose tracing in vitro, cells were stimulated with anti-CD3/CD28 for 4 days in medium containing 10 mM $^{13}C_6$-glucose or $^{13}C_6$-galactose. For FA tracing in vitro, cells were stimulated for 4 days in regular Glu or Gal medium and switched for the last 4 hours of culture to medium containing 10% delipidated FBS and 400 μM $^{13}C_{16}$-palmitate-BSA. In vivo tracing was conducted by injecting 2 g/kg [U-$^{13}$C] glucose i.p. 30 minutes before euthanasia or by feeding $^{13}C_{16}$-palmitate at 0.5 g/kg 2 hours, and injecting $^{13}C_{16}$-palmitate at 150 mg/kg dissolved in intralipid, 20% i.v. 1 hour before euthanasia. Samples were analyzed by LC-MS.

Extracellular Flux Analysis and Fatty Acid Catabolism Assay.

OCR and ECAR for CD8$^+$ T cells stimulated under different conditions were measured with XF24 and XF96 Extracellular Flux Analyzers (Seahorse Bioscience) following the manufacturer's instructions.

Hypoxia samples were prepared in a hypoxia chamber under 1% O$_2$. Dead cells were removed by dead cell removal kit using MACS and live cells were pre-incubated with 100 μM cobalt chloride before being removed from the hypoxia chamber and entered into the Seahorse analyzer. In experiments to determine the contribution of fatty acid oxidation (FAO) to OCR, 200 μM ETO was added 15 minutes before the Seahorse analysis. Briefly after repeated measures of basal respiration and lactate production, 1 μM OM was added to measure ATP leakage by OCR and glycolytic capacity by ECAR. 1.5 μM FCCP was then added to measure maximal respiration by OCR followed by addition of 100 nM Rotenone and 1 μM Antimycin A (AmA) to determine spare respiratory capacity by OCR and then 100 mM 2-DG to determine glycolytic reserve by ECAR.

For measuring catabolism (oxidation) of exogenous and endogenous FAs, cells activated in either Glu or Gal medium for 3 days were washed and transferred to substrate-limited Glu or Gal media for overnight stimulation. Substrate limited media contained 0.5 mM Glu or Gal, 1 mM GlutaMAX, 0.5 mM carnitine (all form Sigma) and 1% dialyzed FBS. Samples were treated with either ETO or vehicle control 15 minutes before the assay. Palmitate: BSA or BSA was added just before the assay.

The contributions of fatty acid catabolism FAO to OCR was calculated as follows: Basal respiration due to exogenous FA catabolism/oxidation=(Basal Palm:BSA-ETO OCR rate—basal BSA-ETO OCR rate)—OCR due to uncoupling by FFA; uncoupling by FFA=after OM injection, Palm:BSA-ETO OCR rate—BSA-ETO rate. Basal OCR due to endogenous FAs consumption=basal BSA-ETO OCR rate—basal BSA+ETO OCR rate.

Lipid and Glucose concentration measurement in tumor interstitial fluid.

Tumors interstitial fluid was collected as described (Wiig et al., 2003). Free FA species concentrations were determined by LC-MS. Absolute concentration of Glu was measured by LC-MS upon adding 13C6-Glu as the internal standard.

Lentivector Transduction of CD8$^+$ T Cells

For in vitro experiments, 4×10$^6$ enriched CD8$^+$ T cells were stimulated as described above for 24-28 hours. Freshly concentrated lentivectors were spin-inoculated into activated CD8$^+$ T cells supplemented with polybrene (6 μg/ml, Santa Cruz) at 2000 rpm, 32° C. for 2 hours. Cells were washed 20 hours after transduction, transferred to new CD3 antibody pre-coated plates and stimulated for another 40 hours in medium supplemented with anti-CD28 and human IL-2 (100 U/ml, Roche) under normoxia or switched to part time hypoxia. Lentivector-transduced CD8$^+$ T cells were identified by surface staining for Thy1.1 followed by analysis with a BD LSRII.

For in vivo adoptive transfer experiments, cells were washed 20 hours after lentivector transduction and cultured for an additional 48 hours with medium supplemented with human IL-2 (100 U/ml) before cell transfer. Lentivector-transduced CD8+ T cells were identified by surface staining for Thy1.1. Recipient Thy1.2+ mice at the time had been challenged with tumor cells 5 days earlier and had been vaccinated with AdC68-gDMelapoly 2 days earlier. For in vivo experiments CD8+ T cells from spleens of naïve C57Bl/6 mice were purified by negative selection using magnetic beads (MACS, STEMCELL Technologies). Enriched CD8+ T cells were stimulated with anti-CD3/CD28 antibodies for 24 hours prior to lentivector transduction via spin inoculation.

Isolation of Lymphocytes from Mice

PBMCs and splenocytes were harvested as described[40]. Briefly, blood samples were collected by retro-orbital puncture and PBMCs were isolated by Histopaque (Sigma) gradient. Spleens were harvested and single cell suspension was generated by mincing with mesh screen in Leibovitz's L15 medium and passing through 70 μm filter (Fisher Scientific, Waltham, MA). For both samples red blood cells were lysed by 1×RBC lysis buffer (eBioscience, San Diego, CA). To obtain tumor-infiltrating lymphocytes, tumors were harvested, cut into small fragments and treated with 2 mg/ml collagenase P, 1 mg/ml DNase I (all from Roche) and 2% FBS (Tissue Culture Biologicals) in Hank's balanced salt solution (HBSS, 1×, Thermo Fisher Scientific) under agitation for 1 hour. Tumor fragments were homogenized, filtrated through 70 μm strainers and lymphocytes were purified by Percoll-gradient centrifugation and washed with DMEM supplemented with 10% FBS. Pre-experiments were conducted to ensure that this treatment did not affect any of the markers that were tested.

Antibodies, Staining and Flow Cytometry

Cells were stained with a PE-labeled Trp-1-specific MHC class I (H-2D$^b$) tetramer carrying the TAPDNLGYM peptide and an Alexa647-labeled HPV-16 E7-specific MHC class I (H-2D$^b$) tetramer carrying the RAHYNIVTTF peptide (obtained from the NIAID Tetramer Facility). Lymphocytes were stained with anti-CD8-PerCPCy5.5 or -Alexa700, CD4-PercpCy5.5, CD44-PacBlue, LAG-3-APC or -PercpCy5.5, KLRGI-FITC, PD-1-PE-Cy7 or -Brilliant violet (BV) 605 (all from Biolegend), 2B4-FITC (eBioscience) and Amcyan fluorescent reactive dye (Life Technologies).

For mitochondrial metabolic markers analysis, cells were stained with Mitosox Red (5 μM, MROS) and DioC6 (40 nM, MMP) (Life Technologies) at 37° C. for 30 minutes under either normoxia or hypoxia (for in vitro samples cultured prior to staining under hypoxia). For fatty acid uptake experiments, cells stimulated under different conditions in vitro or isolated from spleen and tumors of mice bearing 2 weeks or 1 month-old tumors were immediately incubated with 1 μM BODIPY FL $C_{16}$ (Life tech) for 30 mins at 37° C. Cells were washed twice with cold PBS before surface staining. For Cpt1a staining, cells were stained for surface markers first followed by permeabilization with transcription factor buffer set (BD Pharmingen, San Diego, CA). Cells were stained with anti-Cpt1a antibody or mouse IgG2b isotype control antibody (abcam) at 5 μg/ml in 1× permwash for 45 mins at 4° C. For staining of T-bet, cells were first stained for surface markers, then fixed and permeabilized with Foxp3/Transcription factor staining buffer and stained with T-bet-PE-Cy7 Eomes-FTIC (all from eBioscience) or primary antibody against FoxO1 (C29H4, Cell Signaling Technology). Total FoxO1 was further determined by anti-rabbit secondary antibody staining (CST). For phosphorylated (p)Akt staining, cells were stained with BD Phosflow buffer set and Phospho-Akt (CST) antibody.

For intracellular cytokine staining (ICS) of ex vivo lymphocytes ~$10^6$ cells per samples were cultured in DMEM containing 2% FBS and Golgiplug (Fisher Scientific, 1.5 μl/ml) for 6 hours with either a peptide pool (5 μg/ml for each peptide) including all CD8$^+$ T cell epitopes expressed by gD-Melapoly (mTrp-1$_{455463}$: TAPDNLGYA, mTrp-1$_{481-489}$: IAVVAALLL, mTrp-2$_{522-529}$: YAEDYEEL, hTp-2$_{180-188}$: SVYDFFVWL, hTrp-2$_{343-357}$: STFSFRNAL, mTrp-2$_{363-371}$: SQVMNLHNL, hgp100$_{25-33}$: KVPRNQDWL, mBraf$_{594-602}$: FGLANEKSI) or the E7 peptide: RAHYNIVTTF (Genescript). A rabies virus glycoprotein peptide was used as a negative control.

For ICS performed with CD8$^+$ T cells stimulated in vitro, ~$10^6$ cells were transferred to 96 well plates in the original medium and stimulated with PMA (500 ng/ml), ionomycin (20 μg/ml) and Golgiplug for 4 hours under either normoxia or hypoxia. Staining was conducted as described before.[14] Cells were stained with antibodies to IFN-γ (APC or BV421), granzyme B (APC, Life Technologies) and perforin (PE, eBioscience). Cells were analyzed by an LSRII (BD Biosciences). Data were analyzed with FlowJo (TreeStar).

BRDU Proliferation Assay

Mice were intraperitoneally injected with 1.5-2 mg/mouse of BrdU solution and fed water-containing BrdU at a concentration of 0.8 mg/ml for 24 hours before the assays. They were euthanized and lymphocyte samples were analyzed for BrdU incorporation. Cells were first stained for surface markers and then for intracellular BrdU (1:50 dilution) according to the manufacture's instruction (BD Bioscience).

HIF-1α and Glut1 Staining

For ex vivo assays mice were perfused immediately after euthanasia with PBS and heparin (10 units/ml) and then with 1 mM cobalt (II) chloride (Cocl$_2$, EMD Millipore) diluted in PBS. For both ex vivo and in vitro experiments, lymphocytes isolation and staining before fixation were performed in medium containing 200 μM Cocl$_2$. For staining, lymphocytes were first blocked with 10% normal goat serum (Life Technology) for 30 minutes at room temperature and then stained with anti-Glut1 primary antibody or mouse IgG2a isotype control antibody (Abcam) at 1 μg/$10^6$ cells for 60 minutes at room temperature. Cells were washed and stained with PacBlue labeled-goat anti-mouse secondary antibody (1:2000 dilution) together with antibodies to other cell surface markers for 30 minutes. Cells were fixed, permeabilized, and stained for HIF-1α with anti-HIF-1α-Alexa700 antibody (R&D) using the FoxP3 buffer set (eBioscience).

Glucose Concentration Measurement in Tumor Interstitial Fluid

Mice bearing week 2 or 1 month-old tumors were euthanized. Tumors were removed and interstitial fluid was collected as described 37. Glu concentration was determined with Glu meters.

Cell Culture And Isotopic Labeling.

For $^{13}C_6$-Glu/Gal tracing in vitro, cells were cultured from the onset of the assays in Glu-free RPMI medium with 10 mM Glu/Gal-$^{13}C_6$(Sigma) for 4 days. For $^{13}C_{16}$-palmitate tracing in vitro, cells were stimulated for 3 days in Glu or Gal medium. On the night of day 3, some samples were transferred to 1% $O_2$ for overnight culture. $^{13}C_{16}$-palmitate (Sigma) was first dissolved in 100% ethanol at 200 mM and conjugate to fatty acid-free BSA (Sigma) at a 5:1 molar ratio to a final concentration of 8 mM-$^{13}C_{16}$-palmitate-BSA by vortexing at 37° C. for 3-4 hours with sonication. On day 4, samples were pelleted and replated in fresh medium with 10% delipidated FBS (Cocalico Biologicals, Reamstown, PA) and 400 μM $^{13}C_{16}$-palmitate-BSA. Hypoxia samples were returned to 1% $O_2$. All samples were cultured for another 4 hour. Dead cells were removed by MACS. Samples were pelleted at 4000 rpm for 5 minutes. All collection procedures were conducted at 4° C.

Cell numbers in each sample were determined. Metabolism was quenched and metabolites were extracted by adding 1 ml −80° C. 80:20 methanol:water per million cells. After 20 min of incubation on dry ice, samples were centrifuged at 10000 g for 5 min. Insoluble pellets were re-extracted with 1 ml −80° C. 80:20 methanol:water on dry ice. The supernatants from two rounds of extraction were combined, dried under $N_2$, resuspended in 1 ml water per million cells. Metabolites were normalized to cell number.

For $^{13}C_6$-Glu tracing in vivo, tumor-bearing mice were fasted for 16 hours overnight. $^{13}C_6$-Glu was diluted in PBS and given i.p. to mice at 2 g/kg. Spleen and tumors were collected 30 minutes after injection. For U$^{13}C_{16}$-palmitate tracing mice were fasted for 16 hours, they were then $^{13}C_{16}$-palmitate dissolved in polyethylene glycol 300 (Hampton Research, Aliso Viejo, CA) at 0.5 g/kg by oral gavage. 1-hour later $^{13}C_{16}$-palmitate dissolved in intralipid, 20% (Sigma) was given i.v. 150 mg/kg. Mice were euthanized 1 hour after the i.v. injection and spleens and tumors were collected. Tissues were processed and cells were isolated on ice as rapidly as possible. CD8$^+$CD44$^+$ T cells from pooled spleens and tumors were stained and sorted at $4^\circ$ C., cell numbers were determined. Metabolites were extracted with $-80^\circ$ C. 80:20 methanol:water, dried under $N_2$, resuspended in 1 ml water. Metabolites were normalized to cell number. Contribution of $^{13}C$ to TCA cycle metabolites was calculated as $[(m+1)*1^+ \ldots (m+n)*n]/\{[(m+0)+ \ldots +(m+n)]*n\}*100\%$, where m+0 is the normalized signal intensity of a metabolite in $^{12}C$ form, m+n indicates normalized signal intensity for each form of $^{13}C$ labeled metabolite, n indicates the total number of carbon atoms in that metabolite.

LC-MS Instrumentation and Method Development.

Glycolytic and TCA metabolites were analyzed by reversed-phase ion-pairing chromatography coupled with negative-mode electrospray-ionization high-resolution MS on a stand-alone orbitrap (Thermo) (Lu et al., 2010). Carnitine species were analyzed by reversed-phase ion pairing chromatography coupled with positive-mode electrospray-ionization on a Q Exactive hybrid quadrupole-orbitrap mass spectrometer (Thermo); Liquid chromatography separation was achieved on a Poroshell 120 Bonus-RP column (2.1 mm×150 mm, 2.7 μm particle size, Agilent). The total run time is 25 min, with a flow rate of 50 μl/min from 0 min to 12 min and 200 μl/min from 12 min to 25 min. Solvent A is 98:2 water:acetonitrile with 10 mM amino acetate and 0.1% acetic acid; solvent B is acetonitrile. The gradient is 0-70% B in 12 min. All isotope labeling patterns were corrected for natural $^{13}C$-abundance.

Gene Expression Analysis

Lymphocytes were isolated from spleens and tumors of mice (tumor-bearing or normal) at different time points and stained with dyes and antibodies to live cells, CD8$^+$, CD44$^+$ and the Trp-1 and E7 tetramers. For co-adoptive transfer experiments, CD8$^+$CD44$^+$ T donor cells of different origin were recovered from spleen and tumors of recipient mice three weeks later by antibodies staining and sorting. Cells were sorted (Mono Astrios, Beckman Coulter) on ice into Trp-1 or E7 tet$^+$CD44$^+$CD8$^+$ T cells into RNAprotect cell reagents (QIAGEN).

For in vitro cultured samples ~$10^6$ cells/sample were processed on ice to remove dead cells using manual cell separation columns and Mini/Midi MACS separators (Miltenyi Biotec). For lentivector transduction assays, transduced cells were further purified based on Thy1.1 expression using MACS. RNA was isolated from purified cells using RNeasy Mini kits (Qiagen) and RNA concentrations were determined using Nanodrop (Thermo Scientific). cDNAs were obtained by reverse transcription using the high capacity cDNA reverse transcription kit (Life Technologies). Relative quantitative real-time PCR analyses were performed using 7500 Fast Real-Time PCR system (Life Technologies). b-2 microglobulin or GAPDH were used as internal controls. GAPDH or β-2 microglobulin were used as internal controls. Table 1 shows the metabolic pathways, gene name and forward and reverse primers for the gene expression analysis described in Example 1. Vector NTI was used for primers design.

TABLE 1

| Metabolic Pathways | Gene name (Forward-F and Reverse-R | Primer Sequences | SEQ ID NO |
|---|---|---|---|
| Glucose metabolism | mGLUT1-F | TGTGGGAGGAGCAGTGCTCG | 2 |
| | mGLUT1-R | TGGGCTCTCCGTAGCGGTG | 3 |
| | mHK2-F | TGATCGCCTGCTTATTCACGG | 4 |
| | mHK2-R | ACCGCCTAGAAATCTCCAGAAGG | 5 |
| | mPGK1-F | ATGTCGCTTTCCAACAAGCTG | 6 |
| | mPGK1-R | TGGCTCCATTGTCCAAGCAG | 7 |
| | mIDH3a-F | TGGGTGTCCAAGGTCTCTCG | 8 |
| | mIDH3a-R | TCTGGGCCAATTCCATCTCC | 9 |
| | mMDH2-F | TTGGGCAACCCCTTTCACTC | 10 |
| | mMDH2-R | TGTGACTCAGATCTGCTGCCAC | 11 |
| Lipid metabolism regulation, FAs uptake, TG synthesis and lipolysis and FA synthesis | mPPAR α-F | AGCCCCATCTGTCCTCTCTCC | 12 |
| | mPPAR α-R | TCCAGAGCTCTCCTCACCGATG | 13 |
| | mSLC27A4-F | TGAGTTTGTGGGTCTGTGGCTAGG | 14 |
| | mSLC27A4-R | AAGACAGTGGCGCAGGGCATC | 15 |
| | mSLC27A2-F | TGCTGCTGCTGCCTCTGCTG | 16 |
| | mSLC27A2-R | AGGATGGTACGCACGGGTCG | 17 |
| | mDGAT1-F | ACCTGGCCACAATCATCTGCTTC | 18 |
| | mDGAT1-R | TTGGCCTTGACCCTTCGCTG | 19 |
| | mDGAT2-F | AGCATCCTCTCAGCCCTCCAAG | 20 |
| | mDGAT2-R | TAGCACCAGGAAGGATAGGACC | 21 |
| | mPNPLA2-F | TTCCCGAGGGGAGACCAAGTG | 22 |
| | mPNPLA2-R | TGCCGAGGCTCCGTAGATG | 23 |
| | mLIPA-F | TGCTTTCTCGGGTGCCCAC | 24 |
| | mLIPA-R | TCCTCACCAGGATATCCCCAG | 25 |
| Peroxisomal FAO | mACAA1α-F | TCCGCTAGGTTCCCGCAGG | 26 |
| | mACAA1α-R | ACAGAAGCTCGTCGGGGGTG | 27 |
| | mEHHADH-F | AAAGTTCGCAAAGGGCAAGG | 28 |
| | mEHHADH-R | TCGCCCAGCTTCACAGAGC | 29 |
| | mACOX1-F | TCCCGATCTGCGCAAGGAG | 30 |
| | mACOX1-R | TGTTCTCCGGACTACCATCCAAG | 31 |
| | mHSD17B4-F | TTGTGAACGACTTAGGAGGGGAC | 32 |
| | mHSD17B4-R | AAATGTGTCCAGTGCCGTCGGC | 33 |
| Mitochondrial FAO | mACADVL-F | ACCCTCTCCTCTGATGCTTCCAC | 34 |
| | mACADVL-R | TGAGCACAGATGGGTATGGGAAC | 35 |
| | mACADM-F | AAGCAGGAGCCCGGATTAGG | 36 |
| | mACADM-R | TCCCCGCTTTTGTCATATTCC | 37 |

TABLE 1-continued

| Metabolic Pathways | Gene name (Forward-F and Reverse-R | Primer Sequences | SEQ ID NO |
|---|---|---|---|
| Ketone Body | mBDH1-F | TCGCCATACTGCATCACCAAG | 38 |
| Metabolism | mBDH1-R | TGCCAGGTTCCACCACACTG | 39 |
| ROS | mNOX1-F | AGAAATTCTTGGGACTGCCTTGG | 40 |
| production/ | mNOX1-R | TGCCCCTCAAGAAGGACAGC | 41 |
| detoxification | mSOD1-F | ACAGGATTAACTGAAGGCCAGC | 42 |
| and Electron | mSOD1-R | TTGCCCAGGTCTCCAACATG | 43 |
| transport | mCAT-F | TGACATGGTCTGGGACTTCTGG | 44 |
| chain (ETC) | mCAT-R | AGCCATTCATGTGCCGGTG | 45 |
|  | mCOX5B-F | ACCCGCTCCATGGCTTCTG | 46 |
|  | mCOX5B-R | AGTCCCTTCTGTGCTGCTATCATG | 47 |

Differences in transcript expression levels are visualized in heatmaps. Values were log transformed to show ratios of differences. Color scale was set as −2 (lower expression, deep blue) to 2 (higher expression, deep red).

Isotope Labeling In Vivo

Tumor-bearing mice were fasted for 16 hours. 13C6-Glu (Cambridge) diluted in PBS was given i.p. to mice at 2 g/kg. Spleens and tumors were collected 30 minutes later. 13C16-potassium palmitate was conjugated to FAfree BSA (6:1 molar ratio) and given to mice at ~0.35 g/kg by oral gavage. 1-hour later 13C16-palmitate-BSA was given i.v. at 125 mg/kg. Spleens and tumors were collected 30 mins later and cells were isolated on ice. Tumor samples were weighed and flash frozen in liquid nitrogen. CD8+CD44+ T cells from pooled samples were stained and sorted at 4° C. Metabolites were extracted with −80° C. 80:20 methanol:water, dried under N2 and resuspended in water at 100 mg tissue/ml or $10^6$ cells/100 μl.

Statistical Analysis

Significance of differences between 2 populations was calculated by student's t test; significance of differences among multiple populations was calculated by one-way or two-way ANOVA using GraphPad Prism 6. Differences in survival were calculated by Log-rank Mantel-Cox test. Significance was set at p-values of or below 0.05. Type I errors were corrected for multiple comparisons using the Holm-Šídák method.

Example 2: CD8+ T Cells Become Functionally Impaired within the TME Independent of Recognition of their Cognate Antigen To test if the fate of CD8+TILs depends on continued antigen recognition, we used two vaccines in a transplantable mouse melanoma model. One, termed AdC68gD-Melapoly[40] is an adenovirus (Ad)-based polyepitope vaccine that elicits MAA-specific CD8+ T cell responses, mainly to the Trp-$1_{455-463}$ epitope; the other, termed AdC68-gDE7[15], stimulates CD8+ T cells to E7.

Figure 1A:
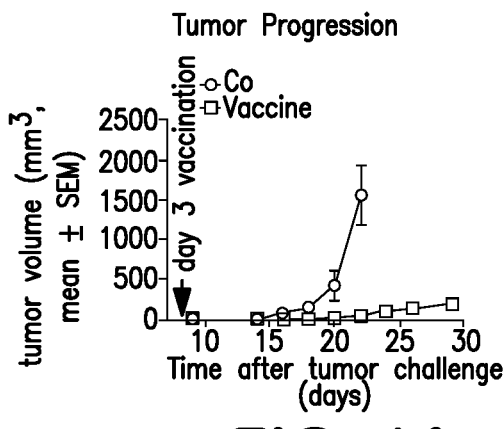
FIG. 1A is a graph showing tumor growth in mice that received AdC68-gD (Control, Co) or AdC68-gDMelapoly mixed with AdC68-gDE7 (Vaccine) 3 days after tumor challenge (n=6-18/group). CD8+TILs become functionally impaired within the tumor microenvironment (TME).

We vaccinated mice bearing 3-day old B16BrafV600E tumors and normal mice with AdC68-gDMelapoly mixed with AdC68-gDE7. Vaccination delays tumor progression (FIG. 1A). Experiments indicating the numbers of tetramer (tet)+Trp-1- and E7-specific CD8+ T cells/$10^6$ live cells in spleens (Spl) and tumors of mice that had or had not been challenged with tumor cells 3 days (d) before vaccination (n=7-10/group), revealed that both Trp-1 and E7-specific CD8+ T cells accumulate within tumors where they contract more rapidly in TME than in periphery during tumor progression (data not shown).

The % of bromodeoxyuridine (BrdU) incorporation into Trp-1- and E7-specific specific CD8+ T cells from spleens and tumors of mice that had been challenged with B16 cells 3 days before vaccination (n=5/time point) was measured. BrdU was administered one day before euthanasia for 24 hours on days 9, 19 or 29 after vaccination. Measurements were taken on day 10, day 20 and month 1 (n=5, representative of 2 experiments). Only Trp-1 specific CD8+ T cells proliferate in the tumor. Numbers of Trp-1-specific CD8+ TILs declined by more than 90% between 10 days and 1 months after vaccination while E7-specific CD8+TILs declined less by ~80%. This prominent reduction of Trp-1-specific CD8+TIL numbers was observed even though they proliferate within tumors. Nevertheless their proliferation decreases over time despite continued presence of Trp-1 antigen (not shown).

Mean fluorescent intensity (MFI) and representative histograms for PD-1 and LAG-3 on specific CD8+ T cells were produced from spleens and tumors at 2 weeks (wk) or 1 month (mo) after vaccination. Both Trp-1-specific and bystander E7-specific CD8+ T cells from 2-week and, to a more pronounced extent, 1-month tumors increase expression of exhaustion markers PD-1 and LAG-3 within the TME (data not shown). Both Trp-1-specific and bystander E7-specific CD8+ T cells lose functions within the TME.

Figure 1B:
FIG. 1B are a bar graph (left) showing the ratio of antigen-specific CD8+ T cell frequencies from spleens and tumors producing factors harvested 1 mo over those harvested 2 wk after tumor challenge; and a bar graph (right) showing absolute frequencies of specific CD8+ T cells at 1 mo after challenge from spleens or tumors producing 3 or 2 factors. Production of IFN-γ, granzyme B (GrzmB) and perforin were measured. n=5-7/group.
Figure 1B:
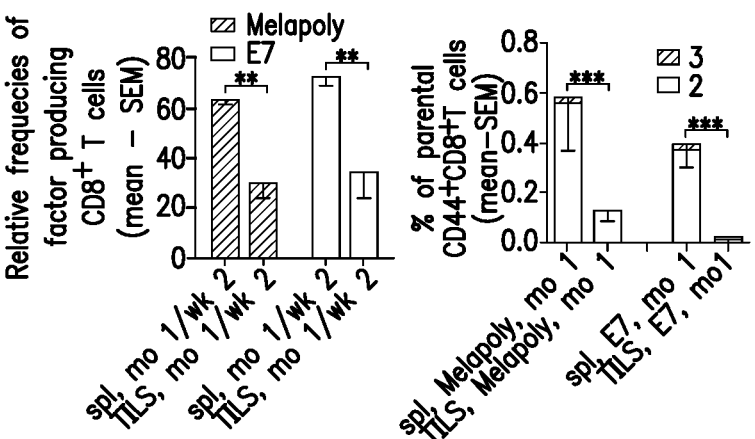

This, combined with declining frequencies of antigen-specific CD8+TILs producing effector molecules, such as lytic enzymes or interferon (IFN)-γ and reduced polyfunctionality (FIG. 1B), suggests that vaccine-induced TILs regardless of their epitope specificity, differentiate towards 'exhaustion' during tumor progression. Ad vectors used for vaccination persist at low levels thus maintaining high frequencies of fully functional effector CD8+ T cells (Tatsis et al., 2007).

Figure 1C:
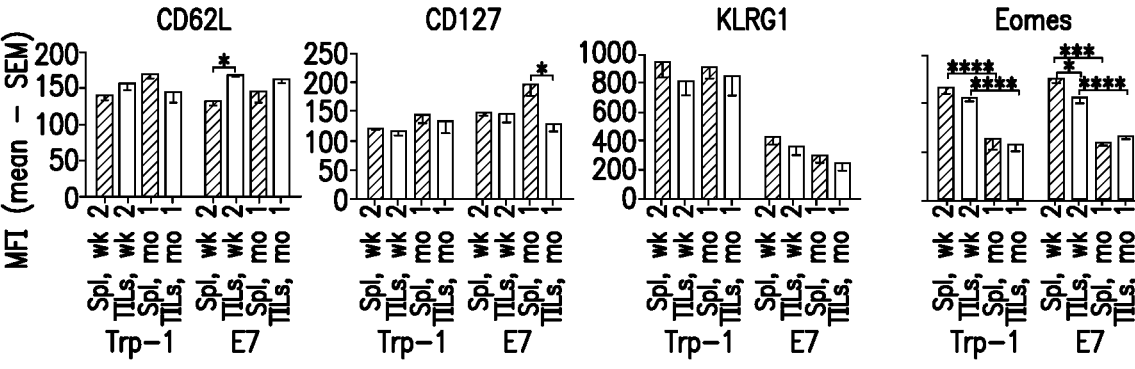
FIG. 1C are 4 graphs showing MFI (mean-SEM) of CD62L, CD127, KLRG1 and Eomes (left to right) on/in specific CD8+ T cells from spleens. n=5-7/group. For all figures, results are shown as mean values with standard errors of mean (SEM). (*) Indicates significant differences between groups; *$p \leq 0.05$-0.01, $p \leq 0.01$-0.001, *$p \leq 0.001$-0.0001, ****$p \leq 0.0001$.
Figure 1D:
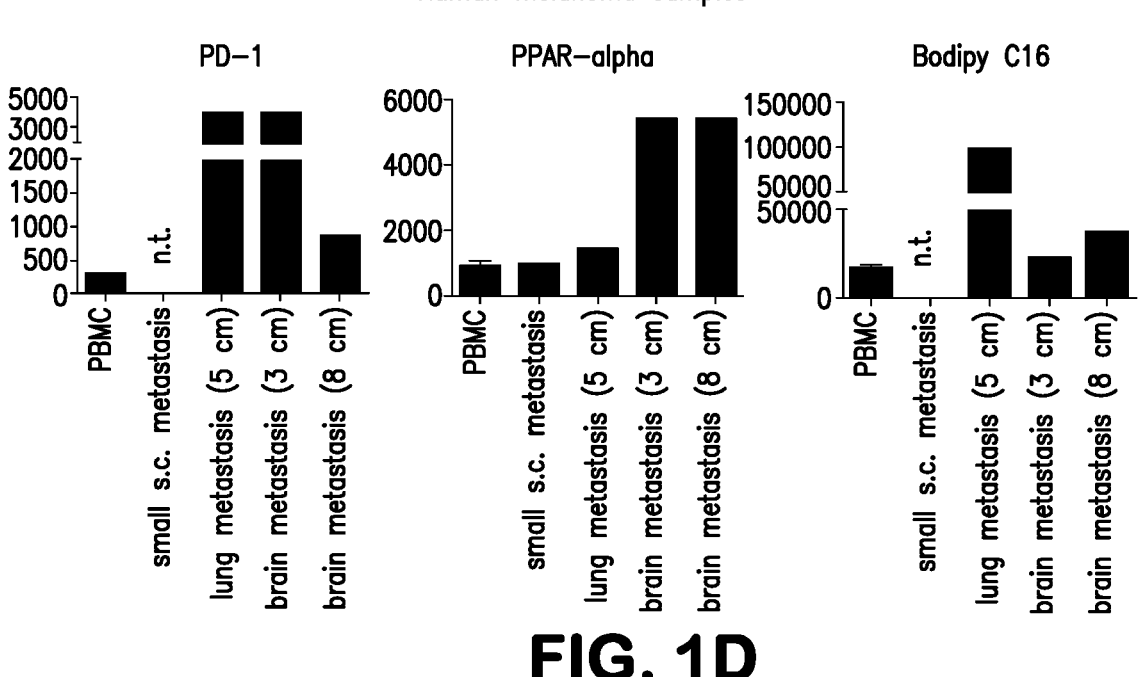
FIG. 1D shows 3 bar graphs of characteristics of human T cells in various cancers on expression of PD-1, PPAR-α, and Bodipy C16 for comparison with the studies herein.

In another experiment, graphs were generated showing MFI of CD62L, CD127, KLRG1 and Eomes on/in specific CD8+ T cells from spleens and tumors with representative histograms for Trp-1-specific CD8+ T cells and CD44−naive T cells (FIG. 1C). Levels of differentiation markers CD62L, CD127, KLRG1 and Eomes on/in vaccine-induced CD8+ T cells from spleens and tumors remained comparable. Thus, factors other than chronic antigen exposure contribute to CD8+TIL exhaustion.

Figure 2A:
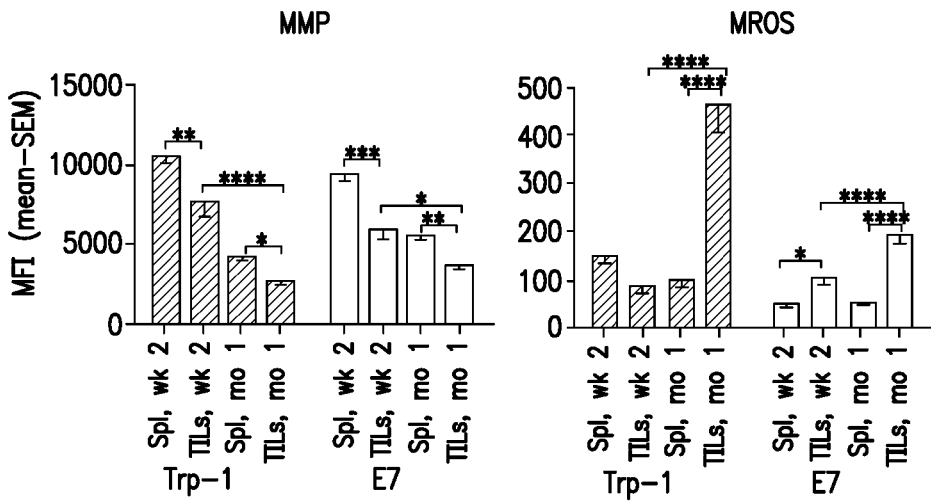
FIGS. 2A-2C illustrate that CD8+TILs increasingly experience metabolic stress within the TME.
Figure 2B:
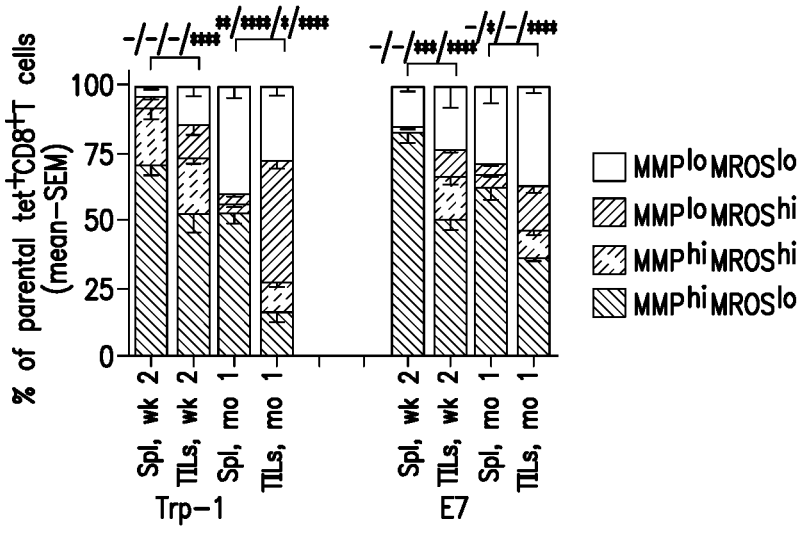

Metabolic stress dictates cellular fate[26,16,23] and potentially affects functions and survival of CD8+TILs independent of their antigen specificity. During tumor progression Trp-1- and E7-specific CD8+TILs gradually lose mitochondrial membrane potential (MMP) (FIG. 2A), which is essential for ATP production and increase levels of toxic mitochondrial reactive oxygen species (MROS). MMP$^{lo}$MROS$^{hi}$ Trp-1- and to a lesser extent E7-specific CD8+TILs become prevalent in late stage tumors (FIG. 2B), while corresponding CD8+ T cells from spleens remain largely MMP$^{hi}$MROS$^{lo}$. These data suggest that CD8+TILs increasingly experience metabolic stress within growing tumors.

As shown herein, continued stimulation seems to accelerate the impairment.

Figure 2C:
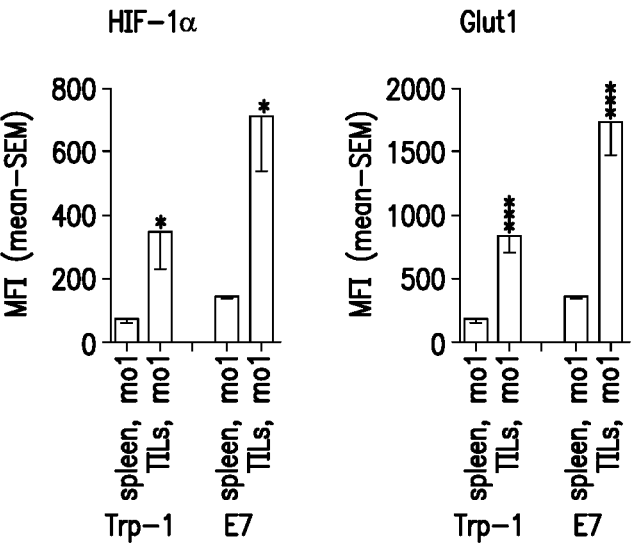

Example 3: Hypoxia Through HIF-1a Increases Lag-3 Expression and Reduces T Cell Functions Trp-1- and E7-specific CD8+TILs are progressively subjected to hypoxia during tumor progression as shown by their enhanced expressions of HIF-1a, a transcription factor that stabilizes under hypoxia, and its downstream target Glut1, which facilitates Glu uptake, in/on vaccine-induced CD8+TILs from 1-month (FIG. 2C), but not small 2-week tumors (data not shown).

To determine how hypoxia affects CD8+ T cells, we stimulated enriched, activated CD8+ T cells in vitro continuously for 96 hours under normoxia (21% $O_2$) or for the last 16 hours under hypoxia (1% $O_2$) Hypoxia reduces blast formation (FIG. 8A) and increases expression of HIF-1$\alpha$ and Glut1 (FIG. 8B). The $O_2$ consumption rate (OCR), a measure of OXPHOS, decreases under hypoxia while the extracellular acidification rate (ECAR), a measure of glycolysis, increases (FIG. 8C). The T cells' MMP decreases and MROS increases, leading to a rise in the proportion of MMPloMROShi CD8+ T cells (data not shown) reminiscent of the metabolic profile of vaccine-induced TILs in late-stage tumors. Hypoxia reduces PD-1 but augments LAG-3 expression (FIG. 8D), suggesting that PD-1 declines and LAG-3 increases upon enhanced glycolysis driven by HIF-1$\alpha$ signaling. CD8+ T cells cultured under hypoxia reduce T-bet expression (FIG. 8D), decrease production of effector molecules and lose polyfunctionality (FIG. 8E), indicating that hypoxia impairs CD8+ T cell functions.

An alternative previously described protocol (Doedens et al., 2013) that tests the effect of hypoxia on resting CD8+ T cells was conducted by stimulating T cells for 48 hours. The CD8+ T cells upon activation are switched to IL-2 containing medium without antibodies to CD3 or CD28 stimulation and maintained at a relatively resting stage in IL-2 prior to hypoxia. The effect of hypoxia was assessed by subjecting cells cultured in IL-2 to 1% $O_2$ for the last 36 hours. FIG. 8F shows blast formation; normalized % of live IL-2 maintained CD8+ T cells forming blasts under hypoxia (white) compared to those cultured under normoxia (dark gray) using this protocol. This protocol, has no effect on blast formation (FIG. 8F) or PD-1, although LAG-3 increases (FIG. 8G) and T-bet decrease (FIG. 8G). Granzyme B (GzmB) production increases while production of other effector molecules and polyfunctionality decline (FIG. 8H). As vaccine-induced CD8+ T cells are unlikely to rest before infiltrating hypoxic areas of a TME, we used the protocol of continuous CD8$^+$ T cell activation for subsequent hypoxia experiments.

Solid tumors commonly lack $O_2$. The data show that Trp-1- and E7-specific CD8+TILs within the TME increasingly experience hypoxia during tumor progression as shown by enhanced expressions of HIF-1$\alpha$, a transcription factor that stabilizes under hypoxia, and its downstream target Glut1, which facilitates Glu uptake, in/on vaccine-induced CD8+TILs from late-stage (FIG. 2C) but not small week 2 tumors (data not shown).

To test the effect of hypoxia, we stimulated CD8$^+$ T cells in vitro for 4 days in regular Glu-rich medium under normoxia (21% $O_2$) or subjected them to hypoxia (1% $O_2$) for the last 16 hours of culture. Hypoxia affects T cell stimulation as evidenced by reduced blast formation (FIG. 8A). CD8$^+$ T cells activated under hypoxia increase expression of HIF-1$\alpha$ and Glut1 (FIG. 8B). They become metabolically stressed as evidenced by decreases in MMP and rises in MROS, leading to an increase in the proportion of MMPloMROShi CD8$^+$ T cells (FIG. 8C) reminiscent of the mitochondrial metabolic profile of vaccine-induced TILs in late-stage tumors. Hypoxia reduces PD-1 but augments LAG-3 expression (FIG. 8D), suggesting that PD-1 declines and LAG-3 increases under conditions that promote glycolysis such as intensified HIF-1$\alpha$ signaling. CD8+ T cells cultured under hypoxia reduce T-bet expression (FIG. 8D), decrease production of effector molecules and lose polyfunctionality (FIG. 8E).

A different previously described protocol[10], in which CD8+ T cells upon the initial activation are rested in IL-2 prior to hypoxia, has no effect on blast formation (FIG. 8F) or PD-1 levels, although LAG-3 expression increases (FIG. 8G) and T-bet levels decrease (FIG. 8G). Granzyme B (GzmB) production increases while production of other effector molecules and polyfunctionality decline (FIG. 8H). As vaccine-induced CD8+ T cells are unlikely to rest before infiltrating tumors, we used the protocol of continuous CD8+ T cell activation for subsequent hypoxia experiments.

HIF-1$\alpha$ correlates with expression of LAG-3 on TILs or CD8+ T cells subjected to hypoxia. To determine whether HIF-1$\alpha$ directly promotes LAG-3 expression and whether this affects CD8+ T cell functions, we knocked down HIF-1$\alpha$ transcripts by transducing CD8+ T cells with lentivectors that express either short-hairpin (sh)RNA to silence HIF-1$\alpha$ or a control sequence, together with a Thy1.1 selection marker (data not shown). HIF-1$\alpha$ silencing/knockdown reduces expression of HIF-1$\alpha$ in CD8+ T cells stimulated in vitro under hypoxia (See FIG. 3A), concomitantly decreases LAG-3 but not PD-1 (see FIG. 3A) and improves production of GzmB and IFN-$\gamma$ (see FIG. 3B). HIF-1$\alpha$ positively correlates with expression of LAG-3 on TILs or CD8$^+$ T cells subjected to hypoxia.

To study whether HIF-1$\alpha$ contributes to the CD8+TILs' co-inhibitor expression and loss of functions, we activated enriched CD8+ T cells in vitro. The enriched CD8+ T cells were transduced with lentivectors (i.e., lentivirus-based vectors) expressing control or HIF-1$\alpha$ targeting shRNA and Thy1.1. The viruses were transferred i.v. into recipient mice which had been challenged with tumor cells 5 days earlier and been vaccinated with AdC68-gDMelapoly 2 days earlier (i.e., Thy1.2$^+$ tumor-bearing, AdC68-gDMelapoly-vaccinated mice).

Trp-1-specific Thy1.1$^+$CD8$^+$ T cells were recovered from tumors about 2 to 3 weeks after transfer. We analyzed the transferred T cells ~2-3 weeks later using samples from mice bearing similar sized tumors. Cells from tumors were first gated on mononuclear cells, singlets, live cells and CD8$^+$ T cells. They were further gated on Thy1.1$^+$ cells and Trp-1-tetramer$^+$CD44$^+$ cells.

Figures 3A, 3B:
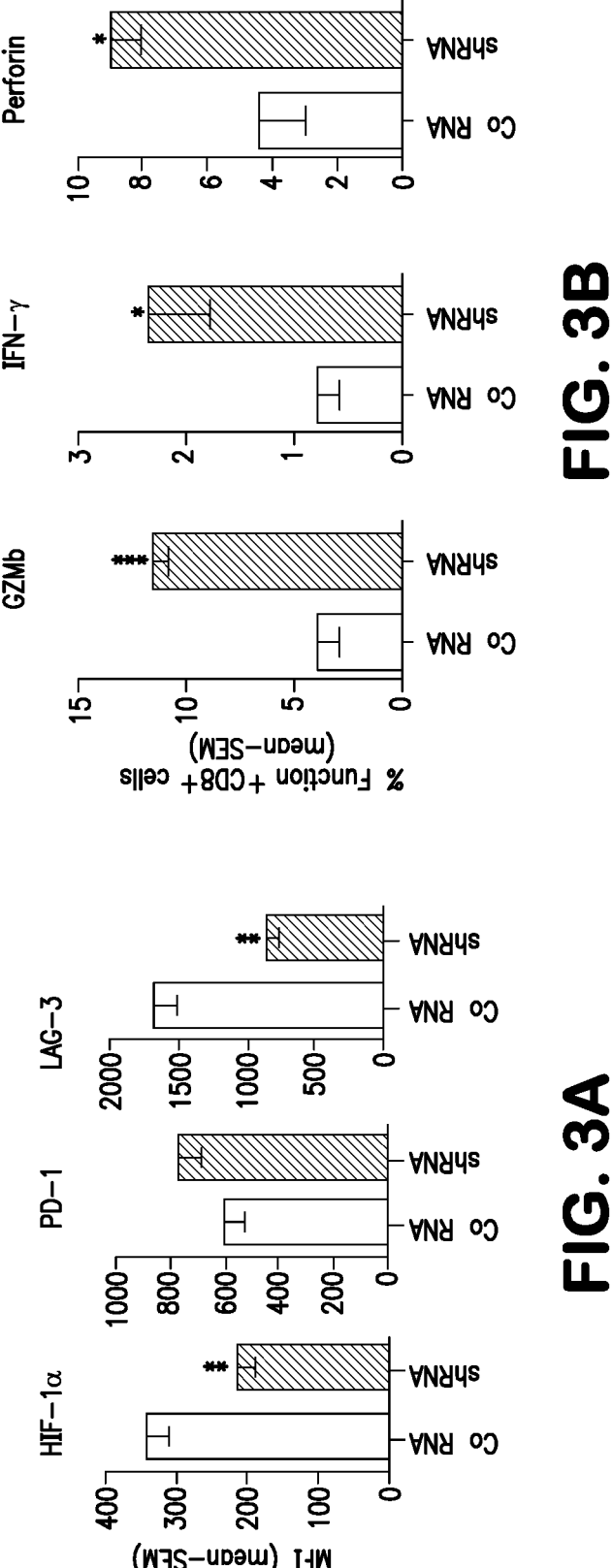
FIGS. 3A to 3C illustrate the effect of hypoxia on characteristics of activated CD8+ T cells. HIF-1α knock down reduces LAG-3 expression and improves melanoma associated antigen (MAA)-specific CD8$^+$ T cell functions.
Figure 3C:
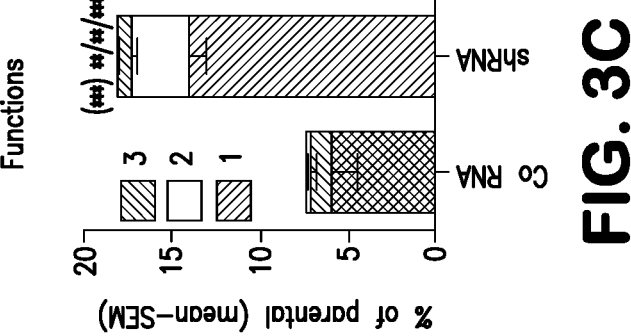

Knocking down HIF-1$\alpha$ (FIG. 3A) reduces the Trp-1-specific CD8+TILs' expression of LAG-3 without affecting PD-1 (FIG. 3A) and significantly improves the frequencies and effector functions of MAA-specific CD8+TILs (FIG. 3B). The T cells' frequencies and functions (FIG. 3C). Production of perforin increased upon HIF-1$\alpha$-silencing in vivo but not in vitro, which may reflect that other conditions such as differences in supply of nutrients contribute to the effect of hypoxia on activated CD8+ T cells. These data support that hypoxia through increased HIF-1α signaling directly enhances LAG-3 expression and dampens effector functions of CD8+TILs.

Collectively the data show that hypoxia through HIF-1α leads to functional impairment of activated CD8+ T cells. Hypoxia-induced HIF-1α directly drives co-inhibitor LAG-3 expression and impairs effector functions of activated CD8+ T cells in vitro. HIF-1a increases glucose uptake and enzymes of glycolysis. It reduces energy production through the TCA cycle by activating PDK1 which inactivates pyruvate dehydrogenase. Within a glucose poor environment increased HIF-1a signaling is counterproductive for TAA-specific CD8+ T cells. The data further suggest that a ing that the use of OXPHOS is linked to high PD-1 expression on activated CD8+ T cells (FIG. 91B-9C). Compared to cells cultured with Glu, those grown with limited access to Glu under both normoxia and hypoxia decrease T-bet expression (FIG. 9D) and lose functions (FIG. 9E). Poly-functions of CD8+ T cells without access to Glu are better preserved if cells are also subjected to hypoxia (FIG. 9D). These data suggest that under hypoxia cells with limited supply of Glu may more adjust their metabolism to support their functions.

Figure 4A:
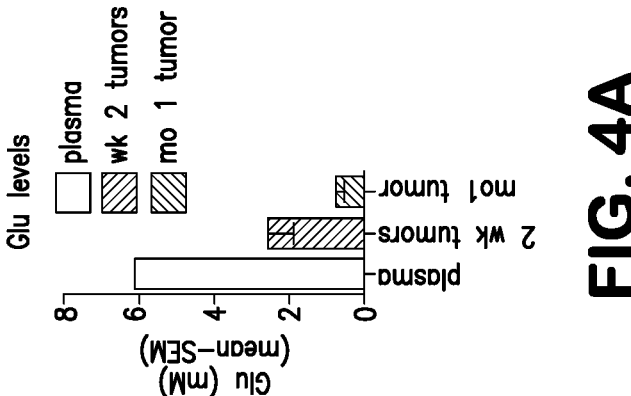

To study the metabolic pathways used by CD8+ T cells with limited Glu and $O_2$ supply, we measured transcripts for factors that participate in nutrient consumption and energy production by quantitative Real-Time (qRT) PCR (FIG. 15F, FIG. 4B and Table 2).

TABLE 2

| Function | Name | Abbreviaton |
|---|---|---|
| Glucose uptake | glucose transporter 1 | Glut1 |
| Glycolysis | hexokinase 2 | Hk-2 |
| | phosphoglycerate kinase | Pgk1 |
| TCA cycle | isocitrate dehydrogenase subunit alpha | Idh3a |
| | monodehydroascorbate reductase 2 | Mdh2 |
| Regulation of FA me 1 abolism | peroxisome proliferator-activated receptor alpha | Ppar-α |
| FA transport | solute carrier family 27a4 | Slc27a4 |
| | solute carrier family 27a2 | Slc27a2 |
| Triglyceride (TG) synthesis | Diacylglycerol-O-acyltransferase 1 | Dgat1 |
| | Diacylglycerol-O-acyltransferase 2 | Dgat2 |
| Triglyceride (TG) catabolism | Lipase A | Lipa |
| | patatin-like phospholipase domain containing 2 | Pnpla2 |
| Peroxisomal FAO | acetyl-CoA acyltransferase 1 | Acaa1a |
| | CoA dehydrogenase | Ehhadh |
| | acyl-CoA oxidase 1 | Acox1 |
| | hydroxysteroid (17-beta) dehydrogenase 4 | Hsd17b4 |
| Mitochondrial FAO | carnitine palmitoyltransferase 1a | Cpt-1a |
| | acyl-CoA dehydrogenase, very long chain | Acadvl |
| | acyl-CoA dehydrogenase, C4 to C12 straight chain | Acadm |
| Metabolism of ketone bodies | 3-hydroxybutyrate dehydrogenase 1 | Bdh1 |
| ROS metabolism | NADPH oxidase 1 | Nox1 |
| | superoxide dismutase 1 | Sod1 |
| | catalase | Cat |
| Electron transport chain | cytochrome c oxidase subunit Vb | Cox5b |

HIF-1α-driven metabolic switch to glycolysis is counter-productive for T cell functions within an $O_2$ and Glu-depleted TME.

Example 4: Activated CD8+ T Cells Lacking Both Glu and $O_2$ Enhance FA Catabolism Not only $O_2$ but also Glu declines within the TME during tumor progression presumably due to its consumption by tumor cells. The collective effects of hypoglycemia and hypoxiaon activated CD8+ T cells were studied by stimulating them in vitro in Glu medium with 2-deoxy-D-glucose (2-DG), a glycolysis inhibitor. Alternatively, Glu was replaced by galactose (Gal). Cells were cultured under normoxia or short-term hypoxia. The extracellular acidification rate (ECAR), a measure of glycolysis, declines in T cells cultured with 2-DG or Gal.

The $O_2$ consumption rate (OCR), a measure of OXPHOS, decreases in T cells cultured with 2-DG but increases in the presence of Gal (FIG. 9A). Either condition augments the OCR/ECAR ratio, suggesting increased energy production through OXPHOS Cells cultured with 2-DG or Gal compared to those grown with Glu express more PD-1, suggest- Upon short-term hypoxia CD8+ T cells stimulated with limited access to Glu compared to those stimulated in Glu-rich medium decrease transcripts for enzymes of glycolysis, the tricarboxylic acid (TCA) cycle, ROS detoxification, and the electron transport chain (ETC), but increase transcripts for receptors and enzymes of FA uptake, triglyceride TG turnover, peroxisomal and mitochondrial FA catabolism.

This pattern is closely mirrored by Trp-1- and E7-specific CD8+TILs from 1-month tumors compared to those from small 2 week-old tumors, indicating that metabolically stressed CD8+ T cells increasingly rely on FA catabolism. Changes in transcripts during tumor progression are not driven by differentiation of TILs towards a more resting stage, as they are distinct from differences in vaccine-induced splenic CD8+ T cells tested at 3 months vs 2 weeks after vaccination.

To directly measure effects of Glu and $O_2$ deprivation on CD8+ T cell metabolism, we analyzed the intensity of metabolites by lipid chromatography-mass spectrometry (LC-MS). Metabolites involved in FA mitochondrial transport and catabolism, i.e., acetylcarnitine, palmitoylcarnitine and the ketone body 3-hydroxybutyrate, increase in cells stimulated in vitro in Gal medium and this is further enhanced under hypoxia (FIG. 10A). $^{13}C_6$-Glu/Gal or $^{13}C_{16}$-palmitate isotope tracing show that CD8+ T cells activated in Glu medium and short-term hypoxia or in medium with limited access to Glu under normoxia or hypoxia compared to those activated in Glu medium under normoxia have reduced carbohydrate-derived TCA cycle metabolites (FIG. 10B). $^{13}C_{16}$-palmitate-derived carbons are increasingly incorporated into acetyl-CoA and TCA cycle metabolites (FIG. 10C). Moreover, cells stimulated under hypoxia show higher percentages of $^{13}C_{16}$-palmitate-derived acetyl-CoA than those cultured in the same medium under normoxia, suggesting that hypoxia further increases fatty acid catabolism. This is also supported by increased FA uptake (FIG. 10D) and enhanced oxidation of endogenous and exogenous FAs (FIG. 10E) by CD8+ T cells activated with limited access to Glu and/or $O_2$. These data indicate that activated CD8+ T cells deprived of Glu increasingly rely on FA catabolism to produce energy through OXPHOS. Surprisingly although OXPHOS requires $O_2$, hypoxia increases this metabolic switch.

We next studied the metabolism of activated CD8+ T cells directly in vivo by stable isotope tracing. Mice bearing 3-day tumors were vaccinated with AdC68-gDMelapoly and AdC68-gDE7. Two weeks or one month later mice were given $^{13}C_6$-Glu i.p. 30 minutes later, TILS are isolated, and CD8+CD44+ cells are isolated and their metabolites analyzed. Levels of glycolysis metabolites and $^{13}C$ incorporation into TCA cycle intermediates were analyzed in CD44+ CD8+ T cells from spleen and tumors. The intensity of glycolysis intermediates glucose-6-phosphate (G6P) and 3-phosphoglycerate (3PG) in TILs declines during tumor progression (FIG. 4C), indicating reduced glycolysis. The contribution of Glu-derived carbon to TCA cycle intermediates declines comparing CD44+CD8+ T cells from late to early stage tumors or from tumors to spleens (FIG. 4D), confirming that TILs decrease Glu catabolism.

Figure 4E:
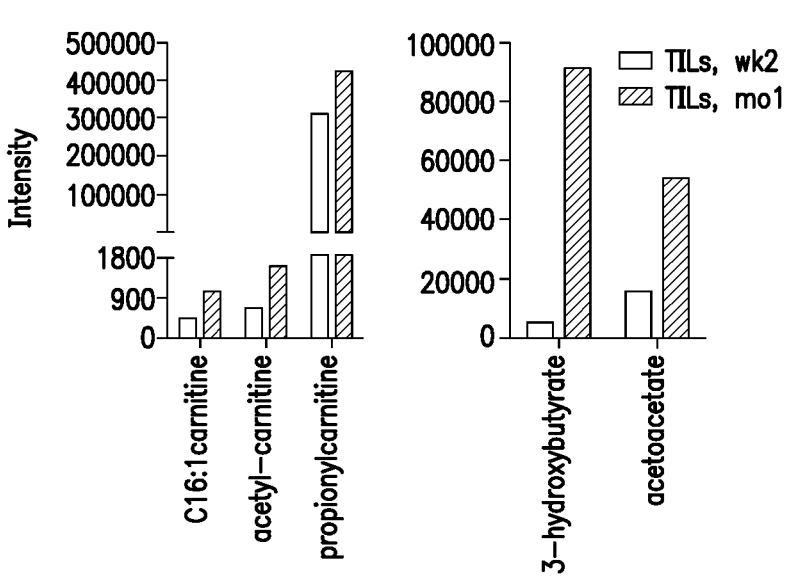

We further performed $^{13}C_{16}$-palmitate tracing in mice bearing 2-week or 1-month tumors. Mice were administered $^{13}C_{18}$-palmitate-BSA per os/i.v. Sixty minutes after feeding and 30 minutes after injection, the TILS were isolated and the CD8+CD44+ cells were isolated and metabolites analyzed. The intensities of acylcarnitine species, the ketone bodies 3-hydroxybutyrate and acetoacetate increase in TILs during tumor progression (FIG. 4E). Moreover, the contribution of $^{13}C_{16}$-palmitate-derived $^{13}C$ to TCA metabolites becomes higher in CD44+CD8+ T cells from 1-month tumors compared to those from 2-week tumors or 1-month spleens (FIG. 4F), supporting the TILs' enhanced reliance on FA catabolism during tumor progression. In splenic CD44+CD8+ T cells tested at different time points after vaccination, $^{13}C_{16}$-palmitate-derived carbon incorporation into TCA cycle metabolites remains stable or decreases over time. CD62L and CD127 expression are markedly lower on CD44+CD8+TILs from 1-month compared to those from 2-week tumors (data not shown), confirming the enhanced FA catabolism by late-stage CD8+TILs is not reflective of their differentiation towards memory.

The metabolic switch of TILs towards FA catabolism is facilitated by high abundance of different free FA species within the melanoma interstitial fluid (FIG. 4G), enhanced uptake of FAs (FIG. 4H) and increased expression of the FA oxidation (FAO) rate-limiting enzyme Cpt1a (FIG. 4I) in vaccine-induced CD8+ T cells from late stage tumors.

Figure 4F:
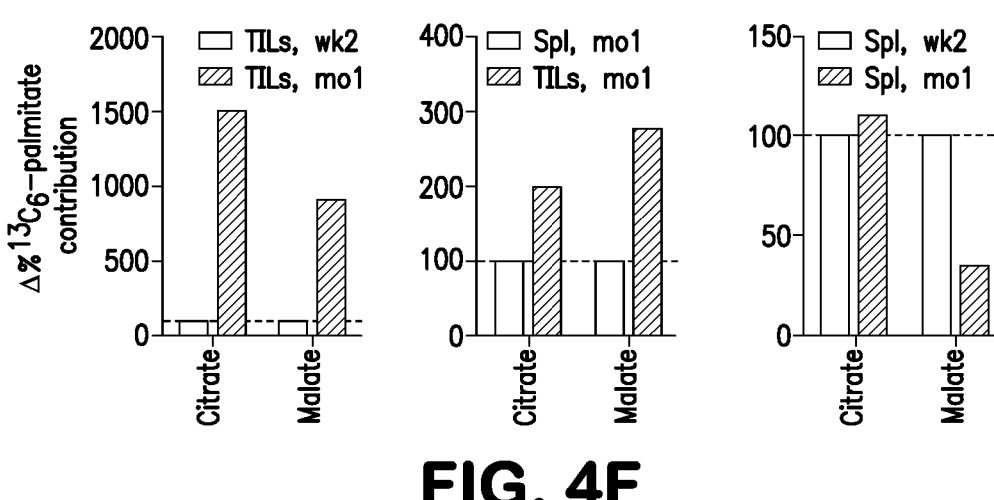
Figure 4G:
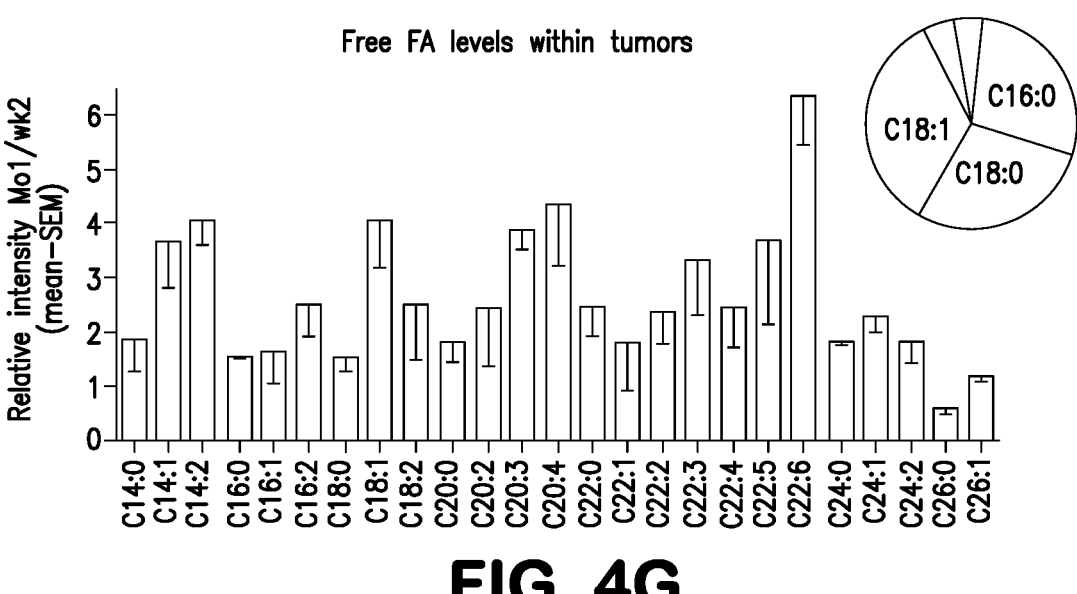
Figure 4H:
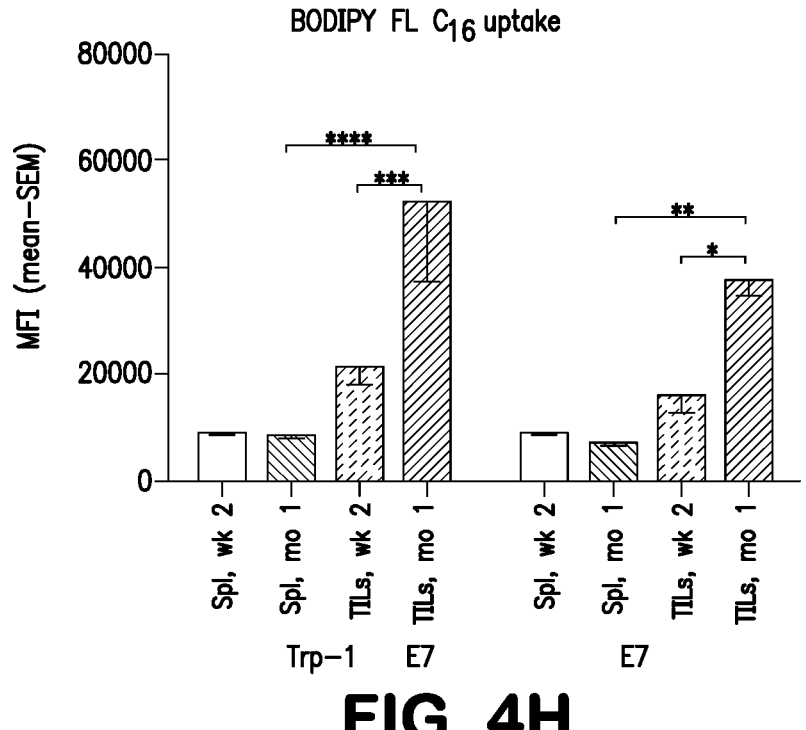
Figure 4I:
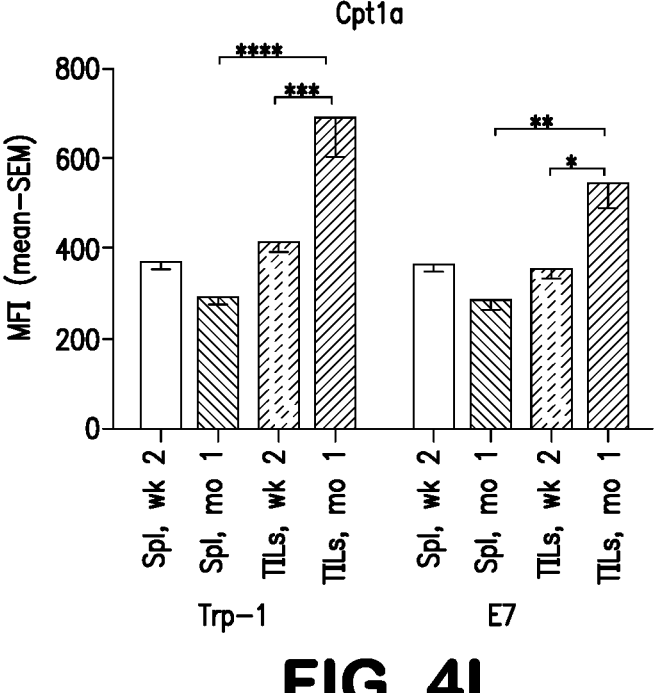

Trp-1- and E7-specific TILs from late-stage tumors increase FA uptake (FIG. 4H) and expression of the fatty acid catabolism rate-limiting enzyme Cpt1a (FIG. 4I) compared to TILs from early tumors or corresponding T cells from spleens suggesting their increased reliance on FA catabolism. Both FA uptake and Cpt1a levels remain low and comparable in CD8+ T splenocytes induced by vaccination 2 weeks or 1 month earlier, suggesting metabolic changes observed in TILs are not due to their differentiation towards a more resting 'memory' stage. Comparisons of FA metabolites show higher levels of acyl-carnitine species and the ketone body acetoacetate in CD44+CD8+TILs form late-compared to early-stage tumors (FIG. 4E). $^{13}C$ contribution from $^{13}C_{16}$-palmitate to TCA metabolites increases in CD44+CD8+TILs during tumor progression (FIG. 4G), further supporting their enhanced reliance on fatty acid catabolism. In splenic CD44+CD8+ T cells tested at different times after vaccination, $^{13}C_{16}$-palmitate derived $^{13}C$ incorporation into citrate or malate remains stable or decreases over time (FIG. 4F).

This data show that vaccine-induced CD8+TILs in late-stage tumors enhance co-inhibitors PD-1 and LAG-3 expression, lose effector functions and polyfunctionality, experience enhanced metabolic stress and decrease glucose metabolism and increasingly rely on FA catabolism.

Overall these data strongly indicate that CD44+CD8+ T cells deprived of Glu increasingly rely on FA catabolism to produce energy through OXPHOS. Surprisingly this further increases upon hypoxia, although OXPHOS requires $O_2$.

Figure 6A:
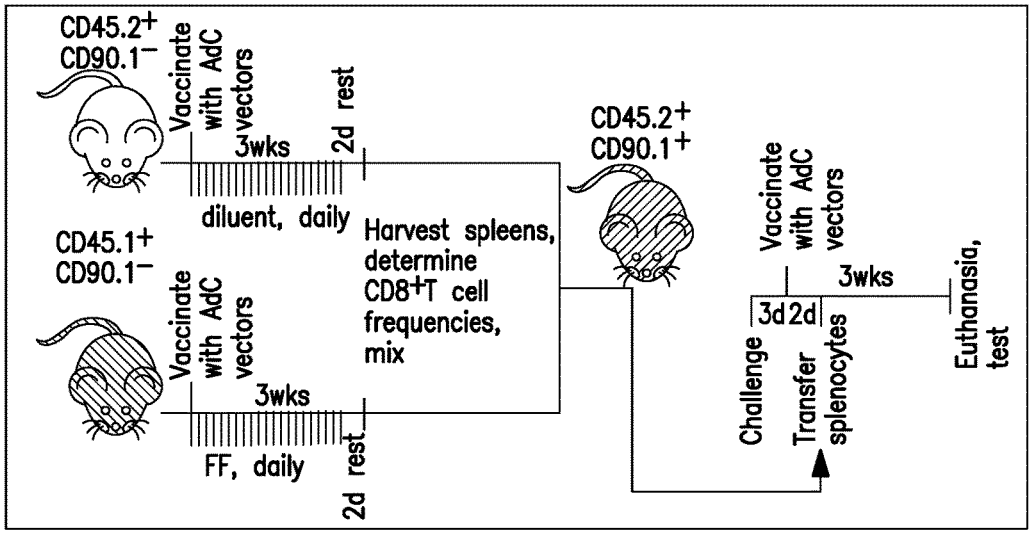
FIGS. 6A-6J illustrate that promoting FA catabolism improves CD8+TIL functions without reducing PD-1 expression.

Example 5: Enhanced Reliance on FA Catabolism Increases PD-1 Expression and is Essential to Maintain CD8+ T Cell Functions Under Metabolically Stressed Condition To further assess the impact of FA catabolism on CD8+ T cell differentiation, we stimulated CD8+ T cells in presence of fenofibrate (FF), an agonist of PPARα that enhances FA catabolism, or etomoxir (Eto), an irreversible inhibitor of Cpt1 that decreases mitochondrial fatty acid catabolism (FIG. 6A). In vitro FF-treated cells stimulated in Glu or Gal medium compared to diluent-treated cells increase fatty acid catabolism as shown by their enhanced transcripts of factors involved in FA catabolism (data not shown) and increased FA uptake (FIG. 12A). CD8+ T cells stimulated in either Glu or Gal media decrease OCR in presence of Eto (FIG. 12B), confirming the drug's inhibitory effect on fatty acid catabolism. OCR declines more in cells cultured with Gal and Eto, and further decreases when cells are also subjected to hypoxia, again confirming the cells' increased reliance on fatty acid catabolism when Glu and $O_2$ are limited. Under hypoxia PD-1 increases with addition of FF but decreases in presence of Eto (FIG. 12C). FF increases while Eto decreases functions and polyfunctionality of CD8+ T cell cultured with limited access to Glu and O2. These results show that FA catabolism promotes PD-1 expression and effector functions of metabolically stressed CD8+ T cells.

As shown in FIG. 4B, T cells experiencing metabolic stress increase transcripts of enzymes participating in TG turnover. To assess if CD8+ T cells under such conditions mobilize TGs to fuel fatty acid catabolism and OXPHOS, we added Orlistat (OS), an inhibitor of the lipolysis enzyme lipa, or Amidepsine A (AmA), an inhibitor of the TG synthesis enzymes Dgat1 and Dgat2, to CD8+ T cells stimulated under different conditions (FIG. 6A). Basal OCR decreases in CD8+ T cells cultured with either drug in Glu or Gal media (data not shown) under short-term hypoxia, suggesting that TG turnover provides fuels for OXPHOS. Under hypoxia PD-1 decreases with addition of OS regardless of other culture conditions and with addition of AmA to Gal medium (FIG. 12C). AmA and to a lesser degree OS decrease functions of T cells cultured in Gal media and subjected to hypoxia. These data indicate that T cells activated under hypoxia use substrates from TG turnover for OXPHOS as OCR decreases in presence of AmA or OS. However TGs are not essential for effector functions unless CD8+ T cells are concomitantly subjected to hypoglycemia.

Figure 5A:
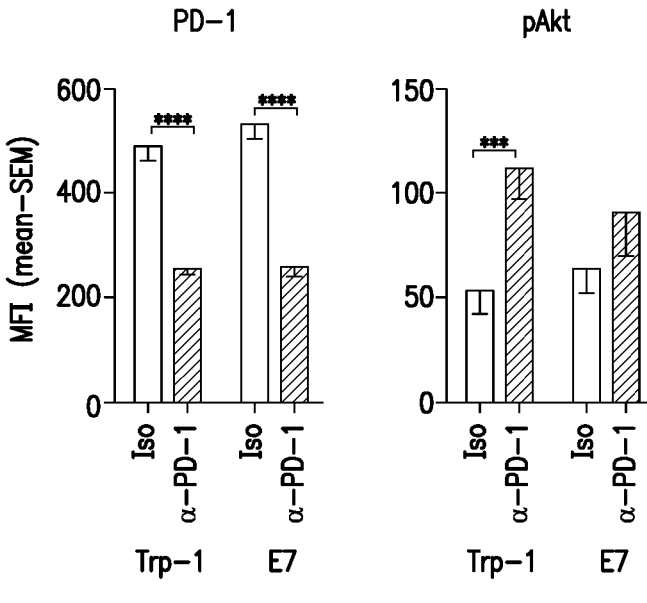
FIGS. 5A to 5F show that metabolism and effector functions of CD8+TILs are independent of PD-1. Tumor-bearing mice vaccinated on day 3, were treated with isotype or anti-PD-1 starting on day 10 after vaccination. Vaccinated tumor bearing mice were treated with isotype control (Iso) or anti-PD-1 antibody ($\alpha$-PD-1) every 3rd day.
Figure 5C:
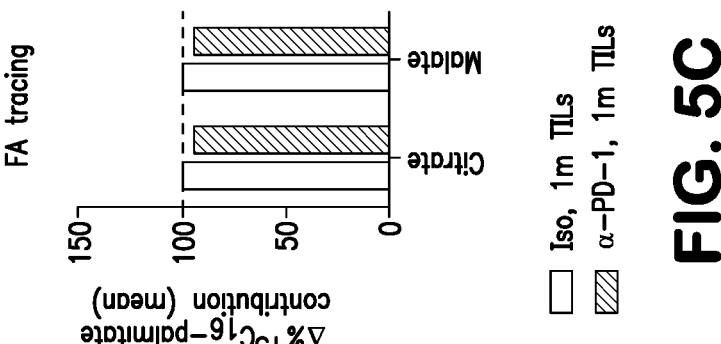
Figure 5B:
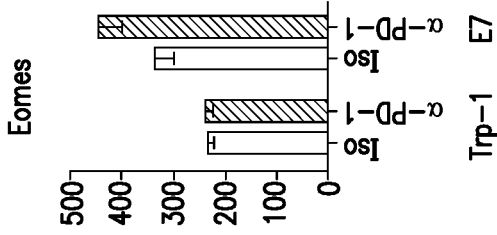
Figure 5B:
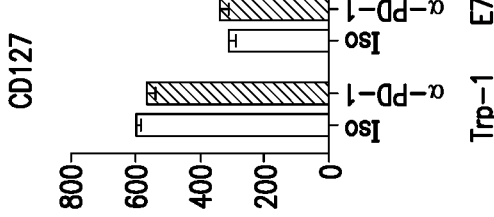
Figure 5B:
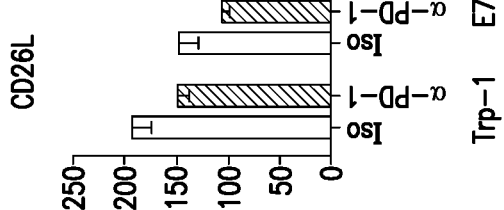
Figure 6B:
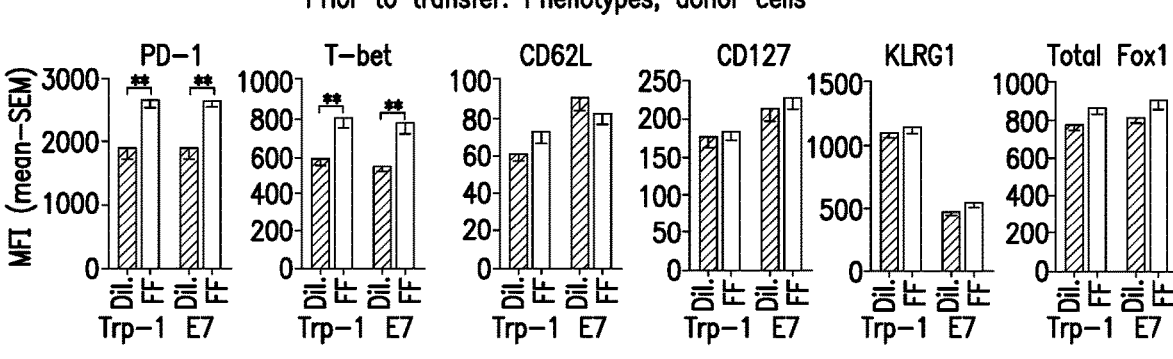
Figure 6E:
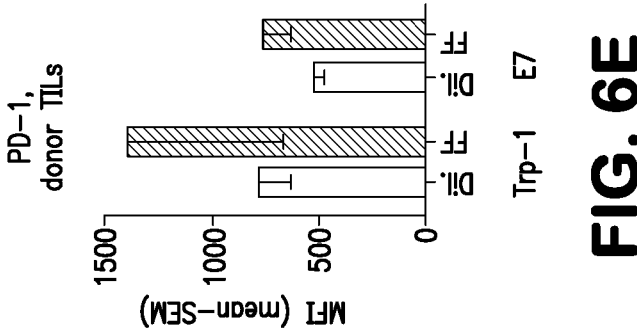
Figure 6D:
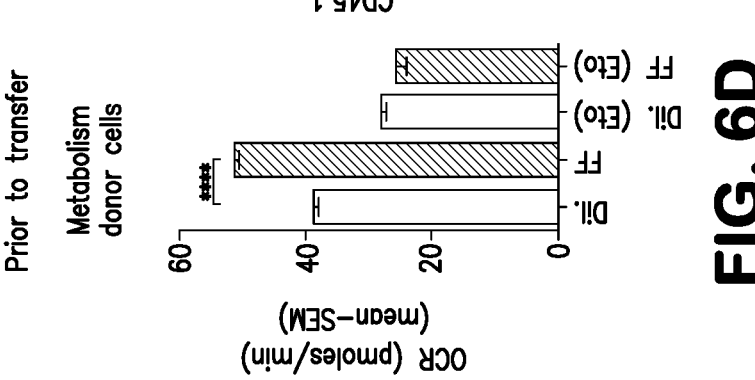
Figure 6C:
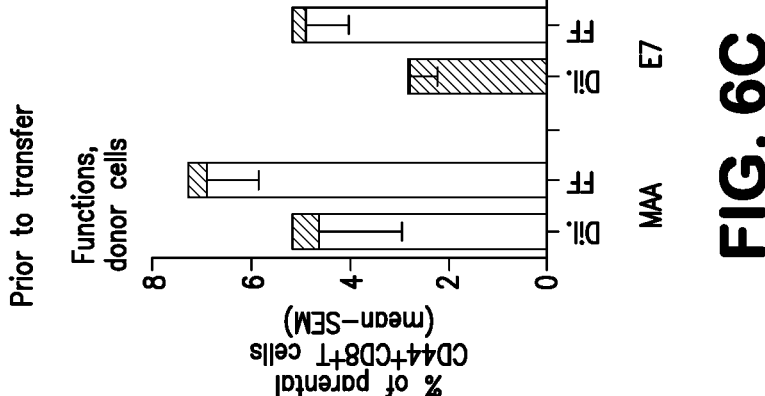
Figure 6F:
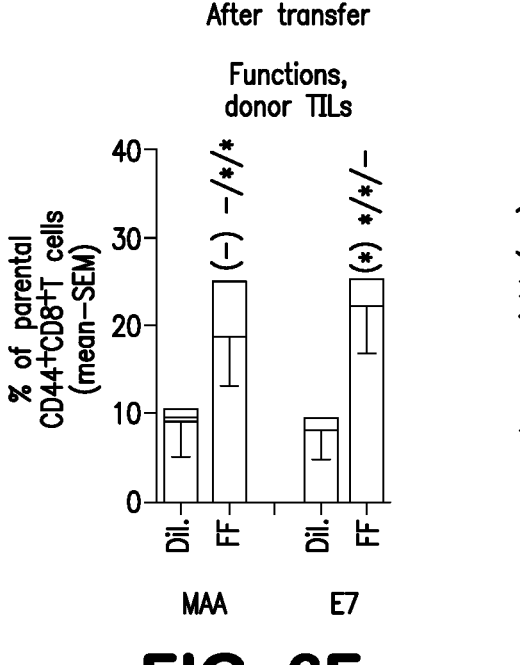
Figure 6G:
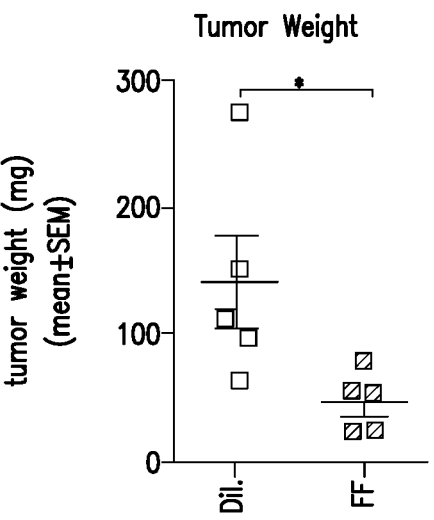

To assess how increased FA catabolism affects CD8+TIL functions, we vaccinated mice expressing CD90.2 and congenic for CD45, and treated them for 3 weeks daily with FF (CD45.1 mice) or diluent (CD45.2 mice). Splenocytes from these groups were mixed such that Trp-1-specific CD8+ T cells were present at equal numbers. The mixture was transferred into CD90.1+ recipient mice, which had been challenged with tumor cells and vaccinated 3 days later. Cells were transferred 2 days after vaccination (FIG. 5B). Immediately before transfer FF and diluent-treated Trp-1- and E7-specific CD8+ T cells from donor mice have similar functions with comparable surface expression of CD127, indicating that FF does not affect T cell activation or memory formation. FF-treated CD8+ T cells before transfer enhance OCR, which is blocked by Eto, indicating that FF conditions vaccine-induced CD8+ T cells to enhance fatty acid catabolism. Donor-derived vaccine-induced CD8+TILs were analyzed 3 weeks after transfer (data no shown). Compared to control-treated donor TILs, FF-treated donor-derived CD44+CD8+TILs show enhanced levels of transcripts for factors involved in lipid metabolism and increased PD-1 expression that reaches significance for Trp-1 specific cells. In addition, frequencies and functions of Trp-1- and E7-specific CD8+TILs originating from FF-treated donor exceed those from control donors. When transferring splenocytes of FF- or diluent-treated mice into separate cohorts of tumor-bearing mice, the former significantly delay tumor growth (FIG. 6G). Collectively these data confirm that enhanced FA catabolism increases PD-1 expression on TA-specific TILs, while preserving their functions.

To further study whether FA catabolism maintains functions of metabolically stressed CD8+ T cells, we stimulated CD8+ T cells from PPARα KO mice in vitro and compared them to those from wildtype (wt) mice. Transcripts for most factors involved in the TCA cycle and lipid metabolism are higher in PPARα KO compared to wt CD8+ T cells when stimulated in Glu medium and under hypoxia. This profile reverses in cells cultured in Gal medium and low $O_2$, suggesting that inactivation of PPARα significantly decreases FA catabolism of CD8+ T cells cultured without Glu (data not shown). PPARα KO compared to wt CD8+ T cells express lower levels of PD-1 when cultured with Gal-medium regardless of $O_2$ levels (FIG. 13A). Their functions are lower compared to those of wt CD8+ T cells cultured under the same conditions (FIG. 13B), supporting that FA catabolism is required to maintain effector functions of CD8+ T with limited access to Glu.

Figure 7A:
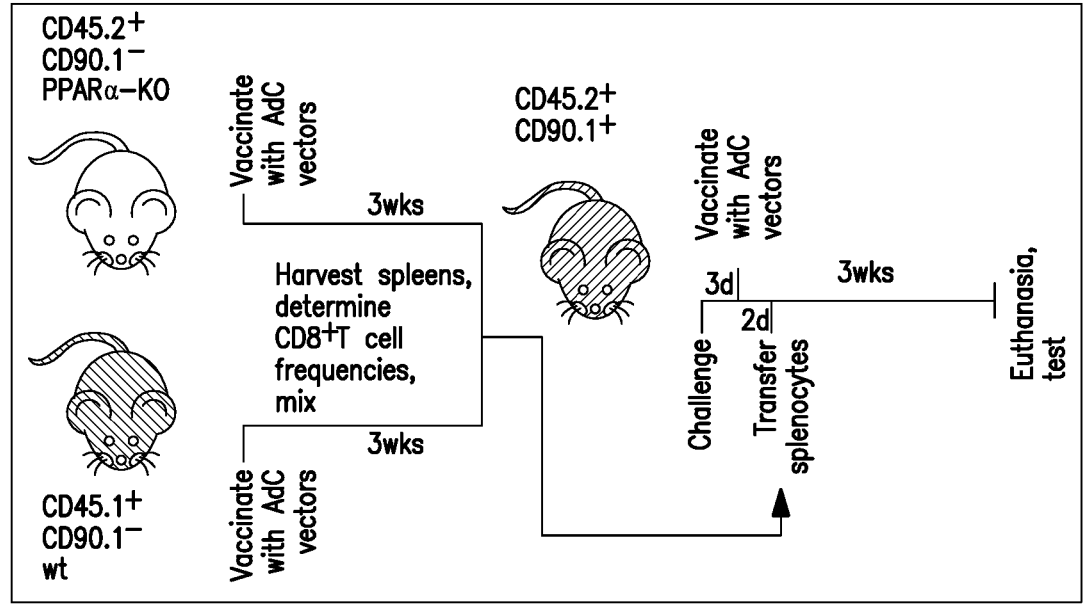
FIGS. 7A-7C illustrate that reducing FA catabolism decreases PD-1 expression and impairs CD8$^+$TILs.
Figure 7C:
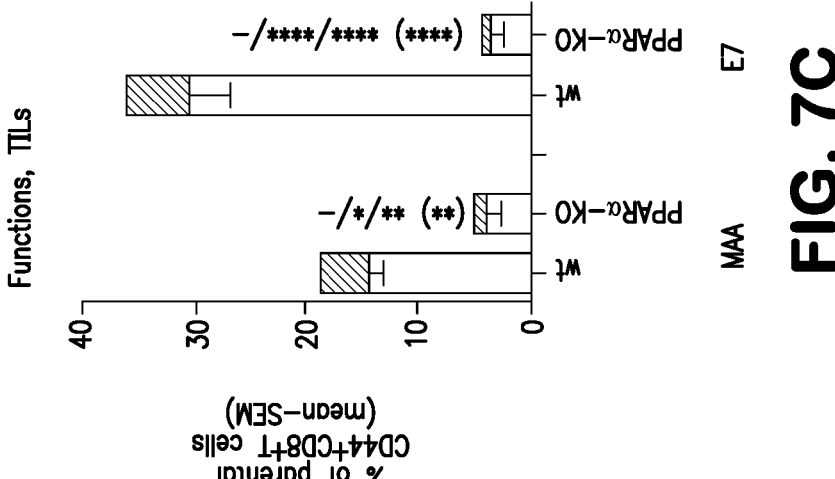
Figure 7B:
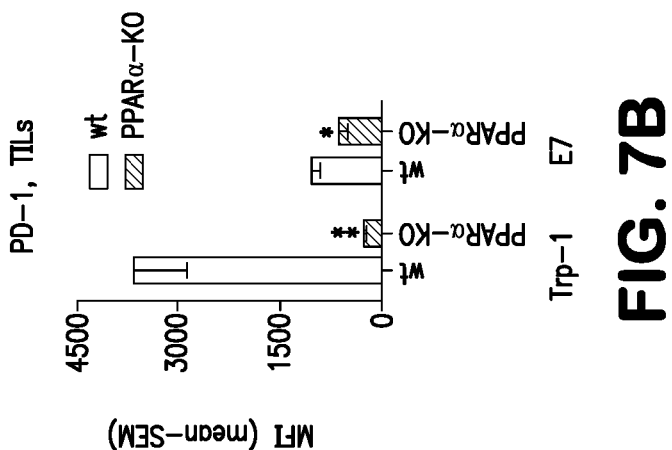

To further explore the effect of FA catabolism on vaccine-induced TILs, we used an adoptive transfer system, in which splenocytes from PPARα KO and wt CD45 congenic mice were co-transferred 3 weeks after vaccination into tumor-bearing and vaccinated recipient mice (FIG. 7A). Functions of Trp-1- and E7-specific CD8+ T cells from spleens of wt and PPAR-α KO mice as % of cells producing 3, 2 and 1 factors right before transfer were determined (data not shown). Prior to transfer, functions and polyfunctionality of Trp-1-specific CD8+ T cells are similar between the two groups, while E7-specific CD8+ T cells are less abundant and polyfunctional in PPARα KO mice. FA catabolism of CD8+TILS is decreased through PPAR-α knockout. This may reflect that strength of TcR signaling, which is lower for the E7 epitope, affects to what degree and at what time after activation cells rely on fatty acid catabolism. Expression of CD127 is comparable between the two T cell subsets, indicating no major differences in memory formation (histograms not shown). A heatmap comparing transcripts of TCA cycle and lipid catabolism enzymes catabolism enzymes in CD44$^+$CD8$^+$TILs derived from PPAR-α KO and wt donor mice 3 wk post transfer (n=3-4 samples/group) was review (data not shown) and CD44+CD8+TILs from PPARα KO as compared to wt donors collected from recipient mice 3 weeks after transfer show a transcriptional profile similar to that of CD8+ T cells cultured in vitro in Gal medium under hypoxia. This indicates reduced FA catabolism by PPARα KO-derived CD8+TILs. They show lower levels of PD-1 expression concomitant with decreases in frequencies and functions including polyfunctionality (FIGS. 7B, 7C). Collectively these data confirm that FA catabolism promotes PD-1 expression but preserves CD8+ T cell effector functions upon metabolic stress.

Example 6: Treatment with Anti-PD-1 Slows Tumor Progression without Changing CD8+ TILs' Metabolism or Functions In clinical trials checkpoint inhibitors such as monoclonal antibodies (mAb) to PD-1 can delay tumor progression (Larkin et al., 2015). As in the model CD8+TILs increase PD-1 expression over time, we tested if treatment with anti-PD-1 mAb affects their metabolism or functions.

Figure 5F:
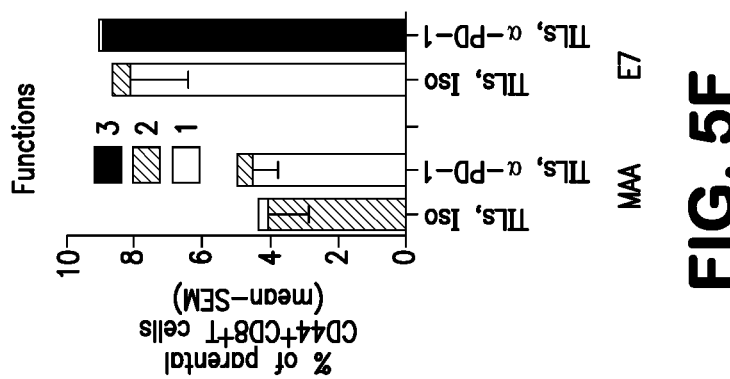
Figure 5E:
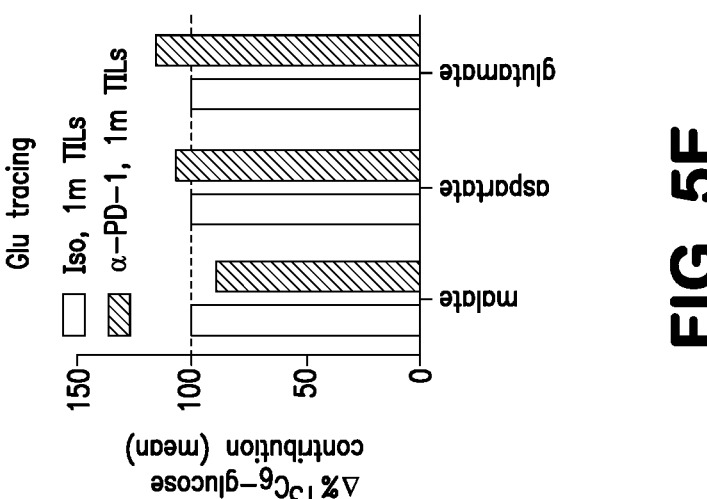
Figure 5D:
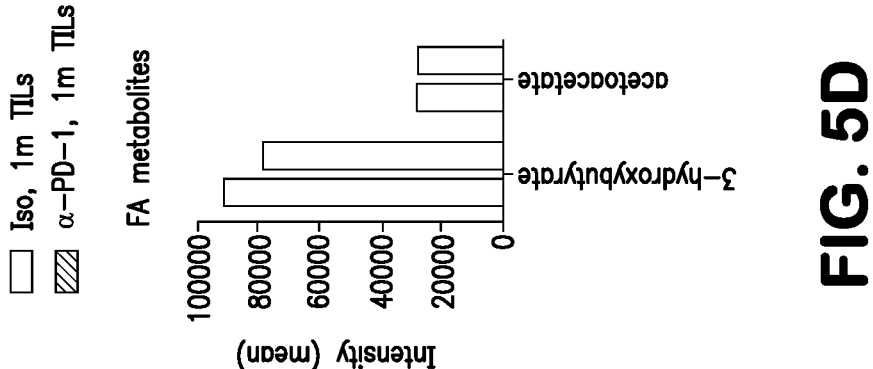

Mice were challenged with tumor cells, vaccinated 3 days later, and starting 10 days after vaccination treated with anti-PD-1 mAb or isotype control. Within 1-month tumors, anti-PD-1 treatment reduces staining for PD-1 and enhances pAkt levels on/in vaccine induced CD8+TILs (FIG. 5A) (Patsoukis et al., 2013) without affecting their differentiation status (FIG. 5B). PD-1 blockade neither dramatically affects the FA or Glu catabolism of CD44+CD8+TILs (FIGS. 5C, 5D and 5E) nor improves effector functions of vaccine-induced CD8+TILs (FIG. 5F).

Graphs (not shown) of tumor growth in vaccinated C57Bl/6 mice vs. unvaccinated C57Bl/6 mice and immune-deficient NSG mice, which lack T, B and natural killer cells mice show that PD-1 blockade does not affect CD8+TILs' functions, but it delays tumor progression although independent of T cells. It does effectively delay tumor progression in vaccinated as well as unvaccinated or even NSG mice, suggesting that PD-1 checkpoint blockade delays tumor progression in a T cell-independent manner.

Recent studies show that anti-PD-1 treatment decreases tumor progression by reducing mTOR signaling in PD-1+ melanoma cells (Kleffel et al., 2015). As mTOR signaling increases the T cells' Glu metabolism (Palmer et al., 2015), we tested whether anti-PD-1 mAbs reduce the tumor cells' Glu metabolism and thereby delay their growth. In all three models, anti-PD-1 treatment increases Glu content within the tumors' interstitial fluid (FIG. 11A). Cells from B16BrafV600E tumors of NSG mice upon anti-PD-1 treatment increase incorporation of Glu-derived carbons into metabolites of the TCA cycle or the purine synthesis pathway, indicating that PD-1 blockade actually increases their use of Glu for both catabolic and anabolic reactions (FIGS. 11B, 11C).

Anti-PD-1 cause delays in tumor progression in absence of CD8+ T cells, possibly because of blockade of reverse signaling. Ligation of PD-1 to PDL1 on tumor cells increases their resistance to apoptosis or T cell mediated cytolysis. (FIG. 11D).

In summary, PD-1 blockade provides clinical benefits to cancer patients presumably by rescuing T cell functions. In our model, conditions that decrease PD-1, e.g., hypoxia, decrease T cell functions; while fenofibrate increases PD-1 expression but results in improved T cell function. PD-1 may be helpful in a glucose-poor environment by reducing the T cells' reliance on glycolysis and thus preserving their functions. In the model PD-1 signaling has no major effects on metabolism or functions of CD8+TILs. Anti-PD-1 treatment could reduce tumor progression in a T cell independent manner.

Combining metabolic reprogramming with PD-1 blockade is one embodiment of a useful method of treatment.

Example 7: Enhanced Reliance on FA Catabolism is Essential to Maintain Functions of CD8+ T Cells To further assess the impact of FA catabolism on CD8+ T cell functions, we stimulated CD8+ T cell in presence of fenofibrate (FF), an agonist of PPARα that increases FA catabolism, or etomoxir (Eto), an irreversible inhibitor of Cpt1 that decreases mitochondrial FAO. In vitro FF-treated cells stimulated in Glu or Gal medium compared to diluent-treated cells increase FA catabolism as shown by their enhanced transcripts of factors involved in FA catabolism (PPAR-α, Ehhadh, Acox1—strongly increased for Glu, Cpt1a and Bdh1 also increased for Glu; Ehhadh and Cpt1a strongly increased—increased for Gal and PPAR-α, Acox1 and Bdh-1 also increased; data not shown) and increased FA uptake (FIG. 12A). Eto decreases OCR by CD8+ T cells stimulated in either Glu or Gal media (FIG. 12B). OCR declines more in cells cultured with Gal and Eto, and further decreases when cells are also subjected to hypoxia, again confirming the cells' increased reliance on FAO when Glu and $O_2$ are limited. Under hypoxia, PD-1 expression increases upon addition of FF but decreases in presence of Eto (FIG. 12C). FF increases while Eto decreases functions and polyfunctionality of CD8+ T cell cultured with limited access to Glu and $O_2$ (FIG. 12D). These results show that enhanced FA catabolism promotes effector functions of metabolically stressed CD8+ T cells, although it increases PD-1 expression.

To assess how increased FA catabolism affects CD8+TIL functions, we vaccinated CD90.2+ mice congenic for CD45, and treated them for 3 weeks daily with FF (CD45.1 mice) or diluent (CD45.2 mice). Splenocytes from these mice were mixed at a 1:1 ratio of Trp-1-specific CD8+ T cells from the 2 donors and transferred into CD90.1+ recipient mice, which had been challenged with tumor cells and vaccinated 3 days later. Cells were transferred 2 days after vaccination (FIG. 6A). Immediately before transfer FF- and diluent treated Trp-1- and E7-specific CD8+ T cells from donor mice show comparable expression of CD62L, CD127, KLRG1 and FoxO1, indicating that FF does not affect memory formation (FIG. 6B). FF-treated cells show increased expression of PD-1 and T-bet, suggestive of a higher activation status. FF treatment does not significantly enhance frequencies or functions of vaccine-induced CD8+ T cells (FIG. 6C). FF-treated splenocytes before transfer show enhanced OCR, which is blocked by Eto indicating that FF conditions vaccine-induced CD8+ T cells to enhance FAO (FIG. 6D).

Donor-derived vaccine-induced CD8+TILs were analyzed 3 weeks after transfer (data not shown). Compared to diluent-treated TILs of donor origin, FF-treated donor derived CD44+CD8+TILs show enhanced levels of transcripts for factors involved in FA catabolism (data not shown). Both Trp-1- and E7-specific FF donor-derived CD8+TILs show a trend towards increased PD-1 expression (FIG. 6E). Frequencies and functions of FF-treated, vaccine-induced CD8+TILs of donor origin are significantly higher compared to those of controls (FIG. 6F). Upon transfer of splenocytes from FF- or diluent-treated mice into separate cohorts of tumor-bearing mice, the former significantly delays tumor growth (FIG. 6G). Collectively these data confirm that enhanced FA catabolism improves antitumor functions of CD8+TILs.

Figure 6H:
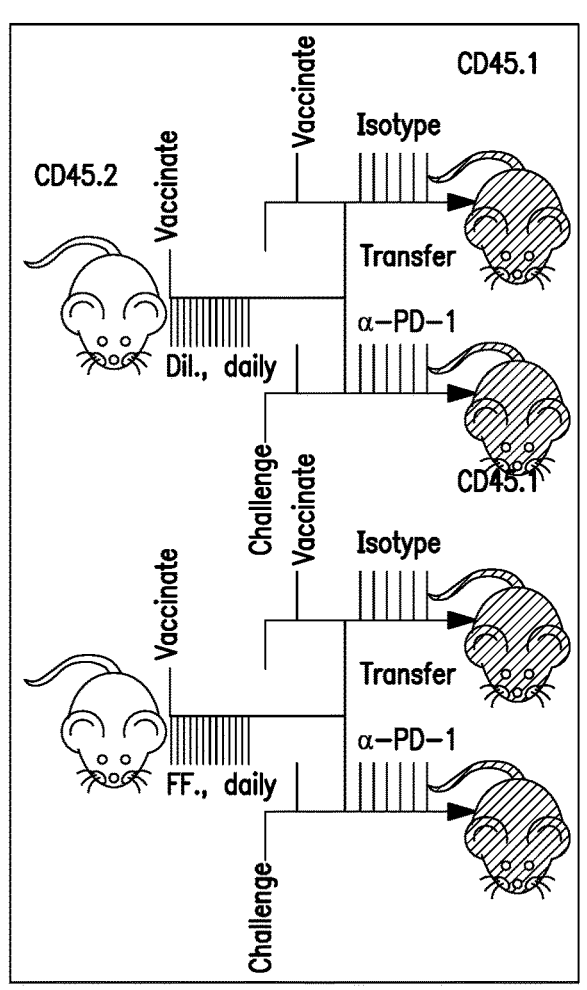
Figure 6I:
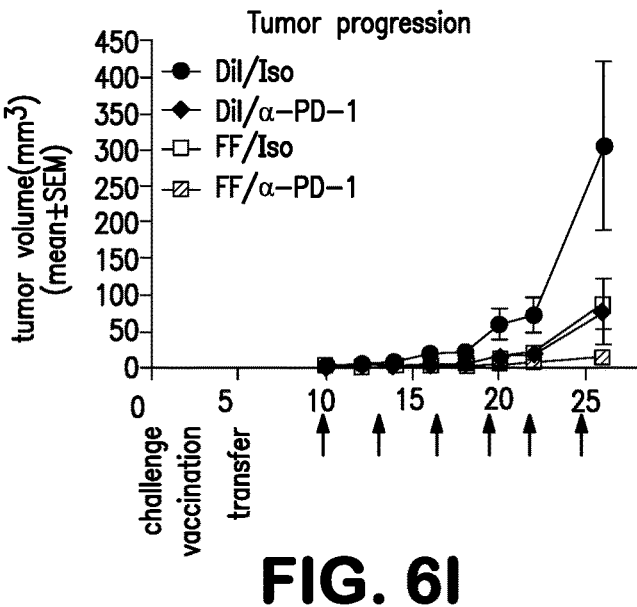
Figure 6J:
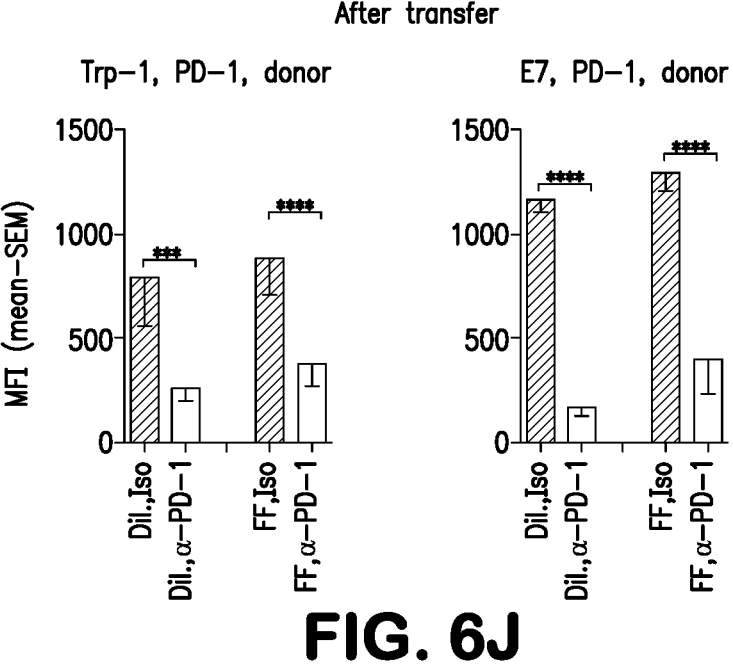

To test if FF-induced PD-1 increases affect FF-treated CD8+TIL functions, we fed vaccinated donor mice with FF or diluent daily for three weeks and then upon transfer into separate tumor-bearing mice treated the recipients with anti-PD-1 or isotype control antibodies (FIG. 6H). Both FF treatment of donors and anti-PD-1 treatment of recipients strongly delay tumor progression (FIG. 6I). Moreover, they act synergistically and together completely prevent tumor outgrowth in more than 30% of the vaccinated mice (FIG. 6I and not shown). Anti-PD-1 treatment reduces PD-1 staining on donor cells and this is not affected by FF (FIG. 6J). It only has subtle effects on frequencies and functions of MAA-specific CD8+TILs derived from either set of donor mice (data not shown). PD-1 blockade significantly increases frequencies of monofunctional E7-specific CD8+TILs derived from FF treated donors. This effect may partially reflect the smaller tumor sizes of α-PD-1 treated mice, which might rescue the bystander T cell functions more easily than those of MAA-specific CD8+TILs.

To further study how FA catabolism affects functions of CD8+TILs, we stimulated CD8+ T cells from PPARα KO mice in vitro and compared them to those from wildtype (wt) mice. Transcripts for most factors involved in the TCA cycle and lipid metabolism (e.g., IDH3a, MDH2, slc27a2, slc27a4, LIPA, Acaa1a, Acox1, Cpt1a and Acadv1) are higher in PPARα KO compared to wt CD8+ T cells when stimulated in Glu medium and under hypoxia; this profile reverses in cells cultured in Gal medium and low $O_2$, suggesting that PPARα inactivation significantly decreases FA catabolism by CD8+ T cells cultured without Glu (data not shown). PPARα KO compared to wt CD8+ T cells express lower levels of PD-1 when cultured in Gal-medium regardless of $O_2$ levels (FIG. 13A). Their functions and polyfunctionality are significantly lower compared to those of wt CD8+ T cells cultured in Gal-medium (FIG. 13B), suggesting that FA catabolism is required to maintain effector functions of CD8+ T cells activated with limited access to Glu.

We explored the effect of PPARα inactivation on vaccine-induced TIL functions in an adoptive transfer system, in which splenocytes from PPARα KO and wt mice were collected 3 weeks after vaccination, mixed at a 1:1 ratio of Trp-1-specific CD8+ T cells from the two donors and co-transferred into tumor-bearing and vaccinated recipient mice (FIG. 7A). Prior to transfer, functions and polyfunctionality of MAA-specific CD8+ T cells are similar between the two groups, while E7-specific CD8+ T cells are less abundant and polyfunctional in PPARα KO mice (data not shown). This difference may reflect that strength of T cell receptor (TCR) signaling, which is lower for the E7 epitope, affects at what time after activation cells switch to FA catabolism. Expression of CD127 is comparable between the two T cell subsets, indicating no major differences in memory formation (FIG. 7C). CD44+CD8+TILs from PPARα KO as compared to wt donors collected from recipient mice 3 weeks after transfer show a transcriptional profile similar to that of PPARα KO CD8+ T cells cultured in vitro in Gal medium under hypoxia, indicating reduced FA catabolism by PPARα KO CD8+TILs (figure not shown; but expression of IDH3a, MDH2, slc27a2, slc27a4, LIPA, Acaa1a, Acox1, Cpt1a, Acadv1 were decreased in the T cells from the PPAR-α KO mice compared to the wildtype). Both Trp-1- and E7-specific PPARα KO CD8+TILs show lower levels of PD-1 expression, concomitant with decreases in frequencies and functions including polyfunctionality comparing to those of donor-derived wt CD8+TILs (FIG. 7B and FIG. 7C). Collectively these data confirm that FA catabolism preserves CD8+ T cell effector functions under metabolically challenging conditions regardless of PD-1 expression levels.

Example 8: Usefulness of Pretreated T Cells in Treatment of Cancer

The inventors have shown that fenofibrate treatment during in vitro stimulation of OT-1 cells causes metabolic switching of T cell metabolism (FIGS. 15A-17E). CD8$^+$ T cells from OT-1 mice have a TCR that recognizes the OVA-derived peptide SIINFEKL SEQ ID NO: 1. See, e.g., Clarke, S R et al, 2000 Characterization of the ovalbumin-specific TCR transgenic line OT-I: MHC elements for positive and negative selection, Immunol. Cell Biol, 78(2):110-117. Therefore OT-1 cells are a good model of T cells that can be stimulated with any antigen, in this case the OVA-derived peptide, rather than a tumor-specific antigen.

To assess the effect of a T cell or T cell population that was pretreated in vitro with a compound or reagent that promotes the use of fatty acid catabolism rather than glucose for energy production, i.e., fenofibrate, on tumor growth in vivo, the following experiment was conducted.

Mice were injected with $10^5$ B16.F10 melanoma cells that were transduced to express the immunodominant epitope of ovalbumin SIINFEKL SEQ ID NO: 1. Five days later the mice received either (a) untreated OT-1 CD8+ T cells (i.v.) which express a transgenic T cell receptor for SIINFEKL (naïve OT-1 transfer), (b) OT-1 cells that were stimulated/activated in vitro with the SIINFEKL peptide and pre-treated with diluent (Ctrl treated OT-1), or (c) OT-1 cells that were stimulated/activated in vitro with the SIINFEKL peptide and pretreated with 25 μM of fenofibrate (FF).

Tumor growth in the mouse models was monitored for up to 24 days. The results are depicted in the graph of FIG. 16 showing that the growth of the tumor in mice treated with FF-pre-treated, activated T cells was inhibited compared to the response in the naïve, non-activated OT-1 cells or the activated, control-treated T cells.

Thus, the pretreated, activated T cell populations, such as CAR-T cells, or others, can have their metabolic functions switched and, when administered to a subject with a tumor, act to repress tumor growth. Such effect can be accomplished by administering pre-treated T cells alone, i.e., without any other anti-cancer immunotherapeutic, such as a tumor antigen specific vaccine. Thus the methods and compositions described herein are useful in adoptive T cell transfer therapeutic treatments using T cells, e.g., CAR-T cells, pretreated to switch their metabolic functions, resulting in enhanced treatment of cancer patients.

In summary, the data presented herein demonstrates that metabolism profoundly affects T cell differentiation and effector functions. Within the TME CD8$^+$ T cells experience hypoxia and have to compete for nutrients, especially Glu, which tumor cells consume to fuel glycolysis. Cells can compensate for lack of Glu by switching from glycolysis to OXPHOS, using alternative nutrients such as FAs. Recent studies report that hypoglycemia within the TME impairs CD8+ T cells functions and reduces the efficacy of active immunotherapy (Chang et al., 2015; Ho et al., 2015). Results presented here show that metabolic challenges within the TME impair the performance of CD8$^+$TILs including bystander TILs although TA-specific CD8$^+$TILs tend to be more affected. This reflects that TA-specific CD8$^+$TILs continue to receive stimulatory signals within the TME as evidenced by their proliferation. In addition, they may penetrate more deeply into tumors where nutrients and O$_2$ are especially limiting.

Solid tumors develop areas of hypoxia, which activates the HIF-1α pathway in cells of the TME. HIF-1α expression also rises upon T cell activation[20]. In the study HIF-1α increases in both MAA-specific and bystander CD8$^+$TILs, pointing towards hypoxia as the underlying cause. The effect of hypoxia on CD8$^+$ T cells is controversial. Some studies show that O$_2$ is required for T cell effector functions[28,30]. Others using protocols in which CD8$^+$ T cells were subjected to hypoxia during a resting period report that hypoxia increases functions[10,11] the data agree with the former as they show reduced HIF-1α signaling improves CD8+TIL frequencies and functions, indicating that when Glu is limiting, promoting glycolysis and inhibiting OXPHOS by HIF-1α becomes detrimental to CD8+TILs. LAG-3, which according to the data is regulated by HIF-1α inhibits T cell expansion and effector functions (Grosso et al., 2007). The LAG-3 locus has several HIF-1α response elements ([A/G] CGTA, (Pescador et al., 2005), which may influence LAG-3 expression under hypoxia. we show that hypoxia dampens effector functions of activated CD8$^+$ T cells in vitro, and reduced HIF-1α signaling in CD8$^+$TILs improves their frequencies and functions. The latter most likely reflects that when Glu is limiting within the TME, promotion of glycolysis and inhibition of OXPHOS by HIF-1α becomes detrimental. LAG-3, which according to the data is regulated by HIF-1α inhibits T cell expansion and effector functions[12]. An analysis of sequences of the LAG-3 locus reveals several HIF-1α response elements ([A/G]CGTA)[27], which may influence LAG-3 expression.

Hypoxia and hypoglycemia send opposing metabolic signals. The former promotes glycolysis while the latter forces cells to use OXPHOS, which can be fueled by various nutrients but requires O$_2$. the Cancer cells increase de novo lipogenesis[21] and recruit adipose progenitor cells[39]. Accordingly in the model the abundance of free FA species increases during tumor progression. the data show that CD8$^+$TILs cope with lack of Glu and O2 by augmenting FA uptake and FA catabolism to gain energy through OXPHOS. However, even with this metabolic switch CD8+TILs show loss of functions, which can be improved by further promoting lipid metabolism by FF.

High expression of PD-1 is viewed to signal CD8$^+$ T cell exhaustion and loss of effector functions. The results suggest that high PD-1 expression is not inevitably linked to impaired T cell functions. When activated CD8$^+$ T cells are exposed to hypoxia, their decreased expression of PD-1 is associated with impaired functions. In contrast, FF-treated CD8$^+$ T cells show a trend towards increased PD-1 expression but their functions improve PD-1 signaling inhibits TCR- and CD28-mediated activation of the PI3K/Akt/mTOR pathway, which in turn decreases glycolysis (Parry et al., 2005) and promotes lipolysis and FAO (Patsoukis et al., 2015). We speculate that enhanced PD-1 signaling in CD8+ TILs is beneficial by facilitating their metabolic switch within a Glu-poor TME. In the model blockade of PD-1 after the initial phase of T cell activation affects neither functions nor metabolism of TILs although overall Glu concentrations within the tumors increase. These results differ from those of a recent study in a mouse sarcoma model, which reports improved glycolysis and IFN-γ production by CD8+TILs treated with anti-PD-1 during their initial activation (Chang et al., 2015). These apparently opposing results reflect intrinsic differences in tumor models or in T cells induced by vaccination or through stimulation by tumor-derived antigens. Alternatively, differences in timing of treatment may affect the result. PD-1 blockade during the initial stages of T cell activation may allow them to better compete for Glu within a TME; once TILs have switched to FA catabolism they remain committed to this pathway regardless of PD-1 signaling.

Anti-PD-1 treatment delays tumor progression in the model. Some of the data suggest that anti-PD-1 may promote MAA-specific CD8+ T cell infiltration into tumors (not shown). However, as anti-PD-1 treatment also delays tumor progression in immune-deficient mice, we assume that it acts directly on tumor cells, tumor stromal cells or immunosuppressive cells within the TME. A recent study suggests that anti-PD-1 may reduce proliferation of PD-1+ tumor cells by blocking mTOR signaling (Kleffel et al., 2015). This mode of action of PD-1 blockade will only affect PD-1+ tumor cells. As the melanoma cells isolated from tumors grown in vivo express very low levels of PD-1 (data not shown); we view it as unlikely that they are directly affected by PD-1 blockade. Immunosuppressive cells express high levels of PD-1 (not shown) and PD-1 blockade may impair their ability to promote tumorigenesis (Marvel and Gabrilovich, 2015). Melanoma cells express PD-L1 (not shown) and back-signaling through this ligand increases the tumor cells' resistance to Fas- or CD8+ T cell mediated apoptosis (Azuma et al., 2008). Anti-PD-1 treatment could thus promote tumor cell death by enhancing their susceptibility to apoptosis or, in immunocompetent mice, indirectly improve TIL functions by increasing the tumor cells' susceptibility to lytic enzymes. Either mechanism could delay tumor growth and thus enhance levels of Glu within the TME. Although the additional Glu could fuel proliferation of tumor cells this would be counterbalanced by their increased death rates.

Energy production through FAO rather than glycolysis comes at a price; more $O_2$ is needed to generate equivalent amounts of ATP and ROS production increases. Generating energy through FAO within a hypoxic TME may thus not be the only method by which CD8+TILs maintain their functions. Ketone bodies are highly efficient fuels that require less $O_2$ (Veech, 2004) and previous studies showed that they serve as the preferred energy source for cells of the nervous system subjected to hypoxia and hypoglycemia (Takahashi et al., 2014).

Ketone bodies could be synthesized and secreted by other cells (Martinez-Outschoorn et al., 2012), or they could be produced by TILs directly as suggested by increased transcript levels of Bdh1, a key enzyme in ketone body metabolism. The data show that CD8+TILs show pronounced increases in the intensities of ketone bodies acetoacetate and 3-hydroxybutyrate during tumor progression. Additionally, levels of $O_2$ differ within a tumor and TILs can randomly migrate within the TME (Mrass et al., 2006). TILs could use FAO and ketone bodies alternatively depending on surrounding $O_2$ levels to maintain their effector functions and prolong their survival.

As suggested by the results, metabolic reprogramming of CD8+ T cells to increase energy production through FA catabolism prior to adoptive cell transfer enhances the overall efficacy of cell therapy in patients with some types of cancers, especially those characterized by low Glu content like melanomas. In agreement, other studies show that memory CD8+ T cells, which prefer FAO and OXPHOS for energy production, are better at slowing tumor progression than effector cells (Crompton et al., 2015; Sukumar et al., 2013). In contrast, others report that increasing the TILs' ability to use glycolysis improves their antitumor effect (Chang et al., 2015). Which metabolic manipulations are most suited to improve TIL-mediated tumor regression will likely depend on the nature of the tumor. Those with sufficient levels of Glu may benefit from CD8+ T cells with high glycolytic potential, while tumors with a hypoglycemic TME may best be combated by CD8+ T cells that favor FA catabolism.

The results herein show that metabolic challenges within the TME have profound impacts on CD8+TILs. It forces CD8+TILs to increasingly gain energy through FA catabolism, including consumption of ketone bodies, which partially preserves their functions and may improve their survival. Promoting the CD8+TILs' propensity to use FAO combined with PD-1 signaling blockade further improves treatment outcome. These results invite further investigations to assess if the outcome of cancer immunotherapy can be improved by adding metabolic manipulations to current treatment strategies.

Data suggest that high PD-1 expression is not inevitably linked to impaired T cell functions. PD-1 inhibits T cell receptor- and CD28-mediated activation of the mTOR pathway, which in turn decreases glycolysis[24] and promotes lipolysis and fatty acid catabolism[25]. PD-1 may be regulated by environmental cues, which direct CD8[+] T cells to adjust their metabolism. Under hypoxia when Glu is available, glycolysis provides an easy source of $O_2$-independent energy, which requires reduced PD-1 expression. When Glu and $O_2$ are limiting, CD8[+] T cells increase PD-1 expression, which facilitates FA metabolism.

As supported by the results, metabolic reprogramming of CD8[+] T cells to increase energy production through FA catabolism prior to adoptive cell transfer enhances the overall efficacy of cell therapy in patients with some types of cancers, especially those characterized by low Glu content, like melanomas. In agreement, other studies show that memory CD8[+] T cells, which prefer fatty acid catabolism and OXPHOS for energy production, are better at slowing tumor progression than effector cells[31,8]. In contrast, others report that increasing the TILs' ability to use glycolysis improves their antitumor effect[6]. Which metabolic manipulations are most suited to improve TIL-mediated tumor regression depends on the nature of the tumor. Those with sufficient levels of Glu may benefit from CD8[+] T cells with high glycolytic potential while tumors with a hypoglycemic TME may best be combated by CD8[+] T cells, which favor FA catabolism.

Thus, the inventors have shown that metabolic stress within the TME has profound effects on CD8[+]TILs. It forces CD8[+]TILs to increasingly gain energy through FA catabolism, including consumption of ketone bodies, which preserves their functions and may improve their survival. Thus enhancing the FA metabolism of tumor infiltrating CD8+ T cells increases the efficacy of active immunotherapy of cancers such as melanoma. The outcome of immunotherapy can be improved by metabolic manipulations.

The inventors have determined that treatment with an anti-PD-1 mAb slows tumor progression without changing CD8+TILs' metabolism or functions. Treatment with anti-PD-1 effectively delays tumor progression in vaccinated as well as unvaccinated or even immune-deficient NSG mice, which lack T, B and natural killer cells, suggesting that PD-1 checkpoint blockade delays tumor progression in a T cell-independent manner.

Anti-PD-1 treatment acts synergistically with metabolic reprogramming of TILs to achieve superior antitumor efficacy. Both fenofibrate treatment (FF- an agonist of PPAR-alpha that increases FA catabolism) of donors and anti-PD-1 treatment of recipients strongly delay tumor progression and act synergistically together to completely prevent tumor outgrowth in more than 30% of vaccinated mice (FIGS. 6I-6J).

FA catabolism improves T cell functions through multiple mechanisms: It contributes to energy production. It contributes to amino acid synthesis and production of effector molecules. It contributes to acetyl-CoA pool in the cytosol, acetylates GAPDH and enhances IFN-$\gamma$ translation. The data demonstrates that metabolic manipulations that condition tumor-associated-specific T cells to optimally cope with the metabolic constraints within the TME can significantly improve the overall efficacy of cancer therapy.

TABLE 3

| (Sequence Listing Free Text) The following information is provided for sequences containing free text under numeric identifier <223>. | |
| --- | --- |
| SEQ ID NO: (containing free text) | Free text under <223> |
| 2 | Forward primer |
| 3 | Reverse primer |
| 4 | Forward primer |
| 5 | Reverse primer |
| 6 | Forward primer |
| 7 | Reverse primer |
| 8 | Forward primer |
| 9 | Reverse primer |
| 10 | Forward primer |
| 11 | Reverse primer |
| 12 | Forward primer |
| 13 | Reverse primer |
| 14 | Forward primer |
| 15 | Reverse primer |
| 16 | Forward primer |
| 17 | Reverse primer |
| 18 | Forward primer |
| 19 | Reverse primer |
| 20 | Forward primer |
| 21 | Reverse primer |
| 22 | Forward primer |
| 23 | Reverse primer |
| 24 | Forward primer |
| 25 | Reverse primer |
| 26 | Forward primer |
| 27 | Reverse primer |
| 28 | Forward primer |
| 29 | Reverse primer |
| 30 | Forward primer |
| 31 | Reverse primer |
| 32 | Forward primer |
| 33 | Reverse primer |
| 34 | Forward primer |
| 35 | Reverse primer |
| 36 | Forward primer |
| 37 | Reverse primer |

TABLE 3-continued

| (Sequence Listing Free Text) The following information is provided for sequences containing free text under numeric identifier <223>. | |
| --- | --- |
| SEQ ID NO: (containing free text) | Free text under <223> |
| 38 | Forward primer |
| 39 | Reverse primer |
| 40 | Forward primer |
| 41 | Reverse primer |
| 42 | Forward primer |
| 43 | Reverse primer |
| 44 | Forward primer |
| 45 | Reverse primer |
| 46 | Forward primer |
| 47 | Reverse primer |

Each and every patent, patent application, including priority U.S. provisional application Nos. 62/279,252, 62/419,775, and 62/420,271, filed Jan. 15, 2016, Nov. 9, 2016 and Nov. 10, 2016, respectively, and each and every publication, including websites cited throughout the disclosure and listed herein, and the Sequence Listing accompanying this application, is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

REFERENCES

1. Ahmadzadeh, M., et al. (2009). Tumor antigen-specific CD8 T cells infiltrating the tumor express high levels of PD-1 and are functionally impaired. Blood 114: 1537-1544.

2. Bailey, K. M., et al. (2012). Targeting the metabolic microenvironment of tumors. Adv. Pharmacol. 65, 63-107.

3. Baitsch, L. (2011). Exhaustion of tumor-specific CD8+ T cells in metastases from melanoma patients. J. Clin. Invest. 121:2350-60.

4. Brahmer, J. R., et al. (2012). Safety and Activity of Anti-PD-L1 Antibody in Patients with Advanced Cancer. N. Engl. J. Med. 366, 2455-2465.

5. Bucks, C. M., et al. (2009). Chronic antigen stimulation alone is sufficient to drive CD8+ T cell exhaustion. J. Immunol. 182, 6697-6708.

6. Chang, C. H., et al. (2015) Metabolic Competition in the Tumor Microenvironment Is a Driver of Cancer Progression. Cell. 162, 1229-41.

7. Chapman, P. B., et al. (2015). Rapid eradication of a bulky melanoma with one dose of immunotherapy. N. Engl. J. Med. 372, 2073-2074.

8. Crompton, J. G., et al. (2015). Akt inhibition enhances expansion of potent tumor-specific lymphocytes with memory cell characteristics. Cancer. Res. 75, 296-305.

9. Dalgleish, A. G. (2011). Therapeutic cancer vaccines: Why so few randomized phase III studies reflect the initial optimism of phase II studies. Vaccine. 29: 8501-8505.

10. Doedens, A. L., et al. (2013). Hypoxia-inducible factors enhance the effector responses of CD8(+) T cells to persistent antigen. Nat Immunol.14, 1173-82.

11. Finlay, D., et al. (2012). PDK1 regulation of mTOR and hypoxia-inducible factor 1 integrate metabolism and migration of CD8+ T cells. J. Exp. Med. 209, 2441-2453.

12. Grosso, J. F., et al. (2007). LAG-3 regulates CD8+ T cell accumulation and effector function in murine self- and tuor-tolerance systems. J. Clin. Invest. 117, 3383-3392.

13. Hamanaka, R. B. and Chandel, N. S. (2012). Targeting glucose metabolism for cancer therapy. J. Exp. Med. 209, 211-215.

14. Ho, P. C., et al. (2015). Phosphoenolpyruvate is a metabolic checkpoint of antitumor T cell response. Cell.162; 1217-28.

15. Lasaro, M. O. et al. (2008). Targeting of antigen to the herpesvirus entry mediator augments primary adaptive immune responses. Nat. Med. 14, 205-212.

16. Lochner, M., et al (2015). Fatty acid metabolism in the regulation of T cell function. Trends Immunol. 36: 472-478.

17. Lu, W., et al. (2010). Metabolomic analysis via reversed-phase ion-pairing liquid chromatography coupled to a stand alone orbitrap mass spectrometer. Anal. Chem. 82, 3212-21.

18. Martinez-Outschoorn, U. E., et al (2012). Ketone body utilization drives tumor growth and metastasis. Cell Cycle. 11, 3964-71.

19. Mazzone, M. (2014). Tumor stroma: a complexity dictated by the hypoxic tumor microenvironment. Oncogene 33, 1743-1754.

20. McNamee, E. N. (2013). Hypoxia and hypoxia-inducible factors as regulators of T cell development, differentiation, and function. Immunol. Res. 55, 58-70.

21. Mendendez, J. A. and Lupu, R. (2007). Fatty acid synthase and lipogenic phenotype in cancer pathogenesis. Nat. Rev. Cancer. 7, 763-777.

22. Mueller, S. N. and Ahmed, R. (2009). High antigen levels are the cause of T cell exhaustion during chronic viral infection. Proc. Natl. Acad. Sci. 106, 8623-8628.

23. Palmer, C. S., et al. (2015). Glucose metabolism regulates T cell activation, differentiation, and functions. Frontiers Immunol. 6, 1-6.

24. Parry, R. V., et al. (2005). CTLA-4 and PD-1 receptors inhibit T-cell activation by distinct mechanisms. Mol. Cell. Biol. 25, 9543-53.

25. Patsoukis, N., et al. (2015). PD-1 alters T-cell metabolic reprogramming by inhibiting glycolysis and promoting lipolysis and fatty acid oxidation. Nat. Commun. 6, 6692.

26. Pearce, E. L. (2013). Fueling immunity: insights into metabolism and lymphocyte function. Science. 342; 1242454.

27. Pescador, N., et al. (2005). Identification of a functional hypoxia-responsive element that regulates the expression of the egl nine homologue 3 (egln3/phd3) gene. Biochem. J. 390, 189-197.

28. Schlie, K., et al. (2011). When Cells Suffocate: Autophagy in Cancer and Immune Cells under Low Oxygen. Int J Cell Biol 2011, 470597-13.

29. Sharma, P. and Allison, J. P. (2015). Immune checkpoint targeting in cancer therapy: toward combination strategies with curative potential. Cell. 161, 205-214.

30. Siska, P. J. and Rathmell, J. C. (2015) T cell metabolic fitness in antitumor immunity. Trends Immunol. 36, 257-64.

31. Sukumar, M., et al. (2013). Inhibiting glycolytic metabolism enhances CD8+ T cell memory and antitumor function. J. Clin. Invest. 123, 4479-88.

32. Takahashi, S., et al. (2014). Roles and regulation of ketogenesis in cultured astroglia and neurons under hypoxia and hypoglycemia. ASN. Neuro. 6, 5.

33. Veech, R. L. (2004). The therapeutic implications of ketone bodies: the effects of ketone bodies in pathological conditions: ketosis, ketogenic diet, redox states, insulin resistance, and mitochondrial metabolism. Prostaglandins. Leukot. Essent. Fatty. Acids. 70, 309-19

34. Wang, R. W. and Green, D. R. (2012). Metabolic checkpoints in activated T cells. Nat. Immunol. 13, 907-915.

35. Warburg, O., On respiratory impairment in cancer cells. (1956). Science. 124, 269-70.

36. Wherry, E. J. T cell exhaustion. (2011). Nat. Immunol. 12:492-499.

37. Wiig, H., et al. (2003). Isolation of interstitial fluid from rat mammary tumors by a centrifugation method. Am. J. Physiol. Heart. Circ. Physiol. 284, H416-24.

38. Yang, J. C. (2013). The adoptive transfer of cultured T cells for patients with metastatic melanoma. Clinics Dermatol. 31, 209-219.

39. Zhang, Y., et al. (2012). Stromal progenitor cells from endogenous adipose tissue contribute to pericytes and adipocytes that populate the tumor microenvironment. Cancer Res. 72, 5198-208.

40. Zhang, Y. and Ertl, H. C. (2014). The effect of adjuvanting cancer vaccines with herpes simples virus glycoprotein D on melanoma-driven CD8+ T cell exhaustion. J. Immunol. 193: 1836-1846.

41. Kalos, M. et al (2011) T cells with chimeric antigen receptors have potent antitumor effects and can establish Memory in Patients with Advanced Leukemia. Sci Transl Med., 3(95): 73

42. Azuma, T., et al., 2008. B7-H1 is a ubiquitous antiapoptotic receptor on cancer cells. Blood 111, 3635-3643

43. Kleffel, S., et al., 2015. Melanoma Cell-Intrinsic PD-1 Receptor Functions Promote Tumor Growth. Cell 162, 1242-1256.

44. Larkin, J., et al., 2015. Combined Nivolumab and Ipilimumab or Monotherapy in Untreated Melanoma. N Engl J Med 373, 23-34.

45. Marvel, D., Gabrilovich, D. I., 2015. Myeloid-derived suppressor cells in the tumor microenvironment: expect the unexpected. J. Clin. Invest. 125, 3356-3364.

46. Mrass, P., et al., 2006. Random migration precedes stable target cell interactions of tumor-infiltrating T cells. Journal of Experimental Medicine 203, 2749-2761.

47. Ohta, A., et al., 2011. In vivo T cell activation in lymphoid tissues is inhibited in the oxygen-poor microenvironment. Front Immunol 2, 27.

48. Patsoukis, N., et al, 2013. PD-1 increases PTEN phosphatase activity while decreasing PTEN protein stability by inhibiting casein kinase 2. Mol. Cell. Biol. 33, 3091-3098.

49. Tatsis, N., et al., 2007. Adenoviral vectors persist in vivo and maintain activated CD8+ T cells: implications for their use as vaccines. Blood 110, 1916-1923.

50. Zhang, F., 2012. Dysregulated lipid metabolism in cancer. World Journal of Biological Chemistry 3, 167

51. Zou, W., et al., 2016. PD-L1 (B7-H1) and PD-1 pathway blockade for cancer therapy: Mechanisms, response biomarkers, and combinations. Sci Transl Med 8, 328rv4-328rv4.

52. Clarke, S R et al, 2000 Characterization of the ovalbumin-specific TCR transgenic line OT-I: MHC elements for positive and negative selection., Immunol. Cell Biol, 78(2):110-117

The invention claimed is:

1. A method of modifying an activated T cell comprising pretreating the T cell ex vivo or in vitro with a compound or reagent that conditions the cell to use fatty acid catabolism for energy production by the T cells, wherein the compound or reagent that promotes the use of fatty acid catabolism by T cells is a PPARα agonist.

2. The method according to claim 1, wherein the T cell is a chimeric antigen receptor-T cell or a chimeric endocrine receptor-T cell or an ex vivo expanded tumor antigen-specific T cells and the method further comprising adoptive cell transfer to a subject having a solid tumor.

3. The method according to claim 1, further comprising administering to a subject in need thereof the modified T cell and a checkpoint inhibitor in the form of an antibody or a small molecule.

4. The method according to claim 3, wherein the checkpoint inhibitor is an anti-PD-1 antibody or small molecule ligand.

5. The method according to claim 1, wherein the compound or reagent that promotes the use of fatty acid catabolism by T cells is fenofibrate, clofibrate, gemfibrozil, ciprofibrate, bezafibrate, an AMPK activator or 5-aminoimidazole-4-carboxamide riboside.

6. The method according to claim 1, wherein the T cell is an autologous or heterologous, naturally occurring T cell or a recombinantly or synthetically modified T cell construct, or a human T cell or natural killer (NK) T cell or T infiltrating lymphocyte (TIL) obtained from the subject or from a bone marrow transplant match for the subject, or a T cell obtained from human peripheral blood or from the tumor microenvironment of the subject, or a T cell modified to express a heterologous antigen receptor, or a chimeric antigen receptor or a chimeric endocrine receptor prior to said pretreatment, or an endogenous or heterologous human T cell or human T cell line, or a CD8+ T cell.

7. The method according to claim 1, further comprising administering to a subject in need thereof the modified T cell and an immunotherapeutic composition wherein said immunotherapeutic composition is a recombinant virus or virus-like particle that expresses a cancer antigen, a DNA construct that expresses a cancer antigen, a composition comprising cancer antigens or fragments thereof as peptides or proteins, monoclonal antibodies or antigen-binding fragments that specifically bind cancer antigens.

8. The method according to claim 7, wherein:
(a) the immunotherapeutic composition and the fatty acid catabolism-promoting compound or reagent, or the immunotherapeutic composition and the pretreated T cell are administered substantially simultaneously; or
(b) the fatty acid catabolism-promoting compound or reagent or the pretreated T cells are administered once or repeatedly from at least one to 14 days after administration of the immunotherapeutic composition; or
(c) the immunotherapeutic composition is administered in a single dose or as one or more booster doses; or
(d) said composition (a) and (b) are independently administered systemically by intramuscular, intraperitoneal, intravenous, intratumoral or intranodal administration; or
(e) composition (b) is administered orally.

9. The method according to claim 1, wherein the pretreated T cells are administered to a subject in need thereof once or repeatedly or wherein the pretreated T cells are administered in a single dose or as one or more doses or wherein the pretreated T cells are administered systemically by intravenous injection or infusion.

10. The method according to claim 1, further comprising
(a) treating a subject with the modified T cell;
(b) treating the subject with other anti-cancer therapies; and
(c) treating the subject with chemotherapy before administering the pre-treated T cells.

11. The method according to claim 10, wherein the anti-cancer therapy comprises depleting the subject of lymphocytes and optionally surgically resecting the tumor prior to administration of the pretreated T cells.

12. The method according to claim 2, wherein the cancer or tumor targeted by the method is characterized by hypoxia, significant infiltration with T lymphocytes, and low glucose in the tumor microenvironment.

* * * * *